US010617738B2

(12) United States Patent
Bartlett et al.

(10) Patent No.: US 10,617,738 B2
(45) Date of Patent: Apr. 14, 2020

(54) MAMMALIAN EPHA4 POLYPEPTIDE DERIVATIVES LACKING ONE OR MORE N-GLYCOSYLATION SITES AND METHOD OF USE THEREOF

(71) Applicants: The University of Queensland, St Lucia (AU); THE COUNCIL OF THE QUEENSLAND INSTITUTE OF MEDICAL RESEARCH, Herston (AU)

(72) Inventors: Perry Bartlett, St Lucia (AU); Andrew Boyd, Fitzroy North (AU); Mike Gerometta, Robertson (AU); Leanne Cooper, Alderley (AU)

(73) Assignees: The University of Queensland, St Lucia (AU); The Council of The Queensland Institute of Medical Research, Herston (AU)

( * ) Notice: Subject to any disclaimer, the term of this patent is extended or adjusted under 35 U.S.C. 154(b) by 0 days.

(21) Appl. No.: 15/771,788

(22) PCT Filed: Oct. 27, 2016

(86) PCT No.: PCT/AU2016/051010
§ 371 (c)(1),
(2) Date: Apr. 27, 2018

(87) PCT Pub. No.: WO2017/070738
PCT Pub. Date: May 4, 2017

(65) Prior Publication Data
US 2018/0339020 A1 Nov. 29, 2018

(30) Foreign Application Priority Data
Oct. 27, 2015 (AU) ................. 2015904387

(51) Int. Cl.
| | |
|---|---|
| C07K 14/705 | (2006.01) |
| A61K 39/17 | (2006.01) |
| A61K 38/17 | (2006.01) |
| C07K 14/715 | (2006.01) |
| A61P 9/00 | (2006.01) |
| A61P 35/00 | (2006.01) |
| A61K 45/06 | (2006.01) |
| C07K 14/735 | (2006.01) |
| C12N 15/11 | (2006.01) |
| A61K 38/00 | (2006.01) |

(52) U.S. Cl.
CPC .......... *A61K 38/1796* (2013.01); *A61K 45/06* (2013.01); *A61P 9/00* (2018.01); *A61P 35/00* (2018.01); *C07K 14/70535* (2013.01); *C07K 14/715* (2013.01); *C12N 15/11* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,892,769 B2 | 2/2011 | Inoue et al. | |
| 8,137,926 B2 | 3/2012 | Inoue | |
| 8,865,426 B2 | 10/2014 | Inoue | |
| 2008/0003210 A1 | 1/2008 | Bruckheimer et al. | |
| 2008/0255044 A1 | 10/2008 | Bartlett et al. | |

FOREIGN PATENT DOCUMENTS

| | | |
|---|---|---|
| EP | 2260864 A1 | 12/2010 |
| WO | 2000/024413 | 5/2000 |
| WO | 2005/083086 | 9/2005 |

OTHER PUBLICATIONS

Pegg et al., Glycoengineering of EphA4 Fc leads to a unique, long-acting and broad spectrum, Eph receptor therapeutic antagonist, Jul. 26, 2017, Scientific Reports 7:6519, DOI:10.1038/s41598-017-06685-z, 11 pages (Year: 2017).*
Solá, et al., "Glycosylation of Therapeutic Proteins: An Effective Strategy to Optimize Efficacy," BioDrugs, 2010; 24(1); pp. 1-20.
International Search Report for PCT/AU2016/051010, nine pages (Jan. 2017).
Search Information Statement for PCT/AU2016/051010, five pages (Jan. 2017).
Written Opinion of ISA for PCT/AU2016/051010, four pages (Jan. 2017).
Dottori et al. "EphA4 (Sek1) receptor tyrosine kinase is required for the development of the corticospinal tract" Proc. Natl. Acad. Sci. USA 95:13248-13253 (1998).
Goldshmit et al. "EphA4 blockers promote axonal regeneration and functional recovery following spinal cord injury in mice" PLOS One 6:e24636, 12 pages (2011).
Spanevello et al. "Acute delivery of EphA4-Fc improves functional recovery after contusive spinal cord injury in rats" J. Neurotrauma 30:1023-1034 (2013).

* cited by examiner

*Primary Examiner* — John D Ulm
(74) *Attorney, Agent, or Firm* — Nixon & Vanderhye P.C.

(57) ABSTRACT

The present disclosure relates generally to the treatment of diseases and conditions exacerbated by signalling via the erythropoietin-producing-hepatoma receptor kinases EphA4 and to agents useful in such treatment.

27 Claims, 16 Drawing Sheets
Specification includes a Sequence Listing.

A

VTGSRVYPANEVTLLDSRSVQGELGWIASPLEGGWEEVSIMDEKNTPIRTYQVCNVMEPSQNNWLRTDWITREGAQRVYI  80
EIKFTLRDCNSLPGVMGTCKETFNLYYYESDNDKERFIRENQFVKIDTIAADESFTQVDIGDRIMKLNTEIRDVGPLSKK  160
GFYLAFQDVGACIALVSVRVFYKKCPLTVRNLAQFPDTITGADTSSLVEVRGSCVNNSEEKDVPKMYCGADGEWLVPIGN  240
CLCNAGHEERSGECQACKIGYYKALSTDATCAKCPPHSYSVWEGATSCTCDRGFFRADNDAASMPCTRPPSAPLNLISNV  320
NETSVNLEWSSPQNTGGRQDISYNVVCKKCGAGDPSKCRPCGSGVHYTPQQNGLKTTKVSITDLLAHTNYTFEIWAVNGV  400
SKYNPNPDQSVSVTVTTNQAAPSSIALVQAKEVTRYSVALAWLEPDRPNGVILEYEVKYYEKDQNERSYRIVRTAARNTD  480
IKGLNPLTSYVFHVRARTAAGYGDFSEPLEVTTNTVPSRIIGDGANS*ESKYGPPCPPCPAPEFLGGPSVFLFPPKPKDTL*  560
*MISRTPEVTCVVVDVSQEDPEVQFNWYVDGVEVHNAKTKPREEQFNSTYRVVSVLTVLHQDWLNGKEYKCKVSNKGLPSS*  640
*IEKTISKAKGQPREPQVYTLPPSQEEMTKNQVSLTCLVKGFYPSDIAVEWESNGQPENNYKTTPPVLDSDGSFFLYSRLT*  720
*VDKSRWQEGNVFSCSVMHEALHNHYTQKSLSLSLGK* (SEQ ID NO:1)

B 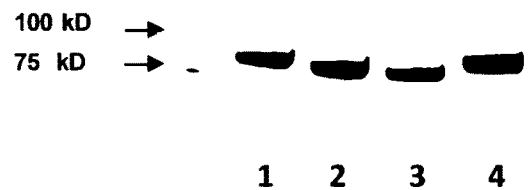

C 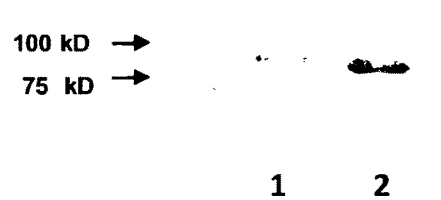

Figure 2

B1 = WT EphA4-Fc, D1 = double mutant, F1 = triple mutant

A
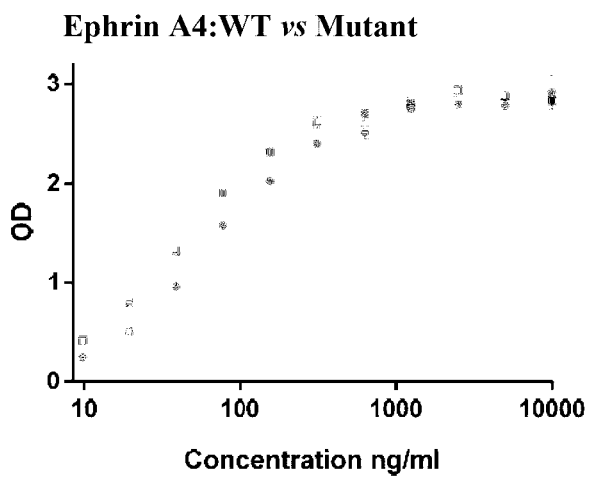
B
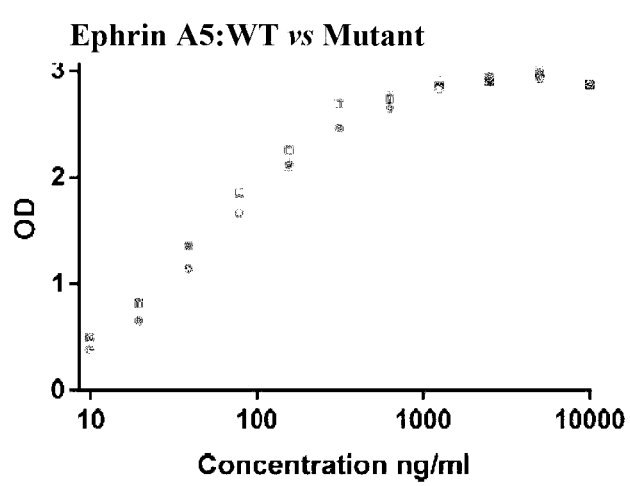
C
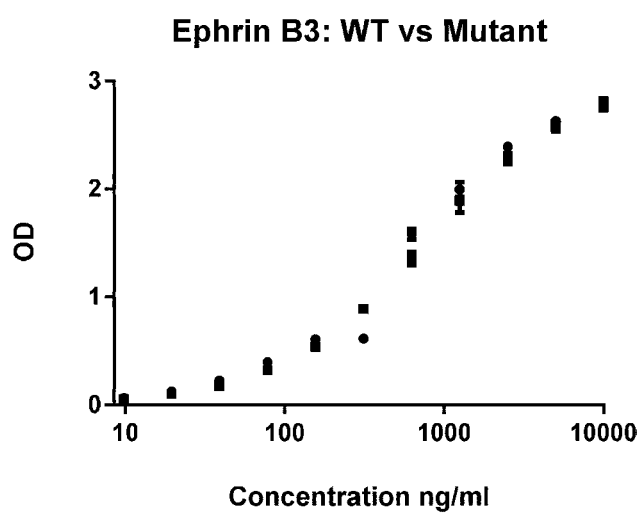
Figure 10

A.   EphA2 extracellular including 23 amino acid signal sequence

```
         10         20         30         40         50
MELQAARACF ALLWGCALAA AAAAQGKEVV LLDFAAAGGE LGWLTHPYGK
         60         70         80         90        100
GWDLMQNIMN DMPIYMYSVC NVMSGDQDNW LRTNWVYRGE AERIFIELKF
        110        120        130        140        150
TVRDCNSFPG GASSCKETFN LYYAESDLDY GTNFQKRLFT KIDTIAPDEI
        160        170        180        190        200
TVSSDFEARH VKLNVEERSV GPLTRKGFYL AFQDIGACVA LLSVRVYYKK
        210        220        230        240        250
CPELLQGLAH FPETIAGSDA PSLATVAGTC VDHAVVPPGG EEPRMHCAVD
        260        270        280        290        300
GEWLVPIGQC LCQAGYEKVE DACQACSPGF FKFEASESPC LECPEHTLPS
        310        320        330        340        350
PEGATSCECE EGFFRAPQDP ASMPCTRPPS APHYLTAVGM GAKVELRWTP
        360        370        380        390        400
PQDSGGREDI VYSVTCEQCW PESGECGPCE ASVRYSEPPH GLTRTSVTVS
        410        420        430        440        450
DLEPHMNYTF TVEARNGVSG LVTSRSFRTA SVSINQTEPP KVRLEGRSTT
        460        470        480        490        500
SLSVSWSIPP PQQSRVWKYE VTYRKKGDSN SYNVRRTEGF SVTLDDLAPD
        510        520        530        540        550
TTYLVQVQAL TQEGQGAGSK VHEFQTLSPE GSGNLAVIGG
(SEQ ID NO:29)
```

B.   EphA3 extracellular including 20 amino acid signal sequence

```
         10         20         30         40         50
MDCQLSILLL LSCSVLDSFG ELIPQPSNEV NLLDSKTIQG ELGWISYPSH
         60         70         80         90        100
GWEEISGVDE HYTPIRTYQV CNVMDHSQNN WLRTNWVPRN SAQKIYVELK
        110        120        130        140        150
FTLRDCNSIP LVLGTCKETF NLYYMESDDD HGVKFREHQF TKIDTIAADE
        160        170        180        190        200
SFTQMDLGDR ILKLNTEIRE VGPVNKKGFY LAFQDVGACV ALVSVRVYFK
        210        220        230        240        250
KCPFTVKNLA MFPDTVPMDS QSLVEVRGSC VNNSKEEDPP RMYCSTEGEW
        260        270        280        290        300
LVPIGKCSCN AGYEERGFMC QACRPGFYKA LDGNMKCAKC PPHSSTQEDG
        310        320        330        340        350
SMNCRCENNY FRADKDPPSM ACTRPPSSPR NVISNINETS VILDWSWPLD
        360        370        380        390        400
TGGRKDVTFN IICKKCGWNI KQCEPCSPNV RFLPRQFGLT NTTVTVTDLL
        410        420        430        440        450
AHTNYTFEID AVNGVSELSS PPRQFAAVSI TTNQAAPSPV LTIKKDRTSR
        460        470        480        490        500
NSISLSWQEP EHPNGIILDY EVKYYEKQEQ ETSYTILRAR GTNVTISSLK
        510        520        530        540        550
PDTIYVFQIR ARTAAGYGTN SRKFEFETSP DSFSISGESS Q
(SEQ ID NO:30)
```

Figure 11A and B

C. EphA4 extracellular including 19 amino acid signal sequence

```
        10         20         30         40         50
MAGIFYFALF SCLFGICDAV TGSRVYPANE VTLLDSRSVQ GELGWIASPL
        60         70         80         90        100
EGGWEEVSIM DEKNTPIRTY QVCNVMEPSQ NNWLRTDWIT REGAQRVYIE
       110        120        130        140        150
IKFTLRDCNS LPGVMGTCKE TFNLYYYESD NDKERFIREN QFVKIDTIAA
       160        170        180        190        200
DESFTQVDIG DRIMKLNTEI RDVGPLSKKG FYLAFQDVGA CIALVSVRVF
       210        220        230        240        250
YKKCPLTVRN LAQFPDTITG ADTSSLVEVR GSCVNNSEEK DVPKMYCGAD
       260        270        280        290        300
GEWLVPIGNC LCNAGHEERS GECQACKIGY YKALSTDATC AKCPPHSYSV
       310        320        330        340        350
WEGATSCTCD RGFFRADNDA ASMPCTRPPS APLNLISNVN ETSVNLEWSS
       360        370        380        390        400
PQNTGGRQDI SYNVVCKKCG AGDPSKCRPC GSGVHYTPQQ NGLKTTKVSI
       410        420        430        440        450
TDLLAHTNYT FEIWAVNGVS KYNPNPDQSV SVTVTTNQAA PSSIALVQAK
       460        470        480        490        500
EVTRYSVALA WLEPDRPNGV ILEYEVKYYE KDQNERSYRI VRTAARNTDI
       510        520        530        540        550
KGLNPLTSYV FHVRARTAAG YGDFSEPLEV TTNTVPSRII GDGANST
(SEQ ID NO:31)
```

D. EphB4 extracellular including 15 amino acid signal sequence

```
        10         20         30         40         50
MELRVLLCWA SLAAALEETL LNTKLETADL KWVTFPQVDG QWEELSGLDE
        60         70         80         90        100
EQHSVRTYEV CDVQRAPGQA HWLRTGWVPR RGAVHVYATL RFTMLECLSL
       110        120        130        140        150
PRAGRSCKET FTVFYYESDA DTATALTPAW MENPYIKVDT VAAEHLTRKR
       160        170        180        190        200
PGAEATGKVN VKTLRLGPLS KAGFYLAFQD QGACMALLSL HLFYKKCAQL
       210        220        230        240        250
TVNLTRFPET VPRELVVPVA GSCVVDAVPA PGPSPSLYCR EDGQWAEQPV
       260        270        280        290        300
TGCSCAPGFE AAEGNTKCRA CAQGTFKPLS GEGSCQPCPA NSHSNTIGSA
       310        320        330        340        350
VCQCRVGYFR ARTDPRGAPC TTPPSAPRSV VSRLNGSSLH LEWSAPLESG
       360        370        380        390        400
GREDLTYALR CRECRPGGSC APCGGDLTFD PGPRDLVEPW VVVRGLRPDF
       410        420        430        440        450
TYTFEVTALN GVSSLATGPV PFEPVNVTTD REVPPAVSDI RVTRSSPSSL
       460        470        480        490        500
SLAWAVPRAP SGAVLDYEVK YHEKGAEGPS SVRFLKTSEN RAELRGLKRG
       510        520        530        540        550
ASYLVQVRAR SEAGYGPFGQ EHHSQTQLDE SEGWREQ
(SEQ ID NO:32)
```

Figure 11C and D

(A)
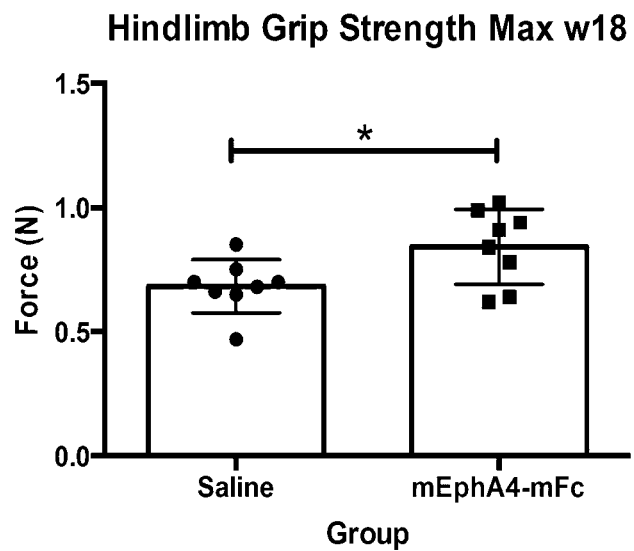
(b)
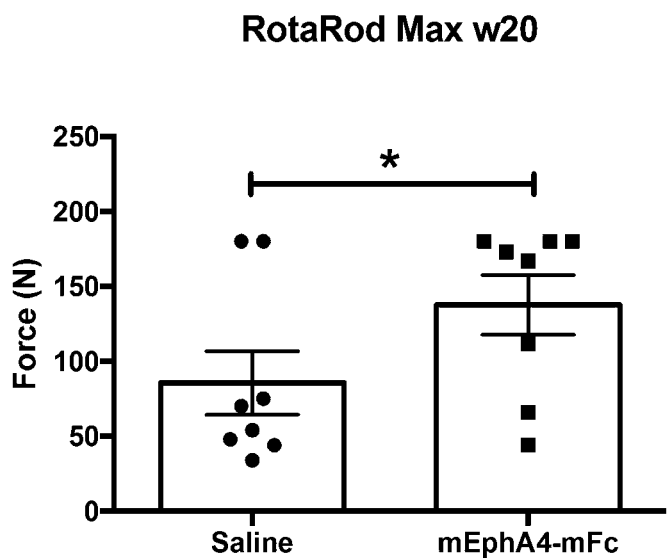
Figure 16

SEQUENCE LISTING

```
<160> NUMBER OF SEQ ID NOS: 37

<210> SEQ ID NO 1
<211> LENGTH: 756
<212> TYPE: PRT
<213> ORGANISM: Artificial Sequence
<220> FEATURE:
<223> OTHER INFORMATION: unmodified human-derived EphA4-Fc synthetic
      polypeptide

<400> SEQUENCE: 1

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
    210                 215                 220

Lys Met Tyr Cys Gly Ala Asp Gly Glu Trp Leu Val Pro Ile Gly Asn
```

```
              225                 230                 235                 240
        Cys Leu Cys Asn Ala Gly His Glu Glu Arg Ser Gly Glu Cys Gln Ala
                        245                 250                 255
        Cys Lys Ile Gly Tyr Tyr Lys Ala Leu Ser Thr Asp Ala Thr Cys Ala
                        260                 265                 270
        Lys Cys Pro Pro His Ser Tyr Ser Val Trp Glu Gly Ala Thr Ser Cys
                        275                 280                 285
        Thr Cys Asp Arg Gly Phe Phe Arg Ala Asp Asn Asp Ala Ala Ser Met
                        290                 295                 300
        Pro Cys Thr Arg Pro Pro Ser Ala Pro Leu Asn Leu Ile Ser Asn Val
        305                 310                 315                 320
        Asn Glu Thr Ser Val Asn Leu Glu Trp Ser Ser Pro Gln Asn Thr Gly
                        325                 330                 335
        Gly Arg Gln Asp Ile Ser Tyr Asn Val Val Cys Lys Lys Cys Gly Ala
                        340                 345                 350
        Gly Asp Pro Ser Lys Cys Arg Pro Cys Gly Ser Gly Val His Tyr Thr
                        355                 360                 365
        Pro Gln Gln Asn Gly Leu Lys Thr Thr Lys Val Ser Ile Thr Asp Leu
                        370                 375                 380
        Leu Ala His Thr Asn Tyr Thr Phe Glu Ile Trp Ala Val Asn Gly Val
        385                 390                 395                 400
        Ser Lys Tyr Asn Pro Asn Pro Asp Gln Ser Val Ser Val Thr Val Thr
                        405                 410                 415
        Thr Asn Gln Ala Ala Pro Ser Ser Ile Ala Leu Val Gln Ala Lys Glu
                        420                 425                 430
        Val Thr Arg Tyr Ser Val Ala Leu Ala Trp Leu Glu Pro Asp Arg Pro
                        435                 440                 445
        Asn Gly Val Ile Leu Glu Tyr Glu Val Lys Tyr Tyr Glu Lys Asp Gln
                        450                 455                 460
        Asn Glu Arg Ser Tyr Arg Ile Val Arg Thr Ala Ala Arg Asn Thr Asp
        465                 470                 475                 480
        Ile Lys Gly Leu Asn Pro Leu Thr Ser Tyr Val Phe His Val Arg Ala
                        485                 490                 495
        Arg Thr Ala Ala Gly Tyr Gly Asp Phe Ser Glu Pro Leu Glu Val Thr
                        500                 505                 510
        Thr Asn Thr Val Pro Ser Arg Ile Ile Gly Asp Gly Ala Asn Ser Glu
                        515                 520                 525
        Ser Lys Tyr Gly Pro Pro Cys Pro Pro Cys Pro Ala Pro Glu Phe Leu
                        530                 535                 540
        Gly Gly Pro Ser Val Phe Leu Phe Pro Pro Lys Pro Lys Asp Thr Leu
        545                 550                 555                 560
        Met Ile Ser Arg Thr Pro Glu Val Thr Cys Val Val Val Asp Val Ser
                        565                 570                 575
        Gln Glu Asp Pro Glu Val Gln Phe Asn Trp Tyr Val Asp Gly Val Glu
                        580                 585                 590
        Val His Asn Ala Lys Thr Lys Pro Arg Glu Glu Gln Phe Asn Ser Thr
                        595                 600                 605
        Tyr Arg Val Val Ser Val Leu Thr Val Leu His Gln Asp Trp Leu Asn
                        610                 615                 620
        Gly Lys Glu Tyr Lys Cys Lys Val Ser Asn Lys Gly Leu Pro Ser Ser
        625                 630                 635                 640
        Ile Glu Lys Thr Ile Ser Lys Ala Lys Gly Gln Pro Arg Glu Pro Gln
                        645                 650                 655
```

```
Val Tyr Thr Leu Pro Pro Ser Gln Glu Glu Met Thr Lys Asn Gln Val
            660             665             670

Ser Leu Thr Cys Leu Val Lys Gly Phe Tyr Pro Ser Asp Ile Ala Val
        675             680             685

Glu Trp Glu Ser Asn Gly Gln Pro Glu Asn Asn Tyr Lys Thr Thr Pro
    690             695             700

Pro Val Leu Asp Ser Asp Gly Ser Phe Phe Leu Tyr Ser Arg Leu Thr
705             710             715             720

Val Asp Lys Ser Arg Trp Gln Glu Gly Asn Val Phe Ser Cys Ser Val
                725             730             735

Met His Glu Ala Leu His Asn His Tyr Thr Gln Lys Ser Leu Ser Leu
            740             745             750

Ser Leu Gly Lys
        755

<210> SEQ ID NO 2
<211> LENGTH: 756
<212> TYPE: PRT
<213> ORGANISM: Artificial Sequence
<220> FEATURE:
<223> OTHER INFORMATION: modified human EphA4-Fc synthetic polypeptide

<400> SEQUENCE: 2

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65              70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145             150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Gln Asn Ser Glu Lys Asp Val Pro
    210                 215                 220

Lys Met Tyr Cys Gly Ala Asp Gly Glu Trp Leu Val Pro Ile Gly Asn
225             230                 235                 240

Cys Leu Cys Asn Ala Gly His Glu Glu Arg Ser Gly Glu Cys Gln Ala
                245                 250                 255
```

```
Cys Lys Ile Gly Tyr Tyr Lys Ala Leu Ser Thr Asp Ala Thr Cys Ala
            260                 265                 270

Lys Cys Pro Pro His Ser Tyr Ser Val Trp Glu Gly Ala Thr Ser Cys
            275                 280                 285

Thr Cys Asp Arg Gly Phe Phe Arg Ala Asp Asn Asp Ala Ala Ser Met
            290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
                340                 345                 350

Gly Asp Pro Ser Lys Cys Arg Pro Cys Gly Ser Gly Val His Tyr Thr
            355                 360                 365

Pro Gln Gln Asn Gly Leu Lys Thr Thr Lys Val Ser Ile Thr Asp Leu
    370                 375                 380

Leu Ala His Thr Asn Tyr Thr Phe Glu Ile Trp Ala Val Asn Gly Val
385                 390                 395                 400

Ser Lys Tyr Asn Pro Asn Pro Asp Gln Ser Val Ser Val Thr Val Thr
                405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
            435                 440                 445

Asn Gly Val Ile Leu Glu Tyr Glu Val Lys Tyr Tyr Glu Lys Asp Gln
            450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Glu
            515                 520                 525

Ser Lys Tyr Gly Pro Pro Cys Pro Pro Cys Pro Ala Pro Glu Phe Leu
            530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Glu Val Gln Phe Asn Trp Tyr Val Asp Gly Val Glu
            580                 585                 590

Val His Asn Ala Lys Thr Lys Pro Arg Glu Glu Gln Phe Asn Ser Thr
            595                 600                 605

Tyr Arg Val Val Ser Val Leu Thr Val Leu His Gln Asp Trp Leu Asn
            610                 615                 620

Gly Lys Glu Tyr Lys Cys Lys Val Ser Asn Lys Gly Leu Pro Ser Ser
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Gln Glu Glu Met Thr Lys Asn Gln Val
            660                 665                 670
```

-continued

```
Ser Leu Thr Cys Leu Val Lys Gly Phe Tyr Pro Ser Asp Ile Ala Val
            675                 680                 685

Glu Trp Glu Ser Asn Gly Gln Pro Glu Asn Asn Tyr Lys Thr Thr Pro
    690                 695                 700

Pro Val Leu Asp Ser Asp Gly Ser Phe Phe Leu Tyr Ser Arg Leu Thr
705                 710                 715                 720

Val Asp Lys Ser Arg Trp Gln Glu Gly Asn Val Phe Ser Cys Ser Val
                725                 730                 735

Met His Glu Ala Leu His Asn His Tyr Thr Gln Lys Ser Leu Ser Leu
            740                 745                 750

Ser Leu Gly Lys
        755
```

<210> SEQ ID NO 3
<211> LENGTH: 756
<212> TYPE: PRT
<213> ORGANISM: Artificial Sequence
<220> FEATURE:
<223> OTHER INFORMATION: modified human EphA4-Fc synthetic polypeptide

<400> SEQUENCE: 3

```
Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255

Cys Lys Ile Gly Tyr Tyr Lys Ala Leu Ser Thr Asp Ala Thr Cys Ala
            260                 265                 270
```

```
Lys Cys Pro Pro His Ser Tyr Ser Val Trp Glu Gly Ala Thr Ser Cys
            275                 280                 285
Thr Cys Asp Arg Gly Phe Phe Arg Ala Asp Asn Asp Ala Ala Ser Met
        290                 295                 300
Pro Cys Thr Arg Pro Pro Ser Ala Pro Leu Asn Leu Ile Ser Asn Val
305                 310                 315                 320
Gln Glu Thr Ser Val Asn Leu Glu Trp Ser Ser Pro Gln Asn Thr Gly
                325                 330                 335
Gly Arg Gln Asp Ile Ser Tyr Asn Val Val Cys Lys Lys Cys Gly Ala
            340                 345                 350
Gly Asp Pro Ser Lys Cys Arg Pro Cys Gly Ser Gly Val His Tyr Thr
        355                 360                 365
Pro Gln Gln Asn Gly Leu Lys Thr Thr Lys Val Ser Ile Thr Asp Leu
    370                 375                 380
Leu Ala His Thr Asn Tyr Thr Phe Glu Ile Trp Ala Val Asn Gly Val
385                 390                 395                 400
Ser Lys Tyr Asn Pro Asn Pro Asp Gln Ser Val Ser Val Thr Val Thr
                405                 410                 415
Thr Asn Gln Ala Ala Pro Ser Ser Ile Ala Leu Val Gln Ala Lys Glu
            420                 425                 430
Val Thr Arg Tyr Ser Val Ala Leu Ala Trp Leu Glu Pro Asp Arg Pro
        435                 440                 445
Asn Gly Val Ile Leu Glu Tyr Glu Val Lys Tyr Tyr Glu Lys Asp Gln
    450                 455                 460
Asn Glu Arg Ser Tyr Arg Ile Val Arg Thr Ala Ala Arg Asn Thr Asp
465                 470                 475                 480
Ile Lys Gly Leu Asn Pro Leu Thr Ser Tyr Val Phe His Val Arg Ala
                485                 490                 495
Arg Thr Ala Ala Gly Tyr Gly Asp Phe Ser Glu Pro Leu Glu Val Thr
            500                 505                 510
Thr Asn Thr Val Pro Ser Arg Ile Ile Gly Asp Gly Ala Asn Ser Glu
        515                 520                 525
Ser Lys Tyr Gly Pro Pro Cys Pro Pro Cys Pro Ala Pro Glu Phe Leu
    530                 535                 540
Gly Gly Pro Ser Val Phe Leu Phe Pro Pro Lys Pro Lys Asp Thr Leu
545                 550                 555                 560
Met Ile Ser Arg Thr Pro Glu Val Thr Cys Val Val Val Asp Val Ser
                565                 570                 575
Gln Glu Asp Pro Glu Val Gln Phe Asn Trp Tyr Val Asp Gly Val Glu
            580                 585                 590
Val His Asn Ala Lys Thr Lys Pro Arg Glu Glu Gln Phe Asn Ser Thr
        595                 600                 605
Tyr Arg Val Val Ser Val Leu Thr Val Leu His Gln Asp Trp Leu Asn
    610                 615                 620
Gly Lys Glu Tyr Lys Cys Lys Val Ser Asn Lys Gly Leu Pro Ser Ser
625                 630                 635                 640
Ile Glu Lys Thr Ile Ser Lys Ala Lys Gly Gln Pro Arg Glu Pro Gln
                645                 650                 655
Val Tyr Thr Leu Pro Pro Ser Gln Glu Glu Met Thr Lys Asn Gln Val
            660                 665                 670
Ser Leu Thr Cys Leu Val Lys Gly Phe Tyr Pro Ser Asp Ile Ala Val
        675                 680                 685
Glu Trp Glu Ser Asn Gly Gln Pro Glu Asn Asn Tyr Lys Thr Thr Pro
```

```
            690             695             700
Pro Val Leu Asp Ser Asp Gly Ser Phe Phe Leu Tyr Ser Arg Leu Thr
705             710             715             720

Val Asp Lys Ser Arg Trp Gln Glu Gly Asn Val Phe Ser Cys Ser Val
            725             730             735

Met His Glu Ala Leu His Asn His Tyr Thr Gln Lys Ser Leu Ser Leu
            740             745             750

Ser Leu Gly Lys
            755

<210> SEQ ID NO 4
<211> LENGTH: 756
<212> TYPE: PRT
<213> ORGANISM: Artificial Sequence
<220> FEATURE:
<223> OTHER INFORMATION: modified human EphA4-Fc synthetic polypeptide

<400> SEQUENCE: 4

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255

Cys Lys Ile Gly Tyr Tyr Lys Ala Leu Ser Thr Asp Ala Thr Cys Ala
            260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
```

```
            290                 295                 300
Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
                340                 345                 350

Gly Asp Pro Ser Lys Cys Arg Pro Cys Gly Ser Gly Val His Tyr Thr
                355                 360                 365

Pro Gln Gln Asn Gly Leu Lys Thr Thr Lys Val Ser Ile Thr Asp Leu
        370                 375                 380

Leu Ala His Thr Gln Tyr Thr Phe Glu Ile Trp Ala Val Asn Gly Val
385                 390                 395                 400

Ser Lys Tyr Asn Pro Asn Pro Asp Gln Ser Val Ser Val Thr Val Thr
                405                 410                 415

Thr Asn Gln Ala Ala Pro Ser Ser Ile Ala Leu Val Gln Ala Lys Glu
                420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
                500                 505                 510

Thr Asn Thr Val Pro Ser Arg Ile Ile Gly Asp Gly Ala Asn Ser Glu
                515                 520                 525

Ser Lys Tyr Gly Pro Pro Cys Pro Pro Cys Pro Ala Pro Glu Phe Leu
        530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Glu Val Gln Phe Asn Trp Tyr Val Asp Gly Val Glu
                580                 585                 590

Val His Asn Ala Lys Thr Lys Pro Arg Glu Glu Gln Phe Asn Ser Thr
                595                 600                 605

Tyr Arg Val Val Ser Val Leu Thr Val Leu His Gln Asp Trp Leu Asn
        610                 615                 620

Gly Lys Glu Tyr Lys Cys Lys Val Ser Asn Lys Gly Leu Pro Ser Ser
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Gln Glu Glu Met Thr Lys Asn Gln Val
                660                 665                 670

Ser Leu Thr Cys Leu Val Lys Gly Phe Tyr Pro Ser Asp Ile Ala Val
                675                 680                 685

Glu Trp Glu Ser Asn Gly Gln Pro Glu Asn Asn Tyr Lys Thr Thr Pro
        690                 695                 700

Pro Val Leu Asp Ser Asp Gly Ser Phe Phe Leu Tyr Ser Arg Leu Thr
705                 710                 715                 720
```

-continued

Val Asp Lys Ser Arg Trp Gln Glu Gly Asn Val Phe Ser Cys Ser Val
            725                 730                 735

Met His Glu Ala Leu His Asn His Tyr Thr Gln Lys Ser Leu Ser Leu
            740                 745                 750

Ser Leu Gly Lys
        755

<210> SEQ ID NO 5
<211> LENGTH: 756
<212> TYPE: PRT
<213> ORGANISM: Artificial Sequence
<220> FEATURE:
<223> OTHER INFORMATION: modified human EphA4-Fc synthetic polypeptide

<400> SEQUENCE: 5

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Gln Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255

Cys Lys Ile Gly Tyr Tyr Lys Ala Leu Ser Thr Asp Ala Thr Cys Ala
            260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
    290                 295                 300

Pro Cys Thr Arg Pro Pro Ser Ala Pro Leu Asn Leu Ile Ser Asn Val
305                 310                 315                 320

```
Gln Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
            355                 360                 365

Pro Gln Gln Asn Gly Leu Lys Thr Thr Lys Val Ser Ile Thr Asp Leu
        370                 375                 380

Leu Ala His Thr Asn Tyr Thr Phe Glu Ile Trp Ala Val Asn Gly Val
385                 390                 395                 400

Ser Lys Tyr Asn Pro Asn Pro Asp Gln Ser Val Ser Val Thr Val Thr
                405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
    450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Glu
            515                 520                 525

Ser Lys Tyr Gly Pro Pro Cys Pro Pro Cys Pro Ala Pro Glu Phe Leu
        530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Glu Val Gln Phe Asn Trp Tyr Val Asp Gly Val Glu
            580                 585                 590

Val His Asn Ala Lys Thr Lys Pro Arg Glu Glu Gln Phe Asn Ser Thr
            595                 600                 605

Tyr Arg Val Val Ser Val Leu Thr Val Leu His Gln Asp Trp Leu Asn
        610                 615                 620

Gly Lys Glu Tyr Lys Cys Lys Val Ser Asn Lys Gly Leu Pro Ser Ser
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Gln Glu Glu Met Thr Lys Asn Gln Val
            660                 665                 670

Ser Leu Thr Cys Leu Val Lys Gly Phe Tyr Pro Ser Asp Ile Ala Val
            675                 680                 685

Glu Trp Glu Ser Asn Gly Gln Pro Glu Asn Asn Tyr Lys Thr Thr Pro
        690                 695                 700

Pro Val Leu Asp Ser Asp Gly Ser Phe Phe Leu Tyr Ser Arg Leu Thr
705                 710                 715                 720

Val Asp Lys Ser Arg Trp Gln Glu Gly Asn Val Phe Ser Cys Ser Val
                725                 730                 735
```

Met His Glu Ala Leu His Asn His Tyr Thr Gln Lys Ser Leu Ser Leu
                740                 745                 750

Ser Leu Gly Lys
        755

<210> SEQ ID NO 6
<211> LENGTH: 756
<212> TYPE: PRT
<213> ORGANISM: Artificial Sequence
<220> FEATURE:
<223> OTHER INFORMATION: modified human EphA4-Fc synthetic polypeptide

<400> SEQUENCE: 6

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Gln Asn Ser Glu Glu Lys Asp Val Pro
210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255

Cys Lys Ile Gly Tyr Tyr Lys Ala Leu Ser Thr Asp Ala Thr Cys Ala
            260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
    290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

-continued

```
Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
        355                 360                 365

Pro Gln Gln Asn Gly Leu Lys Thr Thr Lys Val Ser Ile Thr Asp Leu
    370                 375                 380

Leu Ala His Thr Gln Tyr Thr Phe Glu Ile Trp Ala Val Asn Gly Val
385                 390                 395                 400

Ser Lys Tyr Asn Pro Asn Pro Asp Gln Ser Val Ser Val Thr Val Thr
                405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
    450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Glu
        515                 520                 525

Ser Lys Tyr Gly Pro Pro Cys Pro Pro Cys Pro Ala Pro Glu Phe Leu
    530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Glu Val Gln Phe Asn Trp Tyr Val Asp Gly Val Glu
            580                 585                 590

Val His Asn Ala Lys Thr Lys Pro Arg Glu Glu Gln Phe Asn Ser Thr
        595                 600                 605

Tyr Arg Val Val Ser Val Leu Thr Val Leu His Gln Asp Trp Leu Asn
    610                 615                 620

Gly Lys Glu Tyr Lys Cys Lys Val Ser Asn Lys Gly Leu Pro Ser Ser
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Gln Glu Glu Met Thr Lys Asn Gln Val
            660                 665                 670

Ser Leu Thr Cys Leu Val Lys Gly Phe Tyr Pro Ser Asp Ile Ala Val
        675                 680                 685

Glu Trp Glu Ser Asn Gly Gln Pro Glu Asn Asn Tyr Lys Thr Thr Pro
    690                 695                 700

Pro Val Leu Asp Ser Asp Gly Ser Phe Phe Leu Tyr Ser Arg Leu Thr
705                 710                 715                 720

Val Asp Lys Ser Arg Trp Gln Glu Gly Asn Val Phe Ser Cys Ser Val
                725                 730                 735

Met His Glu Ala Leu His Asn His Tyr Thr Gln Lys Ser Leu Ser Leu
            740                 745                 750

Ser Leu Gly Lys
```

755

<210> SEQ ID NO 7
<211> LENGTH: 756
<212> TYPE: PRT
<213> ORGANISM: Artificial Sequence
<220> FEATURE:
<223> OTHER INFORMATION: modified human EphA4-Fc synthetic polypeptide

<400> SEQUENCE: 7

```
Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255

Cys Lys Ile Gly Tyr Tyr Lys Ala Leu Ser Thr Asp Ala Thr Cys Ala
            260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
    290                 295                 300

Pro Cys Thr Arg Pro Pro Ser Ala Pro Leu Asn Leu Ile Ser Asn Val
305                 310                 315                 320

Gln Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
```

```
                    355                 360                 365
Pro Gln Gln Asn Gly Leu Lys Thr Thr Lys Val Ser Ile Thr Asp Leu
    370                 375                 380

Leu Ala His Thr Gln Tyr Thr Phe Glu Ile Trp Ala Val Asn Gly Val
385                 390                 395                 400

Ser Lys Tyr Asn Pro Asn Pro Asp Gln Ser Val Ser Val Thr Val Thr
                405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
    450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Glu
        515                 520                 525

Ser Lys Tyr Gly Pro Pro Cys Pro Pro Cys Pro Ala Pro Glu Phe Leu
    530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Glu Val Gln Phe Asn Trp Tyr Val Asp Gly Val Glu
            580                 585                 590

Val His Asn Ala Lys Thr Lys Pro Arg Glu Glu Gln Phe Asn Ser Thr
        595                 600                 605

Tyr Arg Val Val Ser Val Leu Thr Val Leu His Gln Asp Trp Leu Asn
    610                 615                 620

Gly Lys Glu Tyr Lys Cys Lys Val Ser Asn Lys Gly Leu Pro Ser Ser
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Gln Glu Glu Met Thr Lys Asn Gln Val
            660                 665                 670

Ser Leu Thr Cys Leu Val Lys Gly Phe Tyr Pro Ser Asp Ile Ala Val
        675                 680                 685

Glu Trp Glu Ser Asn Gly Gln Pro Glu Asn Asn Tyr Lys Thr Thr Pro
    690                 695                 700

Pro Val Leu Asp Ser Asp Gly Ser Phe Phe Leu Tyr Ser Arg Leu Thr
705                 710                 715                 720

Val Asp Lys Ser Arg Trp Gln Glu Gly Asn Val Phe Ser Cys Ser Val
                725                 730                 735

Met His Glu Ala Leu His Asn His Tyr Thr Gln Lys Ser Leu Ser Leu
            740                 745                 750

Ser Leu Gly Lys
        755

<210> SEQ ID NO 8
```

<211> LENGTH: 756
<212> TYPE: PRT
<213> ORGANISM: Artificial Sequence
<220> FEATURE:
<223> OTHER INFORMATION: modified human EphA4-Fc synthetic polypeptide

<400> SEQUENCE: 8

```
Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Gln Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255

Cys Lys Ile Gly Tyr Tyr Lys Ala Leu Ser Thr Asp Ala Thr Cys Ala
            260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
    290                 295                 300

Pro Cys Thr Arg Pro Pro Ser Ala Pro Leu Asn Leu Ile Ser Asn Val
305                 310                 315                 320

Gln Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
        355                 360                 365

Pro Gln Gln Asn Gly Leu Lys Thr Thr Lys Val Ser Ile Thr Asp Leu
    370                 375                 380
```

Leu Ala His Thr Gln Tyr Thr Phe Glu Ile Trp Ala Val Asn Gly Val
385                 390                 395                 400

Ser Lys Tyr Asn Pro Asn Pro Asp Gln Ser Val Ser Val Thr Val Thr
            405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
    450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Glu
            515                 520                 525

Ser Lys Tyr Gly Pro Pro Cys Pro Pro Cys Pro Ala Pro Glu Phe Leu
530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Glu Val Gln Phe Asn Trp Tyr Val Asp Gly Val Glu
            580                 585                 590

Val His Asn Ala Lys Thr Lys Pro Arg Glu Glu Gln Phe Asn Ser Thr
    595                 600                 605

Tyr Arg Val Val Ser Val Leu Thr Val Leu His Gln Asp Trp Leu Asn
610                 615                 620

Gly Lys Glu Tyr Lys Cys Lys Val Ser Asn Lys Gly Leu Pro Ser Ser
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Gln Glu Glu Met Thr Lys Asn Gln Val
            660                 665                 670

Ser Leu Thr Cys Leu Val Lys Gly Phe Tyr Pro Ser Asp Ile Ala Val
        675                 680                 685

Glu Trp Glu Ser Asn Gly Gln Pro Glu Asn Asn Tyr Lys Thr Thr Pro
    690                 695                 700

Pro Val Leu Asp Ser Asp Gly Ser Phe Phe Leu Tyr Ser Arg Leu Thr
705                 710                 715                 720

Val Asp Lys Ser Arg Trp Gln Glu Gly Asn Val Phe Ser Cys Ser Val
                725                 730                 735

Met His Glu Ala Leu His Asn His Tyr Thr Gln Lys Ser Leu Ser Leu
            740                 745                 750

Ser Leu Gly Lys
        755

<210> SEQ ID NO 9
<211> LENGTH: 750
<212> TYPE: PRT
<213> ORGANISM: Artificial Sequence
<220> FEATURE:

<223> OTHER INFORMATION: unmodified murine-derived EphA4-Fc synthetic polypeptide

<400> SEQUENCE: 9

```
Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Ala Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Ser Gln Phe Gly Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Gln Asn Gly Glu Cys Gln Ala
                245                 250                 255

Cys Lys Ile Gly Tyr Tyr Lys Ala Leu Ser Thr Asp Ala Ser Cys Ala
            260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
    290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
        355                 360                 365

Pro Gln Gln Asn Gly Leu Lys Thr Thr Arg Val Ser Ile Thr Asp Leu
    370                 375                 380

Leu Ala His Thr Asn Tyr Thr Phe Glu Ile Trp Ala Val Asn Gly Val
385                 390                 395                 400
```

```
Ser Lys Tyr Asn Pro Ser Pro Asp Gln Ser Val Ser Val Thr Val Thr
            405                 410                 415

Thr Asn Gln Ala Ala Pro Ser Ser Ile Ala Leu Val Gln Ala Lys Glu
        420                 425                 430

Val Thr Arg Tyr Ser Val Ala Leu Ala Trp Leu Glu Pro Asp Arg Pro
            435                 440                 445

Asn Gly Val Ile Leu Glu Tyr Glu Val Lys Tyr Tyr Glu Lys Asp Gln
        450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Thr
        515                 520                 525

Gly Cys Lys Pro Cys Ile Cys Thr Val Pro Glu Val Ser Ser Val Phe
        530                 535                 540

Ile Phe Pro Pro Lys Pro Lys Asp Val Leu Thr Ile Thr Leu Thr Pro
545                 550                 555                 560

Lys Val Thr Cys Val Val Val Asp Ile Ser Lys Asp Asp Pro Glu Val
                565                 570                 575

Gln Phe Ser Trp Phe Val Asp Asp Val Glu Val His Thr Ala Gln Thr
            580                 585                 590

Gln Pro Arg Glu Glu Gln Phe Asn Ser Thr Phe Arg Ser Val Ser Glu
        595                 600                 605

Leu Pro Ile Met His Gln Asp Trp Leu Asn Gly Lys Glu Phe Lys Cys
610                 615                 620

Arg Val Asn Ser Ala Ala Phe Pro Ala Pro Ile Glu Lys Thr Ile Ser
625                 630                 635                 640

Lys Thr Lys Gly Arg Pro Lys Ala Pro Gln Val Tyr Thr Ile Pro Pro
                645                 650                 655

Pro Lys Glu Gln Met Ala Lys Asp Lys Val Ser Leu Thr Cys Met Ile
            660                 665                 670

Thr Asp Phe Phe Pro Glu Asp Ile Thr Val Glu Trp Gln Trp Asn Gly
        675                 680                 685

Gln Pro Ala Glu Asn Tyr Lys Asn Thr Gln Pro Ile Met Asp Thr Asp
        690                 695                 700

Gly Ser Tyr Phe Val Tyr Ser Lys Leu Asn Val Gln Lys Ser Asn Trp
705                 710                 715                 720

Glu Ala Gly Asn Thr Phe Thr Cys Ser Val Leu His Glu Gly Leu His
                725                 730                 735

Asn His His Thr Glu Lys Ser Leu Ser His Ser Pro Gly Lys
            740                 745                 750

<210> SEQ ID NO 10
<211> LENGTH: 750
<212> TYPE: PRT
<213> ORGANISM: Artificial Sequence
<220> FEATURE:
<223> OTHER INFORMATION: modified murine EphA4-Fc synthetic polypeptide

<400> SEQUENCE: 10

Val Thr Gly Ser Arg Val Tyr Pro Ala Asn Glu Val Thr Leu Leu Asp
1               5                   10                  15
```

```
Ser Arg Ser Val Gln Gly Glu Leu Gly Trp Ile Ala Ser Pro Leu Glu
         20                  25                  30

Gly Gly Trp Glu Glu Val Ser Ile Met Asp Glu Lys Asn Thr Pro Ile
         35                  40                  45

Arg Thr Tyr Gln Val Cys Asn Val Met Glu Ala Ser Gln Asn Asn Trp
50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                 85                  90                  95

Gly Thr Cys Lys Glu Thr Phe Asn Leu Tyr Tyr Glu Ser Asp Asn
             100                 105                 110

Asp Lys Glu Arg Phe Ile Arg Glu Ser Gln Phe Gly Lys Ile Asp Thr
                 115                 120                 125

Ile Ala Ala Asp Glu Ser Phe Thr Gln Val Asp Ile Gly Asp Arg Ile
130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                 165                 170                 175

Ser Val Arg Val Phe Tyr Lys Lys Cys Pro Leu Thr Val Arg Asn Leu
             180                 185                 190

Ala Gln Phe Pro Asp Thr Ile Thr Gly Ala Asp Thr Ser Ser Leu Val
             195                 200                 205

Glu Val Arg Gly Ser Cys Val Gln Asn Ser Glu Glu Lys Asp Val Pro
             210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Gln Asn Gly Glu Cys Gln Ala
                 245                 250                 255

Cys Lys Ile Gly Tyr Tyr Lys Ala Leu Ser Thr Asp Ala Ser Cys Ala
             260                 265                 270

Lys Cys Pro Pro His Ser Tyr Ser Val Trp Glu Gly Ala Thr Ser Cys
             275                 280                 285

Thr Cys Asp Arg Gly Phe Phe Arg Ala Asp Asn Asp Ala Ala Ser Met
290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                 325                 330                 335

Gly Arg Gln Asp Ile Ser Tyr Asn Val Val Cys Lys Lys Cys Gly Ala
             340                 345                 350

Gly Asp Pro Ser Lys Cys Arg Pro Cys Gly Ser Gly Val His Tyr Thr
             355                 360                 365

Pro Gln Gln Asn Gly Leu Lys Thr Thr Arg Val Ser Ile Thr Asp Leu
             370                 375                 380

Leu Ala His Thr Asn Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
                 405                 410                 415

Thr Asn Gln Ala Ala Pro Ser Ser Ile Ala Leu Val Gln Ala Lys Glu
             420                 425                 430
```

```
Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
                500                 505                 510

Thr Asn Thr Val Pro Ser Arg Ile Ile Gly Asp Gly Ala Asn Ser Thr
                515                 520                 525

Gly Cys Lys Pro Cys Ile Cys Thr Val Pro Glu Val Ser Ser Val Phe
530                 535                 540

Ile Phe Pro Pro Lys Pro Lys Asp Val Leu Thr Ile Thr Leu Thr Pro
545                 550                 555                 560

Lys Val Thr Cys Val Val Asp Ile Ser Lys Asp Asp Pro Glu Val
                565                 570                 575

Gln Phe Ser Trp Phe Val Asp Asp Val Glu Val His Thr Ala Gln Thr
                580                 585                 590

Gln Pro Arg Glu Glu Gln Phe Asn Ser Thr Phe Arg Ser Val Ser Glu
                595                 600                 605

Leu Pro Ile Met His Gln Asp Trp Leu Asn Gly Lys Glu Phe Lys Cys
                610                 615                 620

Arg Val Asn Ser Ala Ala Phe Pro Ala Pro Ile Glu Lys Thr Ile Ser
625                 630                 635                 640

Lys Thr Lys Gly Arg Pro Lys Ala Pro Gln Val Tyr Thr Ile Pro Pro
                645                 650                 655

Pro Lys Glu Gln Met Ala Lys Asp Lys Val Ser Leu Thr Cys Met Ile
                660                 665                 670

Thr Asp Phe Phe Pro Glu Asp Ile Thr Val Glu Trp Gln Trp Asn Gly
                675                 680                 685

Gln Pro Ala Glu Asn Tyr Lys Asn Thr Gln Pro Ile Met Asp Thr Asp
690                 695                 700

Gly Ser Tyr Phe Val Tyr Ser Lys Leu Asn Val Gln Lys Ser Asn Trp
705                 710                 715                 720

Glu Ala Gly Asn Thr Phe Thr Cys Ser Val Leu His Glu Gly Leu His
                725                 730                 735

Asn His Thr Glu Lys Ser Leu Ser His Ser Pro Gly Lys
                740                 745                 750

<210> SEQ ID NO 11
<211> LENGTH: 750
<212> TYPE: PRT
<213> ORGANISM: Artificial Sequence
<220> FEATURE:
<223> OTHER INFORMATION: modified murine EphA4-Fc synthetic polypeptide

<400> SEQUENCE: 11

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
                20                  25                  30

Gly Gly Trp Glu Glu Val Ser Ile Met Asp Glu Lys Asn Thr Pro Ile
                35                  40                  45
```

```
Arg Thr Tyr Gln Val Cys Asn Val Met Glu Ala Ser Gln Asn Asn Trp
     50                  55                  60
Leu Arg Thr Asp Trp Ile Thr Arg Glu Gly Ala Gln Arg Val Tyr Ile
 65                  70                  75                  80
Glu Ile Lys Phe Thr Leu Arg Asp Cys Asn Ser Leu Pro Gly Val Met
                 85                  90                  95
Gly Thr Cys Lys Glu Thr Phe Asn Leu Tyr Tyr Glu Ser Asp Asn
                100                 105                 110
Asp Lys Glu Arg Phe Ile Arg Glu Ser Gln Phe Gly Lys Ile Asp Thr
            115                 120                 125
Ile Ala Ala Asp Glu Ser Phe Thr Gln Val Asp Ile Gly Asp Arg Ile
130                 135                 140
Met Lys Leu Asn Thr Glu Ile Arg Asp Val Gly Pro Leu Ser Lys Lys
145                 150                 155                 160
Gly Phe Tyr Leu Ala Phe Gln Asp Val Gly Ala Cys Ile Ala Leu Val
                165                 170                 175
Ser Val Arg Val Phe Tyr Lys Lys Cys Pro Leu Thr Val Arg Asn Leu
            180                 185                 190
Ala Gln Phe Pro Asp Thr Ile Thr Gly Ala Asp Thr Ser Ser Leu Val
        195                 200                 205
Glu Val Arg Gly Ser Cys Val Asn Asn Ser Glu Glu Lys Asp Val Pro
210                 215                 220
Lys Met Tyr Cys Gly Ala Asp Gly Glu Trp Leu Val Pro Ile Gly Asn
225                 230                 235                 240
Cys Leu Cys Asn Ala Gly His Glu Glu Gln Asn Gly Glu Cys Gln Ala
                245                 250                 255
Cys Lys Ile Gly Tyr Tyr Lys Ala Leu Ser Thr Asp Ala Ser Cys Ala
            260                 265                 270
Lys Cys Pro Pro His Ser Tyr Ser Val Trp Glu Gly Ala Thr Ser Cys
        275                 280                 285
Thr Cys Asp Arg Gly Phe Phe Arg Ala Asp Asn Asp Ala Ala Ser Met
    290                 295                 300
Pro Cys Thr Arg Pro Pro Ser Ala Pro Leu Asn Leu Ile Ser Asn Val
305                 310                 315                 320
Gln Glu Thr Ser Val Asn Leu Glu Trp Ser Ser Pro Gln Asn Thr Gly
                325                 330                 335
Gly Arg Gln Asp Ile Ser Tyr Asn Val Val Cys Lys Lys Cys Gly Ala
            340                 345                 350
Gly Asp Pro Ser Lys Cys Arg Pro Cys Gly Ser Gly Val His Tyr Thr
        355                 360                 365
Pro Gln Gln Asn Gly Leu Lys Thr Thr Arg Val Ser Ile Thr Asp Leu
    370                 375                 380
Leu Ala His Thr Asn Tyr Thr Phe Glu Ile Trp Ala Val Asn Gly Val
385                 390                 395                 400
Ser Lys Tyr Asn Pro Ser Pro Asp Gln Ser Val Ser Val Thr Val Thr
                405                 410                 415
Thr Asn Gln Ala Ala Pro Ser Ser Ile Ala Leu Val Gln Ala Lys Glu
            420                 425                 430
Val Thr Arg Tyr Ser Val Ala Leu Ala Trp Leu Glu Pro Asp Arg Pro
        435                 440                 445
Asn Gly Val Ile Leu Glu Tyr Glu Val Lys Tyr Tyr Glu Lys Asp Gln
450                 455                 460
Asn Glu Arg Ser Tyr Arg Ile Val Arg Thr Ala Ala Arg Asn Thr Asp
```

```
                465                 470                 475                 480
        Ile Lys Gly Leu Asn Pro Leu Thr Ser Tyr Val Phe His Val Arg Ala
                        485                 490                 495

Arg Thr Ala Ala Gly Tyr Gly Asp Phe Ser Glu Pro Leu Glu Val Thr
                        500                 505                 510

Thr Asn Thr Val Pro Ser Arg Ile Ile Gly Asp Gly Ala Asn Ser Thr
                        515                 520                 525

Gly Cys Lys Pro Cys Ile Cys Thr Val Pro Glu Val Ser Ser Val Phe
                        530                 535                 540

Ile Phe Pro Pro Lys Pro Lys Asp Val Leu Thr Ile Thr Leu Thr Pro
        545                 550                 555                 560

Lys Val Thr Cys Val Val Val Asp Ile Ser Lys Asp Asp Pro Glu Val
                        565                 570                 575

Gln Phe Ser Trp Phe Val Asp Asp Val Glu Val His Thr Ala Gln Thr
                        580                 585                 590

Gln Pro Arg Glu Glu Gln Phe Asn Ser Thr Phe Arg Ser Val Ser Glu
                        595                 600                 605

Leu Pro Ile Met His Gln Asp Trp Leu Asn Gly Lys Glu Phe Lys Cys
                        610                 615                 620

Arg Val Asn Ser Ala Ala Phe Pro Ala Pro Ile Glu Lys Thr Ile Ser
        625                 630                 635                 640

Lys Thr Lys Gly Arg Pro Lys Ala Pro Gln Val Tyr Thr Ile Pro Pro
                        645                 650                 655

Pro Lys Glu Gln Met Ala Lys Asp Lys Val Ser Leu Thr Cys Met Ile
                        660                 665                 670

Thr Asp Phe Phe Pro Glu Asp Ile Thr Val Glu Trp Gln Trp Asn Gly
                        675                 680                 685

Gln Pro Ala Glu Asn Tyr Lys Asn Thr Gln Pro Ile Met Asp Thr Asp
                        690                 695                 700

Gly Ser Tyr Phe Val Tyr Ser Lys Leu Asn Val Gln Lys Ser Asn Trp
        705                 710                 715                 720

Glu Ala Gly Asn Thr Phe Thr Cys Ser Val Leu His Glu Gly Leu His
                        725                 730                 735

Asn His His Thr Glu Lys Ser Leu Ser His Ser Pro Gly Lys
                        740                 745                 750

<210> SEQ ID NO 12
<211> LENGTH: 750
<212> TYPE: PRT
<213> ORGANISM: Artificial Sequence
<220> FEATURE:
<223> OTHER INFORMATION: modified murine EphA4-Fc synthetic polypeptide

<400> SEQUENCE: 12

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
                20                  25                  30

Gly Gly Trp Glu Glu Val Ser Ile Met Asp Glu Lys Asn Thr Pro Ile
            35                  40                  45

Arg Thr Tyr Gln Val Cys Asn Val Met Glu Ala Ser Gln Asn Asn Trp
        50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
```

```
                    85                  90                  95
Gly Thr Cys Lys Glu Thr Phe Asn Leu Tyr Tyr Glu Ser Asp Asn
                100                 105                 110

Asp Lys Glu Arg Phe Ile Arg Glu Ser Gln Phe Gly Lys Ile Asp Thr
            115                 120                 125

Ile Ala Ala Asp Glu Ser Phe Thr Gln Val Asp Ile Gly Asp Arg Ile
            130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
            195                 200                 205

Glu Val Arg Gly Ser Cys Val Asn Asn Ser Glu Glu Lys Asp Val Pro
210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Gln Asn Gly Glu Cys Gln Ala
                245                 250                 255

Cys Lys Ile Gly Tyr Tyr Lys Ala Leu Ser Thr Asp Ala Ser Cys Ala
            260                 265                 270

Lys Cys Pro Pro His Ser Tyr Ser Val Trp Glu Gly Ala Thr Ser Cys
            275                 280                 285

Thr Cys Asp Arg Gly Phe Phe Arg Ala Asp Asn Asp Ala Ala Ser Met
            290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
            355                 360                 365

Pro Gln Gln Asn Gly Leu Lys Thr Thr Arg Val Ser Ile Thr Asp Leu
            370                 375                 380

Leu Ala His Thr Gln Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
                405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
            435                 440                 445

Asn Gly Val Ile Leu Glu Tyr Glu Val Lys Tyr Tyr Glu Lys Asp Gln
            450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510
```

```
Thr Asn Thr Val Pro Ser Arg Ile Ile Gly Asp Gly Ala Asn Ser Thr
            515                 520                 525

Gly Cys Lys Pro Cys Ile Cys Thr Val Pro Glu Val Ser Ser Val Phe
        530                 535                 540

Ile Phe Pro Pro Lys Pro Lys Asp Val Leu Thr Ile Thr Leu Thr Pro
545                 550                 555                 560

Lys Val Thr Cys Val Val Val Asp Ile Ser Lys Asp Asp Pro Glu Val
                565                 570                 575

Gln Phe Ser Trp Phe Val Asp Asp Val Glu Val His Thr Ala Gln Thr
            580                 585                 590

Gln Pro Arg Glu Glu Gln Phe Asn Ser Thr Phe Arg Ser Val Ser Glu
        595                 600                 605

Leu Pro Ile Met His Gln Asp Trp Leu Asn Gly Lys Glu Phe Lys Cys
    610                 615                 620

Arg Val Asn Ser Ala Ala Phe Pro Ala Pro Ile Glu Lys Thr Ile Ser
625                 630                 635                 640

Lys Thr Lys Gly Arg Pro Lys Ala Pro Gln Val Tyr Thr Ile Pro Pro
                645                 650                 655

Pro Lys Glu Gln Met Ala Lys Asp Lys Val Ser Leu Thr Cys Met Ile
            660                 665                 670

Thr Asp Phe Phe Pro Glu Asp Ile Thr Val Glu Trp Gln Trp Asn Gly
        675                 680                 685

Gln Pro Ala Glu Asn Tyr Lys Asn Thr Gln Pro Ile Met Asp Thr Asp
    690                 695                 700

Gly Ser Tyr Phe Val Tyr Ser Lys Leu Asn Val Gln Lys Ser Asn Trp
705                 710                 715                 720

Glu Ala Gly Asn Thr Phe Thr Cys Ser Val Leu His Glu Gly Leu His
                725                 730                 735

Asn His His Thr Glu Lys Ser Leu Ser His Ser Pro Gly Lys
            740                 745                 750

<210> SEQ ID NO 13
<211> LENGTH: 750
<212> TYPE: PRT
<213> ORGANISM: Artificial Sequence
<220> FEATURE:
<223> OTHER INFORMATION: modified murine EphA4-Fc synthetic polypeptide

<400> SEQUENCE: 13

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Ala Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Ser Gln Phe Gly Lys Ile Asp Thr
        115                 120                 125
```

```
Ile Ala Ala Asp Glu Ser Phe Thr Gln Val Asp Ile Gly Asp Arg Ile
130                 135                 140
Met Lys Leu Asn Thr Glu Ile Arg Asp Val Gly Pro Leu Ser Lys Lys
145                 150                 155                 160
Gly Phe Tyr Leu Ala Phe Gln Asp Val Gly Ala Cys Ile Ala Leu Val
                165                 170                 175
Ser Val Arg Val Phe Tyr Lys Lys Cys Pro Leu Thr Val Arg Asn Leu
            180                 185                 190
Ala Gln Phe Pro Asp Thr Ile Thr Gly Ala Asp Thr Ser Ser Leu Val
        195                 200                 205
Glu Val Arg Gly Ser Cys Val Gln Asn Ser Glu Glu Lys Asp Val Pro
210                 215                 220
Lys Met Tyr Cys Gly Ala Asp Gly Glu Trp Leu Val Pro Ile Gly Asn
225                 230                 235                 240
Cys Leu Cys Asn Ala Gly His Glu Gln Asn Gly Glu Cys Gln Ala
                245                 250                 255
Cys Lys Ile Gly Tyr Tyr Lys Ala Leu Ser Thr Asp Ala Ser Cys Ala
            260                 265                 270
Lys Cys Pro Pro His Ser Tyr Ser Val Trp Glu Gly Ala Thr Ser Cys
        275                 280                 285
Thr Cys Asp Arg Gly Phe Phe Arg Ala Asp Asn Asp Ala Ala Ser Met
    290                 295                 300
Pro Cys Thr Arg Pro Pro Ser Ala Pro Leu Asn Leu Ile Ser Asn Val
305                 310                 315                 320
Gln Glu Thr Ser Val Asn Leu Glu Trp Ser Ser Pro Gln Asn Thr Gly
                325                 330                 335
Gly Arg Gln Asp Ile Ser Tyr Asn Val Val Cys Lys Lys Cys Gly Ala
            340                 345                 350
Gly Asp Pro Ser Lys Cys Arg Pro Cys Gly Ser Gly Val His Tyr Thr
        355                 360                 365
Pro Gln Gln Asn Gly Leu Lys Thr Thr Arg Val Ser Ile Thr Asp Leu
    370                 375                 380
Leu Ala His Thr Asn Tyr Thr Phe Glu Ile Trp Ala Val Asn Gly Val
385                 390                 395                 400
Ser Lys Tyr Asn Pro Ser Pro Asp Gln Ser Val Ser Val Thr Val Thr
                405                 410                 415
Thr Asn Gln Ala Ala Pro Ser Ser Ile Ala Leu Val Gln Ala Lys Glu
            420                 425                 430
Val Thr Arg Tyr Ser Val Ala Leu Ala Trp Leu Glu Pro Asp Arg Pro
        435                 440                 445
Asn Gly Val Ile Leu Glu Tyr Glu Val Lys Tyr Tyr Glu Lys Asp Gln
    450                 455                 460
Asn Glu Arg Ser Tyr Arg Ile Val Arg Thr Ala Ala Arg Asn Thr Asp
465                 470                 475                 480
Ile Lys Gly Leu Asn Pro Leu Thr Ser Tyr Val Phe His Val Arg Ala
                485                 490                 495
Arg Thr Ala Ala Gly Tyr Gly Asp Phe Ser Glu Pro Leu Glu Val Thr
            500                 505                 510
Thr Asn Thr Val Pro Ser Arg Ile Ile Gly Asp Gly Ala Asn Ser Thr
        515                 520                 525
Gly Cys Lys Pro Cys Ile Cys Thr Val Pro Glu Val Ser Ser Val Phe
    530                 535                 540
```

```
Ile Phe Pro Pro Lys Pro Lys Asp Val Leu Thr Ile Thr Leu Thr Pro
545                 550                 555                 560

Lys Val Thr Cys Val Val Val Asp Ile Ser Lys Asp Asp Pro Glu Val
            565                 570                 575

Gln Phe Ser Trp Phe Val Asp Asp Val Glu Val His Thr Ala Gln Thr
        580                 585                 590

Gln Pro Arg Glu Glu Gln Phe Asn Ser Thr Phe Arg Ser Val Ser Glu
    595                 600                 605

Leu Pro Ile Met His Gln Asp Trp Leu Asn Gly Lys Glu Phe Lys Cys
610                 615                 620

Arg Val Asn Ser Ala Ala Phe Pro Ala Pro Ile Glu Lys Thr Ile Ser
625                 630                 635                 640

Lys Thr Lys Gly Arg Pro Lys Ala Pro Gln Val Tyr Thr Ile Pro Pro
            645                 650                 655

Pro Lys Glu Gln Met Ala Lys Asp Lys Val Ser Leu Thr Cys Met Ile
        660                 665                 670

Thr Asp Phe Phe Pro Glu Asp Ile Thr Val Glu Trp Gln Trp Asn Gly
    675                 680                 685

Gln Pro Ala Glu Asn Tyr Lys Asn Thr Gln Pro Ile Met Asp Thr Asp
690                 695                 700

Gly Ser Tyr Phe Val Tyr Ser Lys Leu Asn Val Gln Lys Ser Asn Trp
705                 710                 715                 720

Glu Ala Gly Asn Thr Phe Thr Cys Ser Val Leu His Glu Gly Leu His
            725                 730                 735

Asn His His Thr Glu Lys Ser Leu Ser His Ser Pro Gly Lys
        740                 745                 750

<210> SEQ ID NO 14
<211> LENGTH: 750
<212> TYPE: PRT
<213> ORGANISM: Artificial Sequence
<220> FEATURE:
<223> OTHER INFORMATION: modified murine EphA4-Fc synthetic polypeptide

<400> SEQUENCE: 14

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Ala Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
            85                  90                  95

Gly Thr Cys Lys Glu Thr Phe Asn Leu Tyr Tyr Tyr Glu Ser Asp Asn
        100                 105                 110

Asp Lys Glu Arg Phe Ile Arg Glu Ser Gln Phe Gly Lys Ile Asp Thr
    115                 120                 125

Ile Ala Ala Asp Glu Ser Phe Thr Gln Val Asp Ile Gly Asp Arg Ile
130                 135                 140

Met Lys Leu Asn Thr Glu Ile Arg Asp Val Gly Pro Leu Ser Lys Lys
145                 150                 155                 160
```

```
Gly Phe Tyr Leu Ala Phe Gln Asp Val Gly Ala Cys Ile Ala Leu Val
            165                 170                 175

Ser Val Arg Val Phe Tyr Lys Lys Cys Pro Leu Thr Val Arg Asn Leu
        180                 185                 190

Ala Gln Phe Pro Asp Thr Ile Thr Gly Ala Asp Thr Ser Ser Leu Val
        195                 200                 205

Glu Val Arg Gly Ser Cys Val Gln Asn Ser Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Gln Asn Gly Glu Cys Gln Ala
            245                 250                 255

Cys Lys Ile Gly Tyr Tyr Lys Ala Leu Ser Thr Asp Ala Ser Cys Ala
        260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
    290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
            325                 330                 335

Gly Arg Gln Asp Ile Ser Tyr Asn Val Val Cys Lys Lys Cys Gly Ala
        340                 345                 350

Gly Asp Pro Ser Lys Cys Arg Pro Cys Gly Ser Gly Val His Tyr Thr
        355                 360                 365

Pro Gln Gln Asn Gly Leu Lys Thr Thr Arg Val Ser Ile Thr Asp Leu
    370                 375                 380

Leu Ala His Thr Gln Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
            405                 410                 415

Thr Asn Gln Ala Ala Pro Ser Ser Ile Ala Leu Val Gln Ala Lys Glu
        420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
    450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
            485                 490                 495

Arg Thr Ala Ala Gly Tyr Gly Asp Phe Ser Glu Pro Leu Glu Val Thr
        500                 505                 510

Thr Asn Thr Val Pro Ser Arg Ile Ile Gly Asp Gly Ala Asn Ser Thr
        515                 520                 525

Gly Cys Lys Pro Cys Ile Cys Thr Val Pro Glu Val Ser Ser Val Phe
    530                 535                 540

Ile Phe Pro Pro Lys Pro Lys Asp Val Leu Thr Ile Thr Leu Thr Pro
545                 550                 555                 560

Lys Val Thr Cys Val Val Val Asp Ile Ser Lys Asp Asp Pro Glu Val
            565                 570                 575

Gln Phe Ser Trp Phe Val Asp Asp Val Glu Val His Thr Ala Gln Thr
```

```
                    580                 585                 590
Gln Pro Arg Glu Glu Gln Phe Asn Ser Thr Phe Arg Ser Val Ser Glu
                595                 600                 605

Leu Pro Ile Met His Gln Asp Trp Leu Asn Gly Lys Glu Phe Lys Cys
            610                 615                 620

Arg Val Asn Ser Ala Ala Phe Pro Ala Pro Ile Glu Lys Thr Ile Ser
625                 630                 635                 640

Lys Thr Lys Gly Arg Pro Lys Ala Pro Gln Val Tyr Thr Ile Pro Pro
                645                 650                 655

Pro Lys Glu Gln Met Ala Lys Asp Lys Val Ser Leu Thr Cys Met Ile
            660                 665                 670

Thr Asp Phe Phe Pro Glu Asp Ile Thr Val Glu Trp Gln Trp Asn Gly
        675                 680                 685

Gln Pro Ala Glu Asn Tyr Lys Asn Thr Gln Pro Ile Met Asp Thr Asp
            690                 695                 700

Gly Ser Tyr Phe Val Tyr Ser Lys Leu Asn Val Gln Lys Ser Asn Trp
705                 710                 715                 720

Glu Ala Gly Asn Thr Phe Thr Cys Ser Val Leu His Glu Gly Leu His
                725                 730                 735

Asn His His Thr Glu Lys Ser Leu Ser His Ser Pro Gly Lys
            740                 745                 750

<210> SEQ ID NO 15
<211> LENGTH: 750
<212> TYPE: PRT
<213> ORGANISM: Artificial Sequence
<220> FEATURE:
<223> OTHER INFORMATION: modified murine EphA4-Fc synthetic polypeptide

<400> SEQUENCE: 15

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Ala Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Ser Gln Phe Gly Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
```

```
            195                 200                 205
Glu Val Arg Gly Ser Cys Val Asn Asn Ser Glu Glu Lys Asp Val Pro
210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Gln Asn Gly Glu Cys Gln Ala
                245                 250                 255

Cys Lys Ile Gly Tyr Tyr Lys Ala Leu Ser Thr Asp Ala Ser Cys Ala
                260                 265                 270

Lys Cys Pro Pro His Ser Tyr Ser Val Trp Glu Gly Ala Thr Ser Cys
            275                 280                 285

Thr Cys Asp Arg Gly Phe Phe Arg Ala Asp Asn Asp Ala Ala Ser Met
290                 295                 300

Pro Cys Thr Arg Pro Pro Ser Ala Pro Leu Asn Leu Ile Ser Asn Val
305                 310                 315                 320

Gln Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
                340                 345                 350

Gly Asp Pro Ser Lys Cys Arg Pro Cys Gly Ser Gly Val His Tyr Thr
            355                 360                 365

Pro Gln Gln Asn Gly Leu Lys Thr Thr Arg Val Ser Ile Thr Asp Leu
370                 375                 380

Leu Ala His Thr Gln Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
                405                 410                 415

Thr Asn Gln Ala Ala Pro Ser Ser Ile Ala Leu Val Gln Ala Lys Glu
                420                 425                 430

Val Thr Arg Tyr Ser Val Ala Leu Ala Trp Leu Glu Pro Asp Arg Pro
            435                 440                 445

Asn Gly Val Ile Leu Glu Tyr Glu Val Lys Tyr Tyr Glu Lys Asp Gln
450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
                500                 505                 510

Thr Asn Thr Val Pro Ser Arg Ile Ile Gly Asp Gly Ala Asn Ser Thr
            515                 520                 525

Gly Cys Lys Pro Cys Ile Cys Thr Val Pro Glu Val Ser Ser Val Phe
530                 535                 540

Ile Phe Pro Pro Lys Pro Lys Asp Val Leu Thr Ile Thr Leu Thr Pro
545                 550                 555                 560

Lys Val Thr Cys Val Val Val Asp Ile Ser Lys Asp Asp Pro Glu Val
                565                 570                 575

Gln Phe Ser Trp Phe Val Asp Asp Val Glu Val His Thr Ala Gln Thr
                580                 585                 590

Gln Pro Arg Glu Glu Gln Phe Asn Ser Thr Phe Arg Ser Val Ser Glu
            595                 600                 605

Leu Pro Ile Met His Gln Asp Trp Leu Asn Gly Lys Glu Phe Lys Cys
610                 615                 620
```

```
Arg Val Asn Ser Ala Ala Phe Pro Ala Pro Ile Glu Lys Thr Ile Ser
625                 630                 635                 640

Lys Thr Lys Gly Arg Pro Lys Ala Pro Gln Val Tyr Thr Ile Pro Pro
            645                 650                 655

Pro Lys Glu Gln Met Ala Lys Asp Lys Val Ser Leu Thr Cys Met Ile
            660                 665                 670

Thr Asp Phe Phe Pro Glu Asp Ile Thr Val Glu Trp Gln Trp Asn Gly
        675                 680                 685

Gln Pro Ala Glu Asn Tyr Lys Asn Thr Gln Pro Ile Met Asp Thr Asp
    690                 695                 700

Gly Ser Tyr Phe Val Tyr Ser Lys Leu Asn Val Gln Lys Ser Asn Trp
705                 710                 715                 720

Glu Ala Gly Asn Thr Phe Thr Cys Ser Val Leu His Glu Gly Leu His
                725                 730                 735

Asn His His Thr Glu Lys Ser Leu Ser His Ser Pro Gly Lys
            740                 745                 750

<210> SEQ ID NO 16
<211> LENGTH: 750
<212> TYPE: PRT
<213> ORGANISM: Artificial Sequence
<220> FEATURE:
<223> OTHER INFORMATION: modified murine EphA4-Fc synthetic polypeptide

<400> SEQUENCE: 16

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
                20                  25                  30

Gly Gly Trp Glu Glu Val Ser Ile Met Asp Glu Lys Asn Thr Pro Ile
            35                  40                  45

Arg Thr Tyr Gln Val Cys Asn Val Met Glu Ala Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Ser Gln Phe Gly Lys Ile Asp Thr
    115                 120                 125

Ile Ala Ala Asp Glu Ser Phe Thr Gln Val Asp Ile Gly Asp Arg Ile
130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
    195                 200                 205

Glu Val Arg Gly Ser Cys Val Gln Asn Ser Glu Glu Lys Asp Val Pro
210                 215                 220

Lys Met Tyr Cys Gly Ala Asp Gly Glu Trp Leu Val Pro Ile Gly Asn
225                 230                 235                 240
```

-continued

```
Cys Leu Cys Asn Ala Gly His Glu Glu Gln Asn Gly Glu Cys Gln Ala
            245                 250                 255
Cys Lys Ile Gly Tyr Tyr Lys Ala Leu Ser Thr Asp Ala Ser Cys Ala
            260                 265                 270
Lys Cys Pro Pro His Ser Tyr Ser Val Trp Glu Gly Ala Thr Ser Cys
            275                 280                 285
Thr Cys Asp Arg Gly Phe Phe Arg Ala Asp Asn Asp Ala Ala Ser Met
            290                 295                 300
Pro Cys Thr Arg Pro Pro Ser Ala Pro Leu Asn Leu Ile Ser Asn Val
305                 310                 315                 320
Gln Glu Thr Ser Val Asn Leu Glu Trp Ser Ser Pro Gln Asn Thr Gly
                325                 330                 335
Gly Arg Gln Asp Ile Ser Tyr Asn Val Val Cys Lys Lys Cys Gly Ala
                340                 345                 350
Gly Asp Pro Ser Lys Cys Arg Pro Cys Gly Ser Gly Val His Tyr Thr
            355                 360                 365
Pro Gln Gln Asn Gly Leu Lys Thr Thr Arg Val Ser Ile Thr Asp Leu
            370                 375                 380
Leu Ala His Thr Gln Tyr Thr Phe Glu Ile Trp Ala Val Asn Gly Val
385                 390                 395                 400
Ser Lys Tyr Asn Pro Ser Pro Asp Gln Ser Val Ser Val Thr Val Thr
                405                 410                 415
Thr Asn Gln Ala Ala Pro Ser Ser Ile Ala Leu Val Gln Ala Lys Glu
            420                 425                 430
Val Thr Arg Tyr Ser Val Ala Leu Ala Trp Leu Glu Pro Asp Arg Pro
            435                 440                 445
Asn Gly Val Ile Leu Glu Tyr Glu Val Lys Tyr Tyr Glu Lys Asp Gln
450                 455                 460
Asn Glu Arg Ser Tyr Arg Ile Val Arg Thr Ala Ala Arg Asn Thr Asp
465                 470                 475                 480
Ile Lys Gly Leu Asn Pro Leu Thr Ser Tyr Val Phe His Val Arg Ala
                485                 490                 495
Arg Thr Ala Ala Gly Tyr Gly Asp Phe Ser Glu Pro Leu Glu Val Thr
            500                 505                 510
Thr Asn Thr Val Pro Ser Arg Ile Ile Gly Asp Gly Ala Asn Ser Thr
            515                 520                 525
Gly Cys Lys Pro Cys Ile Cys Thr Val Pro Glu Val Ser Ser Val Phe
            530                 535                 540
Ile Phe Pro Pro Lys Pro Lys Asp Val Leu Thr Ile Thr Leu Thr Pro
545                 550                 555                 560
Lys Val Thr Cys Val Val Val Asp Ile Ser Lys Asp Asp Pro Glu Val
                565                 570                 575
Gln Phe Ser Trp Phe Val Asp Asp Val Glu Val His Thr Ala Gln Thr
            580                 585                 590
Gln Pro Arg Glu Glu Gln Phe Asn Ser Thr Phe Arg Ser Val Ser Glu
            595                 600                 605
Leu Pro Ile Met His Gln Asp Trp Leu Asn Gly Lys Glu Phe Lys Cys
            610                 615                 620
Arg Val Asn Ser Ala Ala Phe Pro Ala Pro Ile Glu Lys Thr Ile Ser
625                 630                 635                 640
Lys Thr Lys Gly Arg Pro Lys Ala Pro Gln Val Tyr Thr Ile Pro Pro
                645                 650                 655
```

```
Pro Lys Glu Gln Met Ala Lys Asp Lys Val Ser Leu Thr Cys Met Ile
            660                 665                 670

Thr Asp Phe Phe Pro Glu Asp Ile Thr Val Glu Trp Gln Trp Asn Gly
            675                 680                 685

Gln Pro Ala Glu Asn Tyr Lys Asn Thr Gln Pro Ile Met Asp Thr Asp
            690                 695                 700

Gly Ser Tyr Phe Val Tyr Ser Lys Leu Asn Val Gln Lys Ser Asn Trp
705                 710                 715                 720

Glu Ala Gly Asn Thr Phe Thr Cys Ser Val Leu His Glu Gly Leu His
                725                 730                 735

Asn His His Thr Glu Lys Ser Leu Ser His Ser Pro Gly Lys
            740                 745                 750
```

<210> SEQ ID NO 17
<211> LENGTH: 26
<212> TYPE: DNA
<213> ORGANISM: Artificial Sequence
<220> FEATURE:
<223> OTHER INFORMATION: sense primer

<400> SEQUENCE: 17
gcagctgcgt gcaaaacagc gaagag                                26

<210> SEQ ID NO 18
<211> LENGTH: 26
<212> TYPE: DNA
<213> ORGANISM: Artificial Sequence
<220> FEATURE:
<223> OTHER INFORMATION: antisense primer

<400> SEQUENCE: 18
ctcttcgctg ttttgcacgc agctgc                                26

<210> SEQ ID NO 19
<211> LENGTH: 27
<212> TYPE: DNA
<213> ORGANISM: Artificial Sequence
<220> FEATURE:
<223> OTHER INFORMATION: sense primer

<400> SEQUENCE: 19
atcagcaacg tgcaagagac aagcgtg                               27

<210> SEQ ID NO 20
<211> LENGTH: 27
<212> TYPE: DNA
<213> ORGANISM: Artificial Sequence
<220> FEATURE:
<223> OTHER INFORMATION: antisense primer

<400> SEQUENCE: 20
cacgcttgtc tcttgcacgt tgctgat                               27

<210> SEQ ID NO 21
<211> LENGTH: 27
<212> TYPE: DNA
<213> ORGANISM: Artificial Sequence
<220> FEATURE:
<223> OTHER INFORMATION: sense primer

<400> SEQUENCE: 21
ctggcccaca cccaatacac cttcgag                               27

```
<210> SEQ ID NO 22
<211> LENGTH: 27
<212> TYPE: DNA
<213> ORGANISM: Artificial Sequence
<220> FEATURE:
<223> OTHER INFORMATION: antisense primer

<400> SEQUENCE: 22
ctcgaaggtg tattgggtgt gggccag                                27

<210> SEQ ID NO 23
<211> LENGTH: 33
<212> TYPE: DNA
<213> ORGANISM: Artificial Sequence
<220> FEATURE:
<223> OTHER INFORMATION: sense primer

<400> SEQUENCE: 23 aggggggtcct gcgtgcagaa cagtgaagaa aag                        33

<210> SEQ ID NO 24
<211> LENGTH: 33
<212> TYPE: DNA
<213> ORGANISM: Artificial Sequence
<220> FEATURE:
<223> OTHER INFORMATION: antisense primer

<400> SEQUENCE: 24
cttttcttca ctgttctgca cgcaggaccc cct                         33

<210> SEQ ID NO 25
<211> LENGTH: 29
<212> TYPE: DNA
<213> ORGANISM: Artificial Sequence
<220> FEATURE:
<223> OTHER INFORMATION: sense primer

<400> SEQUENCE: 25
gatctccaac gtgccaggag acttctgtg                              29

<210> SEQ ID NO 26
<211> LENGTH: 28
<212> TYPE: DNA
<213> ORGANISM: Artificial Sequence
<220> FEATURE:
<223> OTHER INFORMATION: antisense primer

<400> SEQUENCE: 26
cacagaagtc tcctgcacgt tggagatc                               28

<210> SEQ ID NO 27
<211> LENGTH: 27
<212> TYPE: DNA
<213> ORGANISM: Artificial Sequence
<220> FEATURE:
<223> OTHER INFORMATION: sense primer

<400> SEQUENCE: 27
ctggcccaca cacagtacac cttcgag                                27

<210> SEQ ID NO 28
<211> LENGTH: 27
<212> TYPE: DNA
<213> ORGANISM: Artificial Sequence
<220> FEATURE:
<223> OTHER INFORMATION: antisense primer
```

<400> SEQUENCE: 28
ctcgaaggtg tactgtgtgt gggccag                                           27

<210> SEQ ID NO 29
<211> LENGTH: 540
<212> TYPE: PRT
<213> ORGANISM: Artificial Sequence
<220> FEATURE:
<223> OTHER INFORMATION: extracellular EphA2 synthetic polypeptide

<400> SEQUENCE: 29

```
Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350
```

Asp Ser Gly Gly Arg Glu Asp Ile Val Tyr Ser Val Thr Cys Glu Gln
            355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
                420                 425                 430

Ser Ile Asn Gln Thr Glu Pro Pro Lys Val Arg Leu Glu Gly Arg Ser
            435                 440                 445

Thr Thr Ser Leu Ser Val Ser Trp Ser Ile Pro Pro Pro Gln Gln Ser
        450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly
            530                 535                 540

<210> SEQ ID NO 30
<211> LENGTH: 541
<212> TYPE: PRT
<213> ORGANISM: Artificial Sequence
<220> FEATURE:
<223> OTHER INFORMATION: extracellular EphA3 synthetic polypeptide

<400> SEQUENCE: 30

Met Asp Cys Gln Leu Ser Ile Leu Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
        35                  40                  45

Ser His Gly Trp Glu Glu Ile Ser Gly Val Asp Glu His Tyr Thr Pro
    50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
        115                 120                 125

Asp Asp His Gly Val Lys Phe Arg Glu His Gln Phe Thr Lys Ile Asp
    130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Cys Pro Phe Thr Val Lys Asn
        195                 200                 205

Leu Ala Met Phe Pro Asp Thr Val Pro Met Asp Ser Gln Ser Leu Val
            210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln Ala
                260                 265                 270

Cys Arg Pro Gly Phe Tyr Lys Ala Leu Asp Gly Asn Met Lys Cys Ala
                275                 280                 285

Lys Cys Pro Pro His Ser Ser Thr Gln Glu Asp Gly Ser Met Asn Cys
            290                 295                 300

Arg Cys Glu Asn Asn Tyr Phe Arg Ala Asp Lys Asp Pro Pro Ser Met
305                 310                 315                 320

Ala Cys Thr Arg Pro Pro Ser Ser Pro Arg Asn Val Ile Ser Asn Ile
                325                 330                 335

Asn Glu Thr Ser Val Ile Leu Asp Trp Ser Trp Pro Leu Asp Thr Gly
                340                 345                 350

Gly Arg Lys Asp Val Thr Phe Asn Ile Ile Cys Lys Lys Cys Gly Trp
            355                 360                 365

Asn Ile Lys Gln Cys Glu Pro Cys Ser Pro Asn Val Arg Phe Leu Pro
            370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
                405                 410                 415

Glu Leu Ser Ser Pro Pro Arg Gln Phe Ala Ala Val Ser Ile Thr Thr
            420                 425                 430

Asn Gln Ala Ala Pro Ser Pro Val Leu Thr Ile Lys Lys Asp Arg Thr
            435                 440                 445

Ser Arg Asn Ser Ile Ser Leu Ser Trp Gln Glu Pro Glu His Pro Asn
450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
                485                 490                 495

Ser Ser Leu Lys Pro Asp Thr Ile Tyr Val Phe Gln Ile Arg Ala Arg
            500                 505                 510

Thr Ala Ala Gly Tyr Gly Thr Asn Ser Arg Lys Phe Glu Phe Glu Thr
            515                 520                 525

Ser Pro Asp Ser Phe Ser Ile Ser Gly Glu Ser Ser Gln
            530                 535                 540

<210> SEQ ID NO 31
<211> LENGTH: 547
<212> TYPE: PRT
<213> ORGANISM: Artificial Sequence
<220> FEATURE:
<223> OTHER INFORMATION: extracellular EphA4 synthetic polypeptide

<400> SEQUENCE: 31

```
Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
            35                  40                  45

Pro Leu Glu Gly Gly Trp Glu Val Ser Ile Met Asp Glu Lys Asn
50                  55                  60

Thr Pro Ile Arg Thr Tyr Gln Val Cys Asn Val Met Glu Pro Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
                100                 105                 110

Gly Val Met Gly Thr Cys Lys Glu Thr Phe Asn Leu Tyr Tyr Tyr Glu
                115                 120                 125

Ser Asp Asn Asp Lys Glu Arg Phe Ile Arg Glu Asn Gln Phe Val Lys
    130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
                180                 185                 190

Ala Leu Val Ser Val Arg Val Phe Tyr Lys Lys Cys Pro Leu Thr Val
                195                 200                 205

Arg Asn Leu Ala Gln Phe Pro Asp Thr Ile Thr Gly Ala Asp Thr Ser
    210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
                260                 265                 270

Cys Gln Ala Cys Lys Ile Gly Tyr Tyr Lys Ala Leu Ser Thr Asp Ala
    275                 280                 285

Thr Cys Ala Lys Cys Pro Pro His Ser Tyr Ser Val Trp Glu Gly Ala
    290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
                340                 345                 350

Asn Thr Gly Gly Arg Gln Asp Ile Ser Tyr Asn Val Val Cys Lys Lys
                355                 360                 365

Cys Gly Ala Gly Asp Pro Ser Lys Cys Arg Pro Cys Gly Ser Gly Val
                370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                405                 410                 415
```

-continued

```
Asn Gly Val Ser Lys Tyr Asn Pro Asn Pro Asp Gln Ser Val Ser Val
                420                 425                 430

Thr Val Thr Thr Asn Gln Ala Ala Pro Ser Ser Ile Ala Leu Val Gln
            435                 440                 445

Ala Lys Glu Val Thr Arg Tyr Ser Val Ala Leu Ala Trp Leu Glu Pro
        450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
            500                 505                 510

Val Arg Ala Arg Thr Ala Ala Gly Tyr Gly Asp Phe Ser Glu Pro Leu
        515                 520                 525

Glu Val Thr Thr Asn Thr Val Pro Ser Arg Ile Ile Gly Asp Gly Ala
530                 535                 540

Asn Ser Thr
545
```

<210> SEQ ID NO 32
<211> LENGTH: 537
<212> TYPE: PRT
<213> ORGANISM: Artificial Sequence
<220> FEATURE:
<223> OTHER INFORMATION: extracellular EphB4 synthetic polypeptide

<400> SEQUENCE: 32

```
Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Asp Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220
```

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
            245                 250                 255

Pro Gly Phe Glu Ala Ala Glu Gly Asn Thr Lys Cys Arg Ala Cys Ala
        260                 265                 270

Gln Gly Thr Phe Lys Pro Leu Ser Gly Glu Gly Ser Cys Gln Pro Cys
    275                 280                 285

Pro Ala Asn Ser His Ser Asn Thr Ile Gly Ser Ala Val Cys Gln Cys
290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
            325                 330                 335

Ser Ser Leu His Leu Glu Trp Ser Ala Pro Leu Glu Ser Gly Gly Arg
        340                 345                 350

Glu Asp Leu Thr Tyr Ala Leu Arg Cys Arg Glu Cys Arg Pro Gly Gly
    355                 360                 365

Ser Cys Ala Pro Cys Gly Gly Asp Leu Thr Phe Asp Pro Gly Pro Arg
370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
            405                 410                 415

Thr Gly Pro Val Pro Phe Glu Pro Val Asn Val Thr Thr Asp Arg Glu
        420                 425                 430

Val Pro Pro Ala Val Ser Asp Ile Arg Val Thr Arg Ser Ser Pro Ser
    435                 440                 445

Ser Leu Ser Leu Ala Trp Ala Val Pro Arg Ala Pro Ser Gly Ala Val
450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
            485                 490                 495

Leu Lys Arg Gly Ala Ser Tyr Leu Val Gln Val Arg Ala Arg Ser Glu
        500                 505                 510

Ala Gly Tyr Gly Pro Phe Gly Gln Glu His His Ser Gln Thr Gln Leu
    515                 520                 525

Asp Glu Ser Glu Gly Trp Arg Glu Gln
530                 535

<210> SEQ ID NO 33
<211> LENGTH: 19
<212> TYPE: PRT
<213> ORGANISM: Artificial Sequence
<220> FEATURE:
<223> OTHER INFORMATION: EphA4 signal peptide

<400> SEQUENCE: 33

Met Ala Gly Ile Phe Tyr Phe Ala Leu Phe Ser Cys Leu Phe Gly Ile
1               5                   10                  15

Cys Asp Ala

<210> SEQ ID NO 34
<211> LENGTH: 24
<212> TYPE: PRT

```
<213> ORGANISM: Artificial Sequence
<220> FEATURE:
<223> OTHER INFORMATION: tryptic peptide fragment of fibronectin type
      III region

<400> SEQUENCE: 34

Val Ser Ile Thr Asp Leu Leu Ala His Thr Asn Tyr Thr Phe Glu Ile
1               5                   10                  15

Trp Ala Val Asn Gly Val Ser Lys
            20

<210> SEQ ID NO 35
<211> LENGTH: 14
<212> TYPE: PRT
<213> ORGANISM: Artificial Sequence
<220> FEATURE:
<223> OTHER INFORMATION: tryptic peptide fragment of cysteine-rich
      domain

<400> SEQUENCE: 35

Gly Ser Cys Val Asn Asn Ser Glu Glu Lys Asp Val Pro Lys
1               5                   10

<210> SEQ ID NO 36
<211> LENGTH: 13
<212> TYPE: PRT
<213> ORGANISM: Artificial Sequence
<220> FEATURE:
<223> OTHER INFORMATION: tryptic peptide fragment of CH2 hinge region

<400> SEQUENCE: 36

Thr Lys Pro Arg Glu Glu Gln Phe Asn Ser Thr Tyr Arg
1               5                   10

<210> SEQ ID NO 37
<211> LENGTH: 41
<212> TYPE: PRT
<213> ORGANISM: Artificial Sequence
<220> FEATURE:
<223> OTHER INFORMATION: tryptic peptide fragment of fibronectin type
      III region

<400> SEQUENCE: 37

Ala Asp Asn Asp Ala Ala Ser Met Pro Cys Thr Arg Pro Pro Ser Ala
1               5                   10                  15

Pro Leu Asn Leu Ile Ser Asn Val Asn Glu Thr Val Asn Leu Glu Trp
            20                  25                  30

Ser Ser Pro Gln Asn Thr Gly Gly Arg
            35                  40
```

MAMMALIAN EPHA4 POLYPEPTIDE DERIVATIVES LACKING ONE OR MORE N-GLYCOSYLATION SITES AND METHOD OF USE THEREOF

This application is the U.S. national phase of International Application No. PCT/AU2016/051010, filed Oct. 27, 2016, which designated the U.S. and claims priority from Australian Provisional Patent Application No. 2015904387, filed on 27 Oct. 2015, entitled "A method of treatment and agents useful for same", the entire contents of which are incorporated herein by reference, in their entirety.

An ASCII file is being submitted electronically via EFS-Web and forms part of the official record. The entire content of the ASCII text file entitled "ST25.txt" (created on Jun. 27, 2018 and having a size of 123 kb) is incorporated herein by reference.

BACKGROUND

Field

The present disclosure relates generally to the treatment of diseases and conditions exacerbated by signaling via the erythropoietin-producing-hepatoma (Eph) family of receptor kinases and to agents useful in such treatment.

Description of Related Art

Bibliographic details of the publications referred to by author in this specification are collected alphabetically at the end of the description.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavor to which this specification relates.

The adult mammalian central nervous system (CNS) has only a limited capacity for functional regeneration following disease or trauma (Spanevello et al. (2013) *J. Neurotrauma* 30:1023-1034). Successful clinical intervention following, for example, spinal cord injury, has been an elusive goal.

Blocking of inhibitory molecules at the sites of CNS disease or injury has been proposed as a strategy to promote axonal regeneration and functional recovery (Goldshmit et al. (2004) *J. Neurosci.* 24:10,064-10,073; Goldshmit et al. (2011) *PLos ONE* 6:e24636). One group of inhibitory molecules are members of the Eph receptor:ephrin ligand signaling system (International Patent Publication No. WO 2000/024413). Eph receptor activity is also involved in conditions outside the CNS such as myocardial infarction, inflammation and cancer (reviewed by Boyd et al. (2014) *Nat. Rev. Drug Discovery* 13:39-62; Coulthard et al. (2012) *Am J Path* 181:1493-1503).

The Eph:ephrin family is divided into two subgroups, A and B (Qin et al. (2010) *J. Biol. Chem.* 285:644-654; Bowden et al. (2009) *Structure* 17:1386-1397). One particular Eph receptor, EphA4, and its ligands, are upregulated following spinal cord injury and this antagonizes axonal regeneration (Fabes et al. (2006) *Eur. J. Neurosci.* 23:1721-1730; Arocho et al. (2011) *Cell. Mol. Neurobiol.* 31:1057-1069). It is not surprising, therefore, that components of the Eph:ephrin signaling pathway have been considered as suitable therapeutic targets. Indeed, antagonism of EphA4 by a soluble fusion protein comprising the extracellular domain of EphA4 and the Fc region of IgG, referred to as "EphA4-Fc", can lead to axonal regeneration (WO 2000/24413; Goldshmit et al. (2004) supra; Goldshmit et al. (2011) supra); Spanevello et al. (2013) *J Neurotrauma* 30:1023-1034.

Despite recognition of the Eph:ephrin signaling system as a potential therapeutic strategy, the relatively rapid clearance of EphA4-Fc limits the efficacy of this form of therapy. There is an urgent need to develop agents the administration of which can maintain inhibitory serum concentrations. One option is to investigate post-translation modifications of proteins such as glycosylation.

However, the literature is inconsistent on the role glycosylation plays in protein functionality and pharmacokinetics. For example, Yamada et al. (2013) *Virology* 94:270-275 found that N-glycan additions can enhance virus production whereas loss of an N-glycan site can reduce effective production and render viral components unstable. Takahashi et al. (2008) *Biochimica et Biophysica Actal* 780:520-524 found that removing N-glycan sites resulted in significant loss of protein expression, as did Gerometta and Adams (WO2014/124487) for a majority of N-glycan sites, although there was a modest PK improvement when some N-glycan residues were mutated. Ferluga et al. (2013) *J. Biol. Chem.* 288(25):18448-18457 found that deglycosylation had a negative impact on ephrin-A1 activity. Elliot et al. (2003) *Nature Biotechnology* 21(4):414-421 showed that introducing new N-glycosylation sites substantially increased the in vivo activity and prolonged the duration of action of recombinant human EPO, leptin and the Mpl ligand. Similarly, Stork et al. (2008) *J. Biol. Chem.* 283:7804-7812 introduced N-glycan sites into a bispecific single-chain diabody and consequently extended the circulating half-life. However, Jones et al. (2007) *Glycobiology* 17(5):529-540 and Goetze et al. (2011) *Glycobiology*, 21(7): 949-959 demonstrated that in vivo clearance of Fc-fusion proteins and antibodies containing N-glycans can depend on N-glycan structure.

Hence, it is unclear and certainly not predictable what the affect would be of modifying glycosylation patterns on proteinaceous Eph signaling antagonists.

SUMMARY

Amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present disclosure enables a method for treating a disease or condition, the functional recovery from which, is adversely affected by Eph:ephrin-mediated signaling. The development of the present invention is predicated in part on the determination that the Eph:ephrin signaling antagonist, EphA4-Fc, has a particularly short half-life. Enabled herein are modified forms of EphA4-Fc in which N-glycosylation sites are eliminated in all or part. Further enabled herein are functionally equivalent modifications to any Eph molecule. Surprisingly, the modified forms of Eph molecules retain effective antagonistic activity longer in serum than the non-modified Eph molecules. Any Eph molecule can benefit from the modifying mutations including an EphA molecule (e.g. EphA1 through A8) and an EphB molecule (e.g. EphB1 through B6) as well as these forms fused or coupled to a half-life extending or stabilizing molecule such as but not limited to an immunoglobulin or immunoglobulin fragment (e.g. an Fc portion), a protein or protein fragment (e.g. human serum albumin [HSA]) or a polyether compound (e.g. polyethylene glycol [PEG]). In an embodiment, the disease or condition is in the central nervous system (CNS) or the systemic vasculature. Examples include brain or spinal cord injury, traumatic brain injury or the brain injury after thrombolysis, a neurodegenerative condition (e.g. motor neuron disease [MND]), neuronal inflammation, and ischemic-reperfusion injury of the heart or other organ (e.g. kidney reperfusion), myocardial infarction and hepatic reperfusion, inflammation and cancer.

For the sake of brevity, the Eph glycosylation-based antagonist is referred to as "Eph-X" meaning an Eph, modified to eliminate at least one N-glycosylation site, fused or coupled to molecule X wherein X is a half-life extending molecule selected from but not limited to an immunoglobulin or immunoglobulin fragment (e.g. an Fc portion), a protein or protein fragment (e.g. HSA) or a polyether (e.g. PEG). In an embodiment, Eph-X is EphA4-X wherein X is a portion of an immunoglobulin molecule, a protein or a polyether wherein the EphA4 is modified to eliminate at least one N-glycosylation site.

Accordingly, the present specification is instructional on a method for treating a disease or condition exacerbated by Eph-mediated signaling in a mammalian subject, the method comprising the administration of an effective amount of fusion molecule, Eph-X, the Eph modified to eliminate at least one N-glycosylation site wherein the Eph in the Eph-X fusion molecule is the Eph associated with the Eph-mediated signaling and X is an immunoglobulin or immunoglobulin fragment (e.g. an Fc portion), a protein or protein fragment (e.g. HSA) or a polyether (e.g. PEG). In an embodiment, the present specification is instructional on a method for treating a disease or condition exacerbated by EphA4-mediated signaling in a mammalian subject, the method comprising the administration of an effective amount of EphA4-X, wherein the Eph is modified to eliminate at least one N-glycosylation site and X is an immunoglobulin or immunoglobulin fragment (e.g. an Fc portion) a protein or protein fragment (e.g. HSA) or a polyether (e.g. PEG).

In another embodiment, the present specification teaches a method for treating a disease or condition exacerbated by EphA- or EphB-mediated signaling in a mammalian subject, the method comprising the administration of an effective amount of EphA-X or EphB-X, the EphA or EphB modified to eliminate at least one N-glycosylation site wherein the EphA is selected from EphA1 through A8 and EphB is EphB1 through B6 and X is an immunoglobulin or immunoglobulin fragment (e.g. an Fc portion), a protein or protein fragment (e.g. HSA) or a polyether (e.g. PEG). It is proposed and enabled herein that elimination of an N-glycosylation site can result in longer serum half-life with no significant loss of antagonistic function. In an embodiment, X is an Fc such as but not limited to IgG4 Fc or IgG1 Fc. In an embodiment, the mammalian subject is a human subject.

In an embodiment, the present specification is instructional on a method for treating a disease or condition exacerbated by EphA4-mediated signaling in a mammalian subject, the method comprising the administration of an effective amount of EphA4-Fc, the Eph modified to eliminate at least one N-glycosylation site. A mammalian subject includes a human subject. The Fc includes an IgG4 Fc or an IgG1 Fc.

In an embodiment, the eliminated N-glycosylation site is located at an amino acid residue selected from the group consisting of positions 216, 321 and 389 of human EphA4-Fc having the amino acid sequence set forth in SEQ ID NO:1 or the equivalent in an EphA4 from another species or the equivalent in another EphA or an EphB. These amino acid positions are calculated based on the absence of the 19 amino acid signal peptide sequence (SEQ ID NO:33). The corresponding amino acid positions with the signal sequence are 235, 340 and 408, respectively. Murine-derived EphA4-Fc (SEQ ID NO:9), for example, has N-glycosylation sites at the same location as the human form. In an embodiment, two or more N-glycosylation sites are eliminated. In a further embodiment, two or all three N-glycosylation sites are eliminated. Potential N-glycosylation sites in EphA2, A3, A4 and EphB4 are shown in FIGS. 11A through D [SEQ ID NOs:29 to 32].

Conveniently, the N-glycosylation sites are eliminated by a substitution of the asparagine (Asn;N) residue at one or more of amino acid positions 216, 321 and/or 389 of human EphA4-Fc (corresponding to positions 235, 340 and 408 with the leader sequence) or the equivalent position in an EphA4-Fc derived from another species or the equivalent in another EphA or an EphB. This is referred to as a $Z_1 n_b Z_2$ substitution where $Z_1$ is asparagine (Asn;N) and $Z_2$ is any amino acid residue except Asparagine. In an embodiment, $Z_2$ is glutamine (Gln;Q).

Hence, in relation to EphA4, enabled herein is a method for treating a disease or condition exacerbated by EphA4-mediated signaling in a human subject, the method comprising the administration of an effective amount of an N-glycosylated modified EphA4-Fc having an amino acid sequence selected from the list consisting of SEQ ID NO:2 through 8 or an amino acid sequence having at least 80% similarity to any of SEQ ID NO:2 through 8 after optimal alignment provided the same N-glycosylation sites remain eliminated.

In addition, the present specification is instructional for a method of treating a disease or condition of the CNS or systemic vasculature or ischemic-reperfusion injury of the heart or other organ (e.g. kidney or liver) or myocardial infarction, inflammation (neuronal or systemic) or cancer in a human subject, the method comprising administering to the subject an effective amount of a human EphA4-Fc molecule as defined by the amino acid sequence set forth in SEQ ID NO:1 but carrying a single or multiple amino acid substitution defined by the group consisting of N216Z, N321Z, N389Z, N216Z+N321Z, N216Z+N389Z, N321Z+N389Z and N216Z+N321Z+N389Z wherein Z is any amino acid other than asparagine. These amino acid positions are calculated in the absence of the 19 amino acid leader (signal) peptide sequence. If the leader sequence is included (SEQ ID NO:33), the positions are: N235Z, N340Z, N408Z, N235Z+N340Z, N235Z+N408Z, N340Z+N408Z and N235Z+N340Z+N408Z, respectively.

In an embodiment, Z is glutamine (Gln;Q).

The present specification further teaches modified EphA4-Fc molecules with an elimination of at least one N-glycosylation site which has an increased serum half-life and which retains EphA4 signaling antagonism. Examples of modified human EphA4-Fc molecules include SEQ ID NO:2 through 8 or the equivalent in non-human mammals such as mice as set forth in SEQ ID NO:10 through 16. As indicated above, the present invention extends to any modified Eph such as but not limited to an EphA (e.g. EphA1 through A8) and an EphB (e.g. EphB1 through B6) which have N-glycosylation sites eliminated. Pharmaceutical compositions and therapeutic kits are also contemplated herein.

TABLE 1

Summary of sequence identifiers

| SEQUENCE ID NO: | DESCRIPTION |
|---|---|
| 1 | Amino acid sequence of unmodified human EphA4-Fc |
| 2 | Amino acid sequence of modified human EphA4-Fc comprising an asparagine to glutamine substitution at amino acid 216 |
| 3 | Amino acid sequence of modified human EphA4-Fc comprising an asparagine to glutamine substitution at amino acid 321 |
| 4 | Amino acid sequence of modified human EphA4-Fc comprising an asparagine to glutamine substitution at amino acid 389 |
| 5 | Amino acid sequence of modified human EphA4-Fc comprising an asparagine to glutamine substitution at amino acid 216 and 321 |
| 6 | Amino acid sequence of modified human EphA4-Fc comprising an asparagine to glutamine substitution at amino acid 216 and 389 |
| 7 | Amino acid sequence of modified human EphA4-Fc comprising an asparagine to glutamine substitution at amino acid 321 and 389 |
| 8 | Amino acid sequence of modified human EphA4-Fc comprising an asparagine to glutamine substitution at amino acid 216, 321 and 389 |
| 9 | Amino acid sequence of unmodified murine EphA4-Fc |
| 10 | Amino acid sequence of modified murine EphA4-Fc comprising an asparagine to glutamine substitution at amino acid 216 |
| 11 | Amino acid sequence of modified murine EphA4-Fc comprising an asparagine to glutamine substitution at amino acid 321 |
| 12 | Amino acid sequence of modified murine EphA4-Fc comprising an asparagine to glutamine substitution at amino acid 389 |
| 13 | Amino acid sequence of modified murine EphA4-Fc comprising an asparagine to glutamine substitution at amino acid 216 and 321 |
| 14 | Amino acid sequence of modified murine EphA4-Fc comprising an asparagine to glutamine substitution at amino acid 216 and 389 |
| 15 | Amino acid sequence of modified murine EphA4-Fc comprising an asparagine to glutamine substitution at amino acid 321 and 389 |
| 16 | Amino acid sequence of modified murine EphA4-Fc comprising an asparagine to glutamine substitution at amino acid 216, 321 and 389 |
| 17 | Nucleotide sequence of sense primer for human EphA4-Fc mutagenesis at amino acid position 216 |
| 18 | Nucleotide sequence of antisense primer for human EpHA4-Fc mutagenesis at primer position 216 |
| 19 | Nucleotide sequence of sense primer for human EphA4-Fc mutagenesis at amino acid position 321 |
| 20 | Nucleotide sequence of antisense primer for human EpHA4-Fc mutagenesis at primer position 321 |
| 21 | Nucleotide sequence of sense primer for human EphA4-Fc mutagenesis at amino acid position 389 |
| 22 | Nucleotide sequence of antisense primer for human EpHA4-Fc mutagenesis at primer position 389 |
| 23 | Nucleotide sequence of sense primer for murine EphA4-Fc mutagenesis at amino acid position 216 |
| 24 | Nucleotide sequence of antisense primer for murine EphA4-Fc mutagenesis at amino acid position 216 |
| 25 | Nucleotide sequence of sense primer for murine EphA4-Fc mutagenesis at amino acid position 321 |
| 26 | Nucleotide sequence of antisense primer for murine EphA4-Fc mutagenesis at amino acid position 321 |
| 27 | Nucleotide sequence of sense primer for murine EphA4-Fc mutagenesis at amino acid position 389 |
| 28 | Nucleotide sequence of antisense primer for murine EphA4-Fc mutagenesis at amino acid position 389 |
| 29 | Amino acid sequence of extracellular EphA2 with predicted N-glycosylation sites shown at amino acids 407 and 435[1] |
| 30 | Amino acid sequence of extracellular EphA3 with predicted N-glycosylation sites shown at amino acids 232, 337, 391, 404 and 493[1] |
| 31 | Amino acid sequence of extracellular EphA4 with predicted N-glycosylation sites shown at amino acids 235, 340 and 408[1] |
| 32 | Amino acid sequence of extracellular EphB4 with predicted N-glycosylation sites shown at amino acids 203, 335 and 426[1] |
| 33 | Amino acid sequence of EphA4 N-terminal leader sequence (signal peptide sequence) which is cleaved during expression |
| 34 | Amino acid sequence of tryptic peptide fragment of fibronectin type III (FN1) region of EphA4-Fc |
| 35 | Amino acid sequence of tryptic peptide fragment of cysteine-rich domain (CRD) region of EphA4-Fc |
| 36 | Amino acid sequence of tryptic peptide fragment of CH2 hinge region of Fc portion of EphA4-Fc |
| 37 | Amino acid sequence of tryptic peptide fragment of fibronetin type III (FN1) region of EphA4-Fc |

[1]These amino acid sequences and positions contain an N-terminal leader (signal) sequence.

BRIEF DESCRIPTION OF THE FIGURES

Some figures contain color representations or entities. Color photographs are available from the Patentee upon request or from an appropriate Patent Office. A fee may be imposed if obtained from a Patent Office.

FIG. 2A is a representation of the amino acid sequence of wild-type human EphA4-Fc (SEQ ID NO: 1) showing the sites of N-linked glycosylation of asparagine (N) residues for subsequent mutation to glutamine (Q). The amino acid sequence does not contain the 19 amino acid leader sequence (SEQ ID NO: 33), which is cleaved off during expression.

FIG. 2B is a photographic representation of an SDS PAGE of modified human EphA4-Fc compared to wild-type human EphA4-Fc. 1. N216Q substitution; 2. Double N216Q+N321Q substitution; 3. Triple N216Q+N321Q+N389Q substitution; 4. Wild-type human EphA4-Fc. Amino acid position numbers calculated in absence of the 19 amino acid signal sequence (SEQ ID NO:33).

FIG. 2C is a photographic representation of an SDS PAGE of modified murine EphA4-Fc compared to wild-type murine EphA4-Fc. 1. Wild-type murine EphA4-Fc; 2. Single N321Q substitution; 3. Triple N216Q+N321Q+N389Q substitution. Amino acid position numbers calculated in absence of the 19 amino acid signal sequence (SEQ ID NO:33).

FIGS. 10A through 10C are graphical representations of binding curves of human EphA4 wild-type versus mutant to ephrin-Fc. (FIG. 10A) Ephrin A4:WT versus mutant; (FIG. 10B) Ephrin A5:WT versus mutant; (FIG. 10C) Ephrin B3:WT versus mutant. "WT" means "wild-type" with no change in N-glycosylation sites. Mutant means triple N-glycan mutant. ●WT ■Mutant FIGS. 11A through 11D show extracellular Eph amino acid sequences from (FIG. 11A) EphA2; (FIG. 11B) EphA3; (FIG. 11C) EphA4; and (FIG. 11D) EphB4 with the predicted N-glycosylation sites highlighted (see also Table 1 and SEQ ID NOs:29 through 32) for the positions of these sites. A 19mer leader sequence is cleaved off during expression.

(FIG. 15A) Ephrin-binding ELISA of EphA4-Fc deglycosylated and wild-type proteins to immobilized EphrinA5 (i) and EphrinA4 (ii); (FIG. 15B) octet biosensor analysis of EphA4-Fc deglycosylated and wild-type proteins to streptavidin coupled octet probes labeled with biotein-conjugated EphrinA4-Fc protein; (FIG. 15C) flow cytometric analysis of binding of EphA4-Fc deglycosylated and wild-type proteins to EphrinA5 expressing CHO cell line.

FIG. 16A is a graphical representation showing hind limb grip strength force of EphA4-Fc vs control, week 18; FIG. 16B is a graphical representation showing RotaRod latency to fall time of EphA4-Fc vs control, week 20.

(Abbreviation: EphA4$^{F/W}$; SOD1$^{G93A}$, EphA4$^{flox/WT}$×ChAT-Cre$^{KI/KI}$×SOD1$^{G93A}$; EphA4$^{WT/WT}$; SOD1$^{G93A}$, EphA4$^{flox/flox}$×ChAT-Cre$^{WT/WT}$×SOD1$^{G93A}$).

Figure 19:
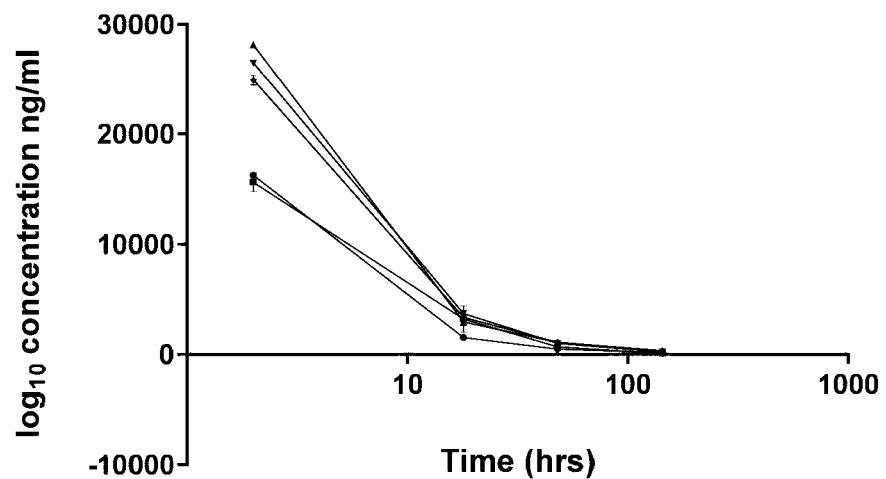

FIG. 19 is a graphical representation of wild-type EphA2 versus mutant forms of EphA2 at the glycan sites as a function of clearance in rates. Results show no improvement in pharmacokinetic (PK) behavior.

DETAILED DESCRIPTION

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a mutation" includes a single mutation, as well as two or more mutations; reference to "an antagonist" includes a single antagonist, as well as two or more antagonists; reference to "the disclosure" includes a single and multiple aspects taught by the disclosure; and so forth. Aspects taught and enabled herein are encompassed by the term "invention". All such aspects are enabled within the width of the present invention. Any variants and derivatives contemplated herein are encompassed by "forms" of the invention.

The present disclosure teaches a fusion or coupled molecule between an Eph, modified by at least one amino acid substitution to eliminate on N-glycosylation site (a glycosylation-based Eph antagonist) and component or molecule X wherein X is an immunoglobulin or immunoglobulin fragment (e.g. an Fc portion), a protein or protein fragment (e.g. HSA) or a polyether (e.g. PEG). The fusion or coupled molecule is referred to as "Eph-X" wherein Eph includes an EphA or EphB and X is an immunoglobulin or immunoglobulin fragment (e.g. an Fc portion), a protein or protein fragment (e.g. HSA) or a polyether (e.g. PEG). Reference to "EphA" includes EphA1, EphA2, EphA3, EphA4, EphA5, EphA6, EphA7 and EphA8. Reference to "EphB" includes EphB1, EphB2, EphB3, EphB4, EphB5 and EphB6. Reference to a "modified" form includes a "modification", "mutant" and "mutation" to Eph at an amino acid residue to eliminate at least on N-glycosylation site. The instant disclosure teaches single or multiple mutations of amino acid residues wherein the mutation is a substitution. For convenience, a mutation or modification in the form of an amino acid substitution is defined herein as $Z_1n_bZ_2$ wherein $Z_1$ is the amino acid before the substitution, $Z_2$ is the amino acid after the substitution and $n_b$ is the amino acid residue number. The present invention extends to an Eph comprising a modified amino acid sequence which eliminates at least one N-glycosylation site. The Eph includes an EphA (e.g. EphA1 through A8) and an EphB (e.g. EphB1 through B6). Hence, an Eph glycosylation-based antagonist (Eph-X) means an Eph modified to eliminate at least one N-glycosylation site fused or coupled to X where X is a half-life extending molecule such as an Fc portion. When the Eph is EphA4, the molecule is EphA4-X wherein X is a portion of an immunoglobulin molecule (e.g. Fc), a protein or a polyether.

In an embodiment, the Eph is EphA4 modified to eliminate at least one N-glycosylation site fused to an IgG Fc (e.g. IgG4 Fc or IgG1 Fc).

This fusion molecule of human EphA4 with the human IgG Fc portion is referred to as "EphA4-Fc". For convenience, a non-mutated EphA4-Fc is referred to herein as wild-type (WT) EphA4-Fc even though it is an artificially created molecule. Equally a non-mutated Eph-X is referred to as WT Eph-X wherein X is an immunoglobulin or immunoglobulin fragment (e.g. an Fc portion), a protein or protein fragment (e.g. HA) or polyether (e.g. PEG).

For the avoidance of doubt, the present invention extends to a fusion or coupled Eph-X molecule wherein Eph is an EphA or an EphB and X is an immunoglobulin or immunoglobulin fragment (e.g. an Fc portion), a protein or protein fragment (e.g. HSA) or a polyether (e.g. PEG). An example is EphA4-X. The X component is a half-life or stability conferring molecule.

In an embodiment, Eph-X is EphA4-X such as EphA4-Fc. EphA4-Fc may be represented in various ways such as recombinant (r) human (Hu) EphA4-Fc. The amino acid sequence for WT human EphA4-Fc is set forth in SEQ ID NO:1. Substitution mutations which remove an N-glycosylation site are contemplated in SEQ ID NO:1. Examples include substitution of an asparagine (Asn;N) at a site selected from the group consisting of amino acid residue number 216, 321 and 389 represented as N216Z, N321Z and N389Z, respectively, wherein Z is any amino acid other than asparagine (Asn;N) and wherein the mutation removes an N-glycosylation site at this residue. These amino acid positions are based on a sequence where the 19 amino acid leader (signal) sequence has been cleaved off. The signal sequence is SEQ ID NO:33. If the signal sequence is included, the positions are 235, 340 and 408, respectively. Single mutations in SEQ ID NO:1 (WT EphA4-Fc) corresponding to the site 216, 321 or 389 include a substitution to glutamine (Gln;Q), i.e. N216Q, N321Q and N389Q, respectively. These correspond to SEQ ID NO:2, SEQ ID NO:3 and SEQ ID NO:4, respectively. Again, based on the absence of the 19 amino acid N-terminal signal sequence. In the avoidance of doubt, the amino acid sequence of EphA4-Fc, without the leader sequence, begins with the amino acid sequence VTGSRVYPANE.

Multiple mutations may also be introduced such as double substitutions of N216Z+N321Z, N216Z+N389Z and N321Z+N389Z where Z is any amino acid other than asparagine (Asn;N) and the double substitution removes 2 N-glycosylation sites. Examples include N216Q+N321Q, N216Q+N389Q and N321Q+N389Q (SEQ ID NO:5, SEQ ID NO:6 and SEQ ID NO:7, respectively). A triple mutation of N216Z+N321Z+N389Z wherein Z is any amino acid other than asparagine (Asn;N) and the triple substitution removes 3 N-glycosylation sites. An example includes N216Q+N321Q+N389Q (SEQ ID NO:8).

A similar nomenclature is used for non-human derived EphA4-Fc molecules such as wild-type murine EphA4-Fc (SEQ ID NO:9). This may contain the same substitution mutations at amino acid positions 216, 321 and/or 389 as represented by N216Z, N321Z, N389Z, N216Z+N321Z, N216Z+N389Z, N321Z+N389Z and N216Z+N321Z+N389Z, wherein Z is any amino acid except asparagine (Asn;N) and the mutations remove 1, 2 or 3 N-glycosylation sites. Examples include N216Q, N321Q, N389Q, N216Q+N321Q, N216Q+N389Q, N321Q+N389Q and N216Q+N321Q+N389Q (SEQ ID NOs:10 through 16, respectively.

Hence, it is proposed herein that removal of at least 1 N-glycosylation site such as 1, 2 or 3 N-glycosylation sites from wild-type EphA4-Fc increases its serum half-life without decreasing its ability to antagonize EphA4-mediated signaling thus making the molecule surprisingly more efficacious in the treatment of a disease or condition of the central nervous system (CNS) or of the systemic vasculature which would otherwise be exacerbated by EphA4-mediated signaling. Similar comments apply to other Eph molecules carrying an amino acid mutation to eliminate at least an N-glycosylation site. For example, EphA2 comprises predicted N-glycosylation sites at amino acid positions 407 and 435; EphA3 comprises predicted N-glycosylation sites at amino acid positions 232, 337, 391, 404 and 493; EphB4 comprises sites at amino acids 203, 335 and 426.

Diseases or conditions of the CNS include injury or disease of the brain (e.g. stroke, neurodegenerative disease (e.g. motor neuron disease [MND]), traumatic brain injury or brain injury following thrombolysis) or spinal cord leading to gliosis and/or glial scarring and/or neuronal inflammation. By antagonizing Eph-mediated signaling, it is proposed that there is a decrease in gliosis, glial scarring and/or inflammation and this leads to or facilitates axonal regeneration. The term "gliosis" includes any condition resulting in a gliotic response including inhibition of axon growth.

A disease or condition of the systemic vasculature includes cardiovascular conditions and ischemic-reperfusion injury. The latter may occur in the heart or it may be elsewhere such as intestinal ischemia-reperfusion injury or an organ such as kidney reperfusion or hepatic reperfusion. There may be other downstream conditions which may also be ameliorated by the modified Eph-X (e.g. EphA4-X) such as diabetes. Other conditions include myocardial infarction, non-CNS-related inflammation, reperfusion injury, organ damage such as kidney or hepatic reperfusion and cancer.

Accordingly, the present specification teaches a method for treating a disease or condition exacerbated by Eph-mediated signaling in a mammalian subject, the method comprising the administration of an effective amount of Eph-X, the Eph modified to eliminate at least one N-glycosylation site wherein the Eph is selected from EphA1 through A8 and EphB1 through B6 and X is an immunoglobulin or immunoglobulin fragment (e.g. an Fc portion), a protein or protein fragment (e.g. HSA) or a polyether (e.g. PEG). It is proposed and enabled herein that elimination of an N-glycosylation site can result in longer serum half-life with no significant loss of antagonistic function. The Eph is coupled or fused to X.

In an embodiment, Eph-X is EphA4-X such as EphA4-Fc. Hence, the present invention contemplates a treatment for a disease or condition exacerbated by EphA4-mediated signaling in a mammalian subject, the method comprising the administration of an effective amount of an EphA4-Fc modified to eliminate at least on N-glycosylation site. Diseases and conditions include and encompass a disease or condition of the CNS or systemic vasculature as well as consequential diseases or conditions as well as myocardial infarction, non-CNS-related inflammation, reperfusion injury, organ damage and cancer. In an embodiment, the mammalian subject is a human subject.

In an embodiment, the present specification teaches a method for treating a disease or condition exacerbated by EphA4-mediated signaling in a mammalian subject, the method comprising the administration of an effective amount of EphA4-X, the Eph modified to eliminate at least one N-glycosylation site where X is an immunoglobulin or immunoglobulin fragment (e.g. an Fc portion), a protein or protein fragment (e.g. HSA) or a polyether (e.g. PEG). It is proposed and enabled herein that elimination of an N-glycosylation site can result in longer serum half-life with no significant loss of antagonistic function. Reference to a "longer serum half-life" includes facilitation of increased or enhanced stability.

In an embodiment, the disease or condition exacerbated by Eph-mediated signaling is a disease or condition of the CNS.

Hence, enabled herein is a method of treating a disease or condition of the CNS in a mammalian subject, the method comprising administering to the subject an effective amount of an Eph-X molecule, the Eph modified to eliminate at least one N-glycosylation site wherein the Eph is selected from EphA1 through A8 and EhB1 through B6 and X is an immunoglobulin or immunoglobulin fragment (e.g. an Fc portion), a protein or protein fragment (e.g. HSA) or a polyether (e.g. PEG). In an example, Eph-X is EphA4-X such as EphA4-Fc.

In another embodiment, the disease or condition is a disease or condition of the systemic vasculature.

Hence, taught herein is a method of treating a disease or condition of the systemic vasculature in a mammalian subject, the method comprising administering to the subject an effective amount of an Eph-X molecule, the Eph modified to eliminate at least one N-glycosylation site wherein X is an immunoglobulin or immunoglobulin fragment (e.g. an Fc portion), a protein or protein fragment (e.g. HSA) or a polyether (e.g. PEG).

In an embodiment, the modified EphA4 is selected depending on the subject being treated. For example, a human derived EphA4-Fc mutant would be used to treat a human subject.

Enabled herein is a method of a disease or condition of the CNS exacerbated by Eph-mediated signaling in a human subject, the method comprising administering to the subject an effective amount of a human Eph-X molecule, the Eph modified to eliminate at least one N-glycosylation site wherein the Eph is selected from EphA1 through A8 and EhB1 through B6 and X is an immunoglobulin or immunoglobulin fragment (e.g. an Fc portion), a protein or protein fragment (e.g. HSA) or a polyether (e.g. PEG).

Further taught herein is a method of treating a disease or condition of the systemic vasculature in a human subject, the method comprising administering to the subject an effective amount of a human EphA4-Fc molecule modified to eliminate at least one N-glycosylation site.

Suitable modified human EphA4-Fc molecules include those having one, two or three N-glycosylation sites eliminated. This is achieved by a substitution of an asparagine (Asp;N) at any one or more of residue numbers 216, 321 and/or 389 of SEQ ID NO:1 (or 235, 340 and/or 408 if the 19 amino acid leader sequence (SEQ ID NO:33) is included) for any other amino acid except an asparagine residue as well as the functionally equivalent positions in EphA or EphB molecule.

Hence, the present specification is instructional for a method of treating a disease or condition of the CNS or systemic vasculature in a human subject, the method comprising administering to the subject an effective amount of a human EphA4-Fc molecule as defined by the amino acid sequence set forth in SEQ ID NO:1 but carrying a single or multiple amino acid substitution defined by the group consisting of N216Z, N321Z, N389Z, N216Z+N321Z, N216Z+N389Z, N321Z+N389Z and N216Z+N321Z+N389Z wherein Z is any amino acid other than asparagine. Amino acid position numbers calculated in absence of the 19 amino acid signal sequence (SEQ ID NO:33).

In an embodiment, Z is glutamine (Gln;Q).

Accordingly, the present specification enables a method for treating a disease or condition of the CNS or systemic vasculature in a human subject, the method comprising administering to the subject an effective amount of an EphA4-Fc defined by the amino acid sequence selected from the group consisting of SEQ ID NO:2 through SEQ ID NO:8.

In a particular embodiment, the EphA4-Fc contains a triple amino acid substitution of N216Q+N321Q+N389Q. Amino acid position numbers calculated in absence of the 19 amino acid signal sequence (SEQ ID NO:33).

Accordingly, the present specification enables a method for treating a disease or condition of the CNS or systemic vasculature in a human subject, the method comprising administering to the subject an effective amount of an EphA4-Fc defined by the amino acid sequence SEQ ID NO:8.

As indicated above, the selection of EphA4-Fc molecule is dependent on the mammal being treated. For example, the present invention extends to testing a mouse animal model using a murine EphA4-Fc modified as taught herein.

Also as indicated above, the modified EphA4-Fc has lost at least one N-glycosylation site but maintains its ability to antagonize EphA4-mediated signaling while having a longer serum half-life compared to a corresponding wild-type EphA4-Fc. This is not to say that the selected EphA4-Fc may not contain another amino acid substitution, deletion and/or addition, post-translational modification or additional changes in glycosylation pattern.

Hence, reference to SEQ ID NO:2 through 8 and SEQ ID NO:10 through 16 includes an amino acid sequence having at least about 80% similarity to any one of SEQ ID NOs:2 through 8 or SEQ ID NO:10 through 16 after optimal alignment with the proviso that at amino acid residue number 216, 321 and/or 389 there is a substitution for asparagine to any other amino acid other than asparagine and this removes the N-glycosylation site. Amino acid position numbers calculated in absence of the 19 amino acid signal sequence (SEQ ID NO:33).

By "at least 80% similarity" means 80, 81, 82, 83, 84, 85, 86, 87, 88, 89, 90, 91, 92, 93, 94, 95, 96, 97, 98, 99 or 100%.

The term "similarity" as used herein includes exact identity between compared sequences at the amino acid level. Where there is non-identity at the amino acid level, "similarity" includes amino acids that are nevertheless related to each other at the structural, functional, biochemical and/or conformational levels. In an embodiment, amino acid sequence comparisons are made at the level of identity rather than similarity.

Terms used to describe sequence relationships between two or more polypeptides include "reference sequence", "comparison window", "sequence similarity", "sequence identity", "percentage sequence similarity", "percentage sequence identity", "substantially similar" and "substantial identity". A "reference sequence" includes, but is not limited to, from 10 to 100 amino acid residues in length. Because two polypeptides may each comprise (1) a sequence (i.e., only a portion of the complete amino acid sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (BLASTP 2.2.32+, GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids. Res.* 25(17): 3389-3212. A detailed discussion of sequence analysis can be found in Unit 19.3 of Ausubel et al. (1994-1998) In: *Current Protocols in Molecular Biology*, John Wiley & Sons Inc. Other alignment software includes BWA (Li and Durbin (2010) *Bioinformatics* 26:589-595) and Bowtie (Langmead et al. (2009) *Genome Biol* 10:R25 and BLAT (Kent (2002) *Genome Res* 12:656-664).

The terms "sequence similarity" and "sequence identity" as used herein refer to the extent that sequences are identical or functionally or structurally similar on an amino acid-by-amino acid basis over a window of comparison. Thus, a "percentage of sequence identity", for example, is calculated by comparing two optimally aligned sequences over the window of comparison, determining the number of positions at which the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by any suitable method or computer algorithm using standard defaults as used in the reference manual accompanying the software. Similar comments apply in relation to sequence similarity.

Other mutants contemplated herein include analogs with a modification to a side chain, incorporation of an unnatural amino acid during protein synthesis and the use of a cross-linker which impose conformational constrains on the Eph-X. This term also does not exclude other modifications of the Eph-X, for example, acetylations and phosphorylations and the like. Included within the definition are, for example, polypeptides containing one or more analogs of an amino acid.

Examples of side chain modifications contemplated by the present invention include modifications of amino groups such as by reductive alkylation by reaction with an aldehyde followed by reduction with NaBH4; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH4.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Further contemplated herein is a modified EphA4-Fc comprising a modified amino acid sequence which eliminates at least one N-glycosylated site. For example, in relation to human EphA4-Fc as defined in SEQ ID NO:1, the asparagine (Asn;N) at residue 216, 321 and/or 389 is substituted by any amino acid other than asparagine.

Hence, enabled herein is a modified human EphA4-Fc comprising an amino acid sequence before modification as set forth in SEQ ID NO:1 and wherein the modification is selected from the group consisting of N216Z, N321Z, N389Z, N216Z+N321Z, N216Z+N389Z, N321Z+N389Z and N216Z+N321Z+N389Z wherein Z is any amino acid other than asparagine (Asn;N).

In an embodiment, Z is glutamine (Gln;Q).

Accordingly, taught herein is a modified human EphA4-Fc having an amino acid sequence selected from the group consisting of SEQ ID NO:2 through 8. In one particular embodiment, the modified human EphA4-Fc is defined by SEQ ID NO:8 and comprises the triple substitution N216Q+N321Q+N389Q.

Non-human modified EphA4-Fc molecules are also contemplated herein such as a murine EphA4-Fc modified to eliminate at least one N-glycosylation site. Examples include murine EphA4-Fc defined by the amino acid sequence set forth in SEQ ID NO:9 with a substitution mutation selected from N216Z, N321Z, N389Z, N216Z+N321Z, N216Z+N321Z, N321Z+N389Z and N216Z+N321Z+N389Z wherein Z is any amino acid other than asparagine (Asn;N).

When Z is glutamine (Gln;Q), examples include a modified murine EphA4-Fc selected from the group consisting of SEQ ID NO:10 through 16. The amino acid positions given above are calculated in the absence of the 19 amino acid leader sequence (SEQ ID NO:33). The corresponding positions are determined by adding 19 to the amino acid position. Hence, the corresponding positions for 261, 321 and 389 are 235, 340 and 408, respectively.

In an embodiment, the modified EphA4-Fc molecules are in isolated form.

As indicated above, the present invention extends to any Eph molecule comprising a modified amino acid sequence which eliminates at least one N-glycosylation site. Examples of Eph molecules include EphA1 through A8 and EphB1 through B6. Such modified Eph molecule may be coupled or fused to an immunoglobulin or immunoglobulin fragment (e.g. an Fc portion), a protein or protein fragment (e.g. HSA) or a polyether (e.g. PEG).

The modified Eph-X (e.g. EphA4-Fc) molecules of the present invention can also be combined with one or more pharmaceutically acceptable carriers, diluents and/or excipients to form a pharmacological composition. Pharmaceutically acceptable carriers can contain a physiologically acceptable compound that acts to, for example, stabilize the formulation. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g. Remington's Pharmaceutical Sciences, 18$^{th}$ Edition, Mack Publishing Company, Easton, Pa., 1990 ("Remington's").

Other physiologically acceptable compounds include wetting agents, emulsifying agents, dispersing agents or preservatives which are particularly useful for preventing the growth or action of microorganisms. Various preservatives are well known and include, e.g. phenol and ascorbic acid. One skilled in the art would appreciate that the choice of a pharmaceutically acceptable carrier including a physiologically acceptable compound depends, for example, on the route of administration of the modulatory agent of the invention and on its particular physio-chemical characteristics.

Administration of the agent, in the form of a pharmaceutical composition, may be performed by any convenient means known to one skilled in the art and depending on the disease or condition or site of injury. Routes of administration include, but are not limited to, respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, patch and implant. Retrograde transport or direct injection into the brain may also be used.

For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier, see, e.g. International Patent Publication Number WO 96/11698.

Agents of the present invention, when administered orally, may be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g Fix (1996) *Pharm Res* 13:1760-1764; Samanen et al. (1996) *J Pharm Pharmacol* 48:119-135; U.S. Pat. No. 5,391,377, describing lipid compositions for oral delivery of therapeutic agents.

The pharmaceutical forms suitable for injectable use include sterile aqueous solutions (where water-soluble) or dispersions and sterile powders for the extemporaneous preparation of sterile injectable solutions or dispersion or may be in the form of a cream or other form suitable for topical application. Generally, topical administration is aimed at the Eph-X (e.g. EphA4-Fc) molecule being in a formulation which enables it to enter the body systemically. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin Sterile injectable solutions are prepared by incorporating the agents in the required amount in the appropriate solvent with various of the other ingredients enumerated above, as required, followed by filtered sterilisation. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

For parenteral administration, the agent may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the agents are being administered intrathecally, they may also be dissolved in cerebrospinal fluid.

For transmucosal or transdermal administration, penetrants appropriate to the barrier to be permeated can be used for delivering the agent. Such penetrants are generally known in the art e.g. for transmucosal administration, bile salts and fusidic acid derivatives. In addition, detergents can be used to facilitate permeation. Transmucosal administration can be through nasal sprays or using suppositories e.g. Sayani and Chien (1996) *Crit Rev Ther Drug Carrier Syst* 13:85-184. For topical, transdermal administration, the agents are formulated into ointments, creams, salves, powders and gels. Transdermal delivery systems can also include patches.

For inhalation, the agents of the invention can be delivered using any system known in the art, including dry powder aerosols, liquids delivery systems, air jet nebulizers, propellant systems, and the like, see, e.g. Patton (1998) *Nat Biotech* 16:141-143; product and inhalation delivery systems for polypeptide macromolecules. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, for example, air jet nebulizers.

The agents of the invention can also be administered in sustained delivery or sustained release mechanisms, which can deliver the formulation internally. For example, biodegradeable microspheres or capsules or other biodegradeable polymer configurations capable of sustained delivery of a peptide can be included in the formulations of the invention (e.g. Putney and Burke (1998) *Nat Biotech* 16:153-157).

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes), carbohydrates, or synthetic polymers. For a general discussion of pharmacokinetics, see, e.g. Remington's.

The pharmaceutical compositions of the invention can be administered in a variety of unit dosage forms depending upon the method of administration. Dosages for typical pharmaceutical compositions are well known to those of skill in the art. Such dosages are typically advisorial in nature and are adjusted depending on the particular therapeutic context, patient tolerance, etc. The amount of agent adequate to accomplish this is defined as the "effective amount". The dosage schedule and effective amounts for this use, i.e., the "dosing regimen" will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g. *Remington's*; Egleton and Davis (1997) *Peptides* 18:1431-1439; Langer (1990) *Science* 249:1527-1533.

In an embodiment, the glycosylation site modified Eph-X such as EphA4-Fc is administered in an amount which provides detectable serum levels of from about 5 to 100 µg/mL for from 3 to 20 days. By "5-100" means 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 µg/mL. The expression "3 to 20" means 3, 4, 5, 6, 7, 8, 9, 10, 11, 12, 13, 14, 15, 16, 17, 18, 19 or 20 days. In an embodiment, the glycosylation site modified Eph-X such as EphA4-Fc carrying one or more modified N-glycosylation sites is provided in an amount which gives serum levels of from 5 to 20 µg/mL over from 3 to 10 days. These amounts include about 10 µg/mL serum levels for about 6-7 days. Hence, dosing includes weekly amounts.

In accordance with these methods, the agents and/or pharmaceutical compositions defined in accordance with the present invention may be co-administered in combination with one or more other agents. Reference herein to "co-administered" means simultaneous administration in the same formulation or in two different formulations via the same or different routes or sequential administration by the same or different routes. Reference herein to "sequential" administration is meant a time difference of from seconds, minutes, hours or days between the administration of the two types of agents and/or pharmaceutical compositions. Co-administration of the agents and/or pharmaceutical compositions may occur in any order. Agents which are particularly preferred in this regard are agents which promote neurogenesis and/or axon growth and/or inhibit inflammation such as, but not limited to cytokines and growth factors and inhibitors of inflammatory cytokines such as INFy antagonists.

Alternatively, targeting therapies may be used to deliver the active agent more specifically to certain types of cell, by the use of targeting systems such as antibodies or cell specific ligands or specific nucleic acid molecules. Targeting may be desirable for a variety of reasons, e.g., if the agent is unacceptably toxic or if it would otherwise require too high a dosage or if it would not otherwise be able to enter the target cells.

Instead of administering the agents directly, they could be produced in the target cell, e.g. in a viral vector such as described above or in a cell based delivery system such as described in U.S. Pat. No. 5,550,050 and International Patent Publication Numbers WO 92/19195, WO 94/25503, WO 95/01203, WO 95/05452, WO 96/02286, WO 96/02646, WO 96/38971, WO 96/40959 and WO 97/12635. The vector could be targeted to the target cells. The cell based delivery system is designed to be implanted in a patient's body at the desired target site and contains a coding sequence for the target agent. Alternatively, the agent could be administered in a precursor form for conversion to the active form by an activating agent produced in, or targeted to, the cells to be treated. See, for example, European Patent Application Number 0 425 731A and International Patent Publication Number WO 90/07936.

Further contemplated herein is the use of an Eph-X modified to eliminate at least one N-glycosylation site in the manufacture of a medicament for the treatment of a disease or condition exacerbated by Eph-mediated signaling in a mammalian subject including a human subject, wherein the Eph is selected from EphA1 through A8 and EhB1 through B6 and X is an immunoglobulin or immunoglobulin fragment (e.g. an Fc portion), a protein or protein fragment (e.g. HSA) or a polyether (e.g. PEG).

Taught herein is an Eph-X modified to eliminate at least one N-glycosylation site for use in the treatment of a disease or condition exacerbated by Eph-mediated signaling in a mammalian subject including a human subject, wherein the Eph is selected from EphA1 through A8 and EhB1 through B6 and X is an immunoglobulin or immunoglobulin fragment (e.g. an Fc portion), a protein or protein fragment (e.g. HSA) or a polyether (e.g. PEG).

Still further contemplated herein is the use of an EphA4-Fc modified to eliminate at least one N-glycosylation site in the manufacture of a medicament for the treatment of a disease or condition exacerbated by EphA4-mediated signaling in a mammalian subject including a human subject.

Taught herein is an EphA4-Fc modified to eliminate at least one N-glycosylation site for use in the treatment of a disease or condition exacerbated by EphA4-mediated signaling in a mammalian subject including a human subject, wherein the Eph is selected from EphA1 through A8 and EhB1 through B6 and X is an immunoglobulin or immunoglobulin fragment (e.g. an Fc portion), a protein or protein fragment (e.g. HSA) or a polyether (e.g. PEG).

In yet another aspect, the present invention provides kits comprising the compositions e.g. agents of the present invention. The kits can also contain instructional material teaching the methodologies and uses of the invention, as described herein.

EXAMPLES

The present invention is now further described by the following non-limiting Examples.

Methods

Site Directed Mutagenesis

Nucleotides coding for asparagine (Asn;N) at predicted glycosylation sites 216, 321 and 389 were mutated sequentially to encode glutamine using Quik Change Site Directed Mutagenesis (Agilent Technologies Inc., Santa Clara, Calif.). Briefly, complementary oligonucleotides (Table 2 and 3) flanking the desired mutagenesis sites in human and mouse EphA4-Fc were annealed to codon optimized wt-hEphA4-hFc and wt-mEphA4-mFc template DNA, respectively and extended using PfuTurbo DNA polymerase. Cycling parameters were as follows: 1 cycle 95° C. 30 seconds, followed by 18 cycles 95° C. 30 seconds 55° C. 1 minute 68° C. 8 minutes. Wild-type methylated template DNA was digested with DpnI restriction enzyme prior to transformation into NEB 5-alpha competent E. coli (New England BioLabs). Following expansion of a single colony plasmid DNA was purified using QIAGEN plasmid miniprep kit prior to confirmation of mutagenesis of glycosylation sites by DNA sequencing.

Transient Transfections of Plasmid DNA

HEK293T cells (ATCC, CRL-11268) were cultured in RPMI 1640 Media (GIBCO Life Technologies) supplemented with 10% v/v fetal calf serum (GIBCO Life Technologies), in a humidified atmosphere containing 5% v/v $CO_2$. Plasmid DNA was transfected into HEK293T cells using Lipofectamine 2000 (Invitrogen) according to manufacturer's guidelines. Culture supernatant was harvested on day 6 post transfection and purified by Protein A affinity chromatography using Mab Select agarose matrix (GE Healthcare Life Sciences).

SDS-PAGE Analysis

Protein A purified samples were subjected to SDS-PAGE analysis in the presence of the reducing agent β mercaptoethanol. Briefly, samples were electrophoresed on a 10% v/v SDS polyacrylamide gel followed by staining with Coomassie Brilliant Blue R-250 (Sigma).

EphA4-Fc ELISA Assay

EIA 96 well plates (Costar, Corning Inc.) were coated with 1F9 mAb (3 µg/ml) in 50 mM carbonate buffer pH9.5 overnight at 4° C. prior to blocking with 5% w/v BSA, 0.05% v/v Tween-20 in PBS (PBST) for one hour at room temperature. After three washes with PBST diluted EphA4-Fc analyte was added and incubated for one hour at room temperature. Following three washes with PBST biotinylated 1A7mAb (1 µg/ml) in PBS was added and incubated for one hour at room temperature. After 3 washes with PBST, Ultra Streptavidin-HRP (Thermo Fischer Scientific) diluted 1/500 in PBS was added and incubated one hour at room temperature. Following 3 washes with PBST final detection was via the addition of OPD (SigmaFast [Trademark]) with the end product measured at 492 nm.

Enzymatic Digestion of EphA4-Fc

Production of peptides and glycopeptides from purified EphA4-Fc was accomplished by reducing 115 µg of protein with 10 mM dithiothreitol in 100 mM of $NH_4HCO_3$ buffer with 1% w/v SDS at 4° C. for 18 h. This was followed by further reduction for 2 h at room temperature before cysteine residues were alkylated using 25 mM iodoacetamide for 2 h in the dark. The reduced and alkylated proteins were methanol-precipitated and digested as previously described (Dave et al. (2015) *Curr. Protoc. Protein Sci.* 63:16.13.11-16.13.21). Briefly, the protein sample was co-precipitated with 1 µg of sequencing grade trypsin (Roche Diagnostics GmbH, Mannheim, Germany) using 1 mL of methanol (−20° C.) and incubated at −20° C. overnight. The precipitate was then centrifuged for 15 min 4° C. and the supernatant aspirated. The pellet was washed twice more with 1 mL of −20° C. methanol (90% v/v) and centrifuged before 30 µL of 0.1M triethylammonium bicarbonate was added. The protein was resuspended by gentle vortex-mixing and after a brief centrifugation the protein was incubated at 37° C. for 2 h. Finally, another 2 µg of trypsin was added (final ratio of protein:enzyme, 38:1, w/w) and the digest incubated at 22° C. for a further 6 h. An aliquot of the trypsin digested protein was further digested with Glu-C isolated from *Staphylococcus aureus* V8 (Roche Diagnostics GmbH, Mannheim, Germany) at 37° C. for 12 h (protein:enzyme, 40:1, w/w). After Glu-C digestion the resultant peptides and glycopeptides were desalted with a C18 ZipTip (10 µL pipette tip with a 0.6 µL resin bed; Millipore, Mass., USA) using the manufactures' guidelines before MS analysis.

LC-MS

MS analysis was performed on an Orbitrap Fusion (Trade Mark) Tribrid (Trade Mark) Mass Spectrometer (Thermo Fischer Scientific, San Jose, Calif.) coupled to a nanoACQUITY UPLC (Waters Corporation, MA), where trapping was performed on a Waters C18 2G Symmetry (100 Å, 5 µm, 180 µm×20 mm) trap column and gradient elution on a Waters C18 BEH (130 Å, 1.7 µm particle size, 75 µm×200 mm) column in-line with the trap column. This is referred to as "LC-MS" (Dave et al. (2015) supra) Digested samples were acidified trifluoroacetic acid before MS and 50 ng of the tryptic digest and 100 ng of the tryptic/Glu-C digest were injected for each analysis.

Samples were loaded onto the trap and washed over five min using 98% solvent A (0.1% v/v aqueous formic acid) and 2% solvent B (100% v/v $CH_3CN$ containing 0.1% v/v formic acid) at 15 µL/min. Peptides were subsequently eluted onto the analytical column at flow rate of 0.3 µL/min whilst ramping through a sequence of linear gradients from 2% to 40% solvent B in 60 min, to 70% B over 15 min, to 95% B in 5 min and holding at 95% B for 5 min. Eluates from the analytical column were continuously introduced into the mass spectrometers via a Nanospray Flex [Trade Mark] (NG) ion Source (Thermo Scientific) fitted with a PicoTip (Trade Mark) emitter (coating P200P, tip 10±1 µm, New Objective, MA).

MS survey scans of nUHPLC-fractionated tryptic peptides was performed in the Orbitrap over the range of 300-1800 (m/z) at a resolution of 120K at 200 m/z with an automatic gain control (AGC) target of 200,000 and a maximum injection time of 50 ms. The most intense precursors with charge states of 2-7 and intensities greater than 5000 were selected using an isolation window of 2.5 and fragmented by higher-energy (beam-type) collisional dissociation (HCD) using 30% normalized collision energy. Mass analysis of the fragment ions was performed in the Orbitrap where the resolution was set at 60K with an AGC target of 50,000 and a maximum injection time of 60 ms. Once selected the precursors were excluded for 30 sec.

Data Analysis of Non-Glycosylated Peptides

The MS RAW file generated from the analysis of trypsin digested EphA4-Fc was searched using Proteome Discoverer (v. 1.4.1.14 Thermo Fisher Scientific Inc. Bremen, Germany) and the search engine Mascot (v. 2.5.1, Matrix Science Ltd., London, UK) with the Percolator function against a complete human proteome database (ID: UP000005640 with 70,076 sequences downloaded from the Uniprot webiste) and the EphA4-Fc sequence. The following parameters were used: digestion with trypsin; maximum two missed cleavages; 10 ppm precursor mass tolerance; 0.02 Da fragment tolerance; fixed modification of carbamidomethyl cysteine and dynamic modifications of mono-oxidized methionine and deamidation of asparagine and glutamine. Confident peptide-spectrum matches were assigned using a false discovery rate threshold of 0.05 and two distinct peptides were required for confident protein identifications.

Data Analysis of Glycosylated Peptides

The MS RAW files from the trypsin and trypsin/Glu-C digestions of EphA4-Fc were analyzed with Byonic software (Bern et al. (2002) *Current Protocols in Bioinformatic* John Wiley & Sons, Inc., NJ, USA) using the same mass tolerances and fixed modifications from the Proteome Discoverer search. The enzyme rules were set as cleavage C-terminal to Arg or Lys (trypsin digested sample) or C-terminal to Arg, Lys, Glu or Asp (combined trypsin/Glu-C digestion) and missed cleavages were set to two for the trypsin digested sample and three for the trypsin/Glu-C sample. One glycan attached at an N-linked consensus site (Asn-X-S/T) and one mono-oxidized methionine were allowed per peptide. The peptide output options were changed to "Show all N-glycopeptides" and the spectra were searched against a protein FASTA file containing the sequence for EphA4-Fc and a Byonic N-linked glycan database (309_Mammalian no sodium) with all glycans compositions containing N-glycolylneuraminic acid (NeuGc) removed. After manual inspection of the Byonic results a cut-off score of 100 was chosen for glycopeptides.

The MS RAW files from the trypsin and trypsin/Glu-C digestions of EphA4-Fc were additionally converted to mzML in Proteome Discoverer using a signal to noise (S/N) threshold of zero for analysis with OxoExtract, an in-house software program. OxoExtract selected every MS/MS scan with the oxonium ion $[HexNAc+H]^+$ present within a ±10 ppm mass window. This diagnostic oxonium ion is derived from fragmentation the glycan portion of the glycopeptide and identification of the ion facilitates selection of MS/MS spectra of glycopeptides. The HexNAc oxonium ion and other mono- and oligosaccharide ions (representing Hex, Fuc and NeuAc) can also be used to confirm the composition of the attached glycan. All HexNAc oxonium ion-containing MS/MS spectra selected by OxoExtract were additionally searched for other pre-defined mono- and oligosaccharide oxonium ions and theoretical N-linked glycopeptide fragment ions derived from in-silico digestions of EphA4-Fc. The N-linked glycopeptide fragment ions were calculated using theoretical EphA4-Fc peptides containing the N-linked consensus sequence N-X-S/T and included the peptide+HexNAc$_1$, peptide+HexNAc$_2$ and peptide+HexNAc$_1$dHex$_1$ and peptide b- and y-ions. The peptide+HexNAc$_1$ ion is commonly produced when fragmenting N-linked glycopeptides using HCD and can be used to determine the mass of the peptide moiety. All HexNAc oxonium ion-containing MS/MS spectra that also contained ions matching the m/z of a theoretical peptide+HexNAc$_1$ ion were automatically searched in GlycoMod (Cooper et al. (2001) *Proteomics* 1:340-349) to determine the composition of the attached N-linked glycan. For searches using GlycoMod the peptide mass was calculated from the peptide portion of the theoretical peptide+HexNAc$_1$ ion and a 10 ppm mass tolerance was applied to the observed precursor mass. This data was used to verify glycopeptides assigned by Byonic, confirm the presence of relevant oxonium ions and peptide+HexNAc$_1$ ions, identify glycan compositions with core fucosylation and search for glycopeptides not assigned by Byonic.

The minimum requirement to accept any glycopeptide assignment was the presence of the peptide+HexNAc$_1$ ion or greater than four peptide b- and y-ions. If the sequence of the peptide moiety included a methionine residue at least two peptide b- or y-ions were required to evidence potential oxidation or lack thereof. Relevant glycan oxonium ions had to be present to validate the assigned glycan composition and the elution profile was checked to ensure glycopeptides were eluting at expected retention times.

Size Exclusion Chromatograph

Mutated and wild-type EphA4-Fc were injected onto a TSK-GEL SWXL guard column (6.0 mm ID×400 mm, 7-µm particles) and subsequently eluted onto a TSK-GEL G3000SWXL HPLC column (7.8 mm ID×300 mm, 5-µm particles) using an Agilent 1200 chromatography system. The flow rate was 0.8 mL/min and the mobile phase contained 100 mM sodium phosphate (pH6.8) and 200 mM NaCl. Eluted proteins were monitored by UV absorption (280 nm wavelength). The following standards were used: thyroglobin (670 kDa), bovine γ-globin (158 kDa), ovalbumin (44 kDa), equine myoglobin (17 kDa), and vitamin B$_{12}$ (1.35 kDa) [BioRad].

Analytical Ultracentrifugation

Purified proteins were dialyzed overnight against a buffer containing 10 mM potassium phosphate (pH 7.6). Samples were analyzed using an XL-I analytical ultracentrifuge (Beckman Coulter, Fullerton, Calif.) equipped with an AnTi-60 rotor. Protein samples were loaded in the sample compartment of double-sector epon centrepieces, with buffer in the reference compartment. Radial absorbance data were acquired at 20° C. using a rotor speed of 40,000 rpm and a wavelength of 280 nm, with radial increments of 0.003 cm in continuous scanning mode. The sedimenting boundaries were fitted to a model that describes the sedimentation of a distribution of sedimentation coefficients with no assumption of heterogeneity (c(s)) using the program SEDFIT (Schuck and Rossmanith (2000) *Biopolymers* 54:328-341). Data were fitted using a regularization parameter of p=0.95, floating frictional ratios, and 150 sedimentation coefficient increments in the range of 0.1-15 S.

Numerical Labelling of Amino Acid Positions the three N-glycosylation sites in EphA4 may be numbered with the amino acid sequence including the 19 amino acid leader (signal) sequence as set forth in SEQ ID NO:33, or determined without this sequence. Without the sequence, the sites are N216, N321 and N389. If the leader sequence is included, the positions are N235, N340 and N408, respectively. Both numbering systems are used herein.

TABLE 2

Human EphA4-Fc mutagenesis oligonucleotides

| Amino Acid Position[1] | Oligonucleotide | SEQ ID NO: |
|---|---|---|
| 216 | Sense: 5' GCAGCTGCGTGCAAAACAGCGAAGAG 3' | 17 |
|  | Anti-sense: 5' CTCTTCGCTGTTTTGCACGCAGCTGC 3' | 18 |
| 321 | Sense: 5' ATCAGCAACGTGCAAGAGACAAGCGTG 3' | 19 |
|  | Anti-sense: 5' CACGCTTGTCTCTTGCACGTTGCTGAT 3' | 20 |
| 389 | Sense: 5' CTGGCCCACACCCAATACACCTTCGAG 3' | 21 |
|  | Anti-sense: 5' CTCGAAGGTGTATTGGGTGTGGGCCAG 3' | 22 |

[1]Calculated without the 19 amino acid signal sequence.

TABLE 3

Mouse EphA4-Fc mutagenesis oligonucleotides

| Amino Acid Position[1] | Oligonucleotide | SEQ ID NO: |
|---|---|---|
| 216 | Sense: 5' AGGGGGTCCTGCGTGCAGAACAGTGAAGAAAAG 3' | 23 |
|  | Anti-sense: 5' CTTTTCTTCACTGTTCTGCACGCAGGACCCCCT 3' | 24 |
| 321 | Sense: 5' GATCTCCAACGTGCCAGGAGACTTCTGTG 3' | 25 |
|  | Anti-sense: 5' CACAGAAGTCTCCCTGCACGTTGGAGATC 3' | 26 |

TABLE 3-continued

Mouse EphA4-Fc mutagenesis oligonucleotides

| Amino Acid Position[1] | Oligonucleotide | SEQ ID NO: |
|---|---|---|
| 389[1] | Sense: 5' CTGGCCCACACACAGTACACCTTCGAG 3' | 27 |
| | Anti-sense: 5' CTCGAAGGTGTACTGTGTGTGGGCCAG 3' | 28 |

[1]Calculated without the 19 amino acid signal sequence.

Example 1

Figure 1:
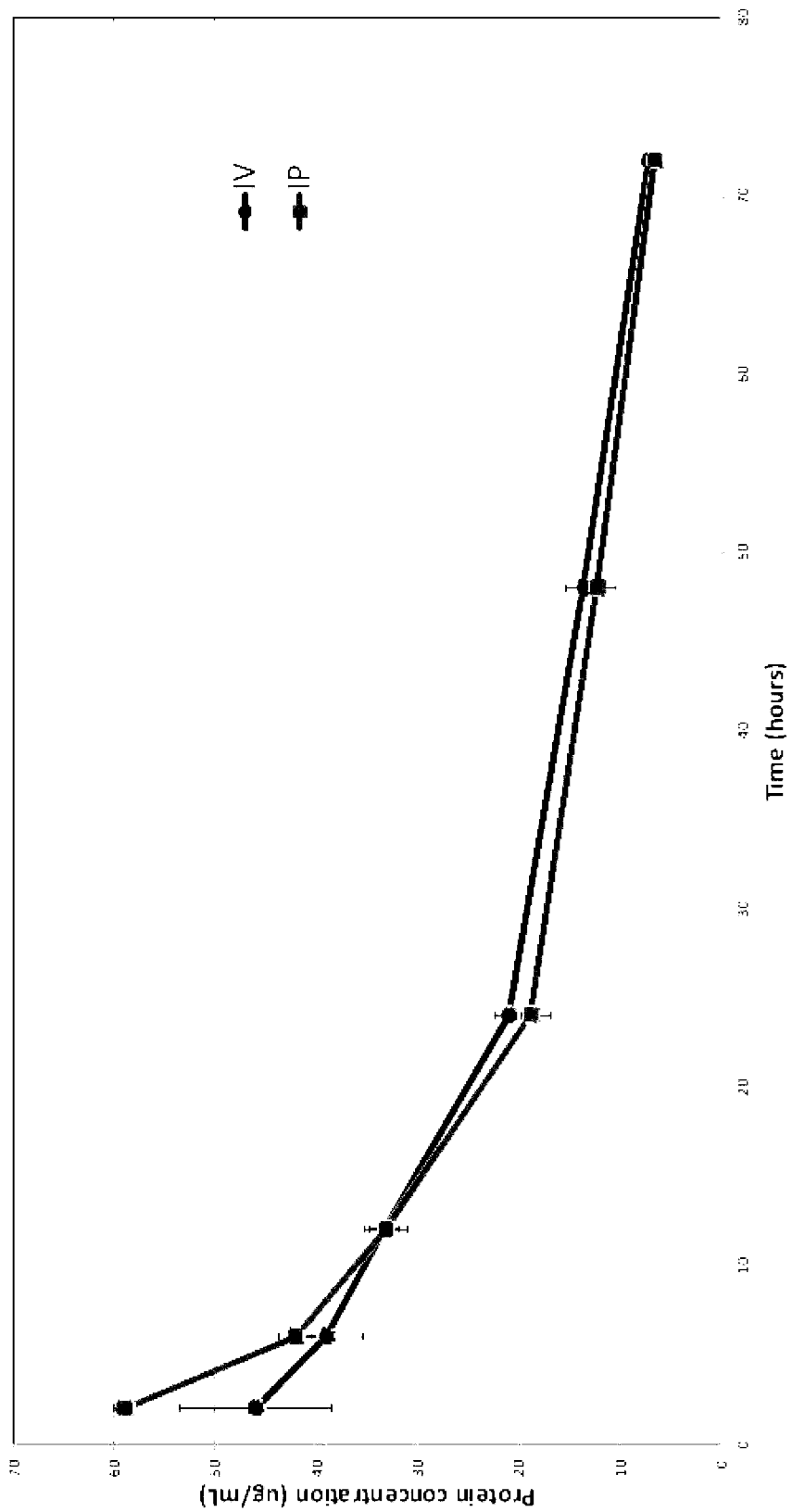
FIG. 1 is a graphical representation of the kinetics of human EphA4-Fc concentration post injection in mice. Measured is serum human EphA4-Fc concentration following a single 20 mg/kg body weight injection, either intravenous (IV) or intraperitoneal (IP).

A Glycosylation Deficient Form of EphA4-Fc Fusion Protein Shows Improved Pharmacokinetic Behavior During studies of the antagonistic effects of EphA4-Fc on EphA4-mediated signaling (e.g. see Goldshmit et al. (2011) supra; Spanevello et al. (2011) supra and Goldshmit et al. (2004) supra) it became evident that the half-life of the fusion protein was shorter than anticipated (FIG. 1). To determine if glycosylation of EphA4-Fc might be a factor in the rapid protein clearance, potential glycosylation sites of EphA4 were analyzed. The online NetGlyN 1.0 and Net-GlycO 1.0 programs were used to examine predicted glycosylation sites for EphA4 and the closely related EphA3 protein where these sites had been previously analyzed (Boyd et al. (1992) *J. Biol. Chem.* 267(5):3262-3267). No 0-linked sites were predicted for either protein. For EphA4 there were three N-linked sites predicted (FIG. 2A) in human EphA4 and corresponding sites in mouse EphA4. The asparagine residues were mutagenized to glutamine at these sites in both mouse and human EphA4-Fc constructs (see Tables 2 and 3 for mutagenic oligos). It was unknown whether this substitution, whilst eliminating the N glycosylation sites, would have any adverse effect on protein structure or function, moreover expression or pharmacokinetics.

Figure 3:
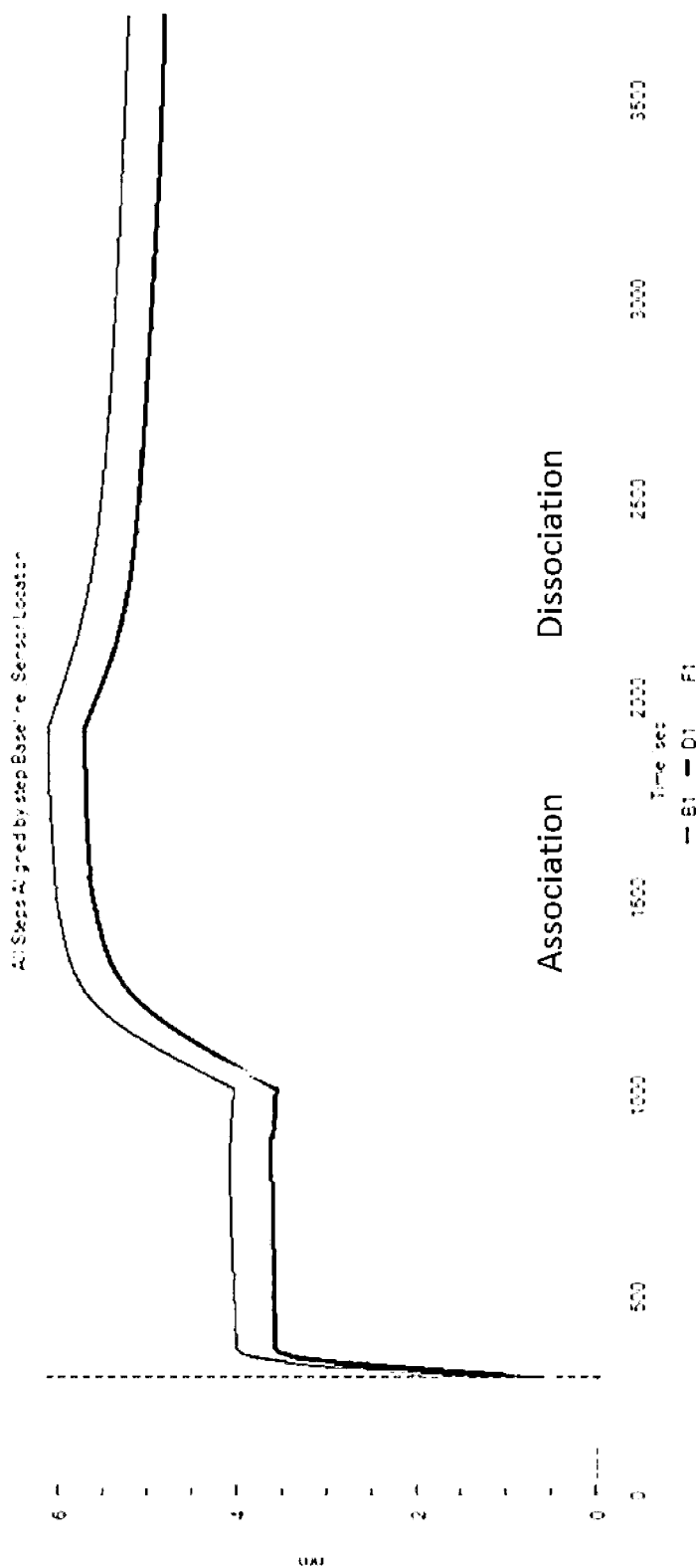
FIG. 3 Binding of EphA4 mutants to ephrin A4. Streptavidin coupled Octet probes were decorated with biotin-conjugated ephrin A4-Fc protein. Individual probes were used to bind WT EphA4-Fc (B1), double mutant (D1) or the triple mutant (F1) proteins. On reaching saturation the probes were exchanged into binding buffer to allow dissociation.

Wild-type and mutant forms of the expression plasmid were transfected into 293T cells and culture supernatants were harvested after 5 days. Recombinant Fc proteins were recovered by protein A sepharose chromatography. In both the mouse and human EphA4-Fc cases there was a slightly lower yield of the triple mutant protein, in different runs this was between 60-70% of the yield of wild-type protein. In each case the triple mutant protein was of lower molecular weight with a mass decrease consistent with deglycosylation of the EphA4 extracellular domain (FIGS. 2B and 2C), compared to the wild-type. A preliminary binding study did show binding of the triple (and a double) mutant to ephrin A4 which was similar to wild-type (FIG. 3).

Figure 4:
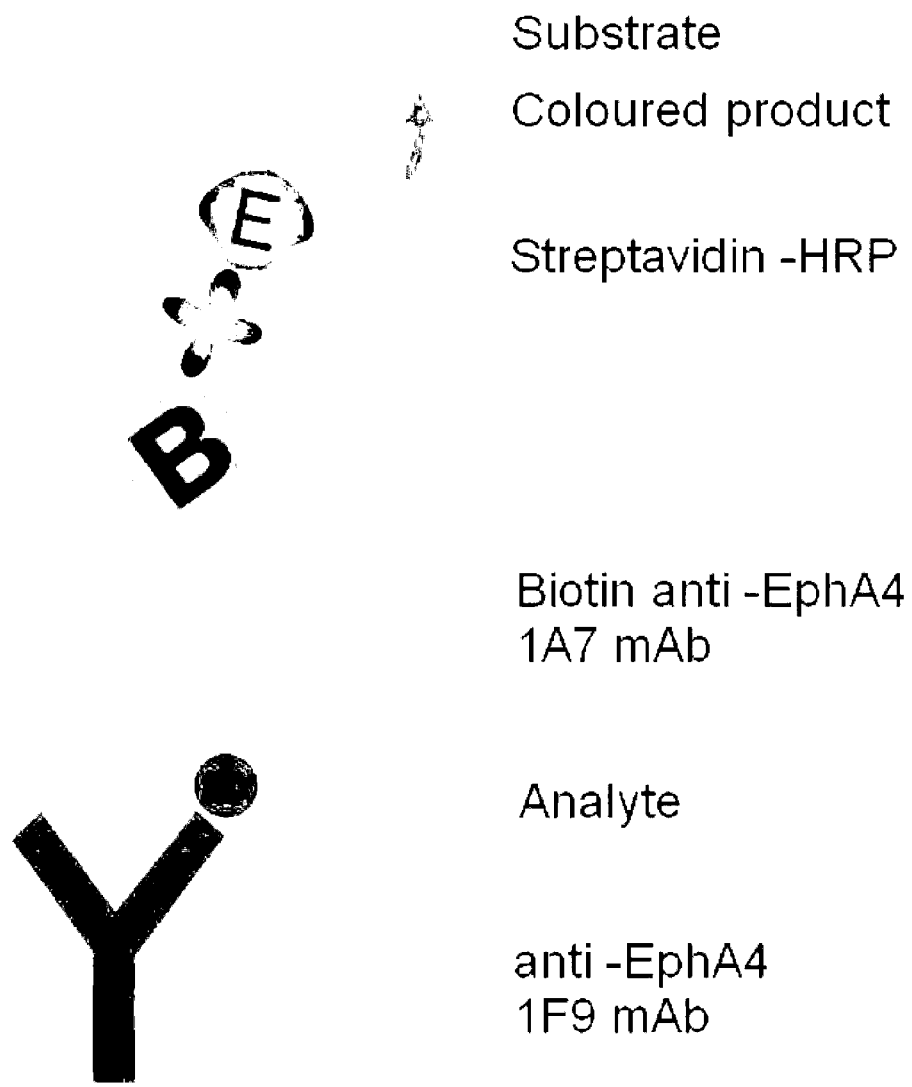
FIG. 4 is a diagrammatic representation of the sandwich ELISA for detection of EphA4 (Analyte).
Figure 5:
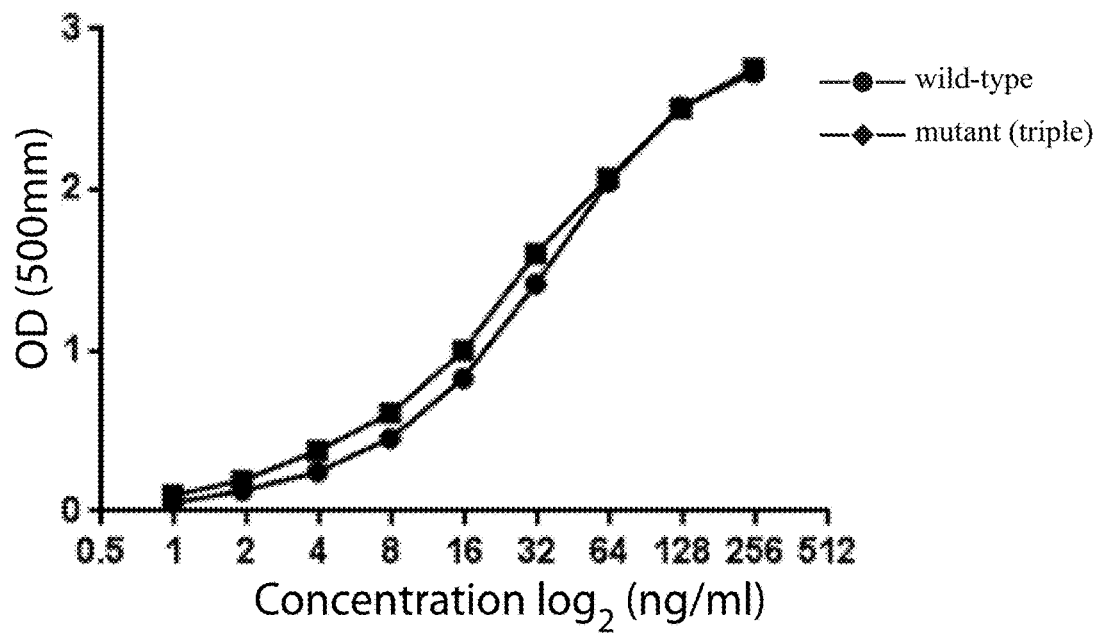
FIG. 5 is a graphical representation of ELISA standard curves of wild-type and mutant human EphA4-Fc, using the assay configuration outlined in FIG. 4.

A sandwich ELISA assay was established using two EphA4 monoclonal antibodies which bind to independent epitopes in the extracellular domain of EphA4 (FIG. 4). As shown in FIG. 5, this assay was equally sensitive in measuring wild-type and mutant human EphA4-Fc.

Figure 6:
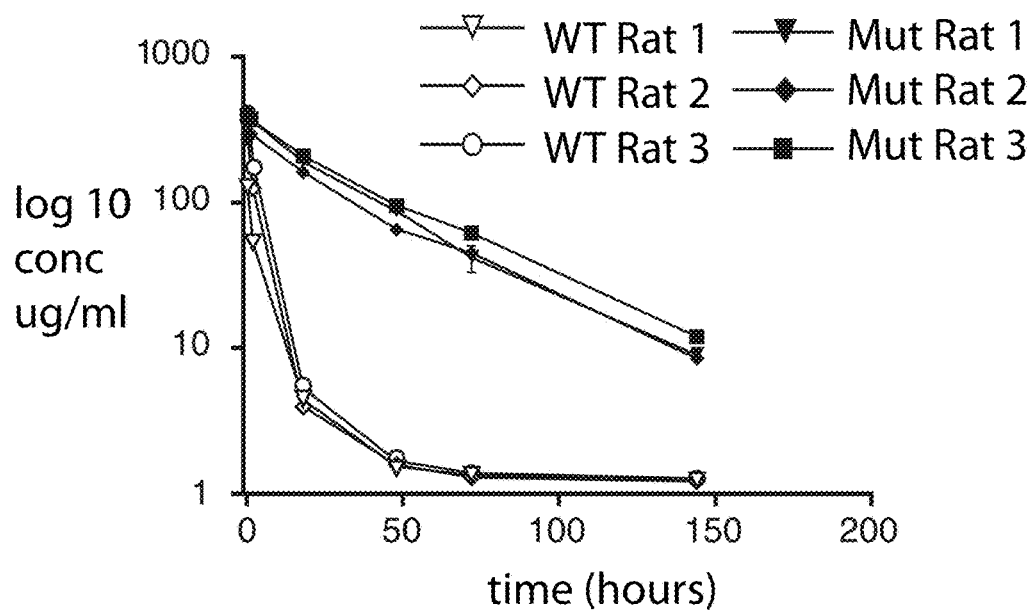
FIG. 6 is a graphical representation of a pharmacokinetic analysis of wild-type and mutant human EphA4-Fc in rat sera.

A pharmacokinetic study was performed in the rat. Wistar rats (6-8 weeks of age) were randomly divided into groups (3 per group) and injected with hEphA4-hFc mutant or wild-type Fc protein at 6 mg/kg through tail vein injections. At different time points: 0.25 hour, 2 hour, 18 hour, 48 hour, 72 hour and day 6 post injection, 150-200 µL of blood was collected by cutting the tips of tails and collection into a Microvette blood collection tube. Following incubation for 30-45 minutes in an upright position, tubes were centrifuged at 11,000 rpm for 10 minutes prior to the removal of the serum. Serum was stored at −80° C. prior to analysis by ELISA (FIG. 6).

Figure 7:
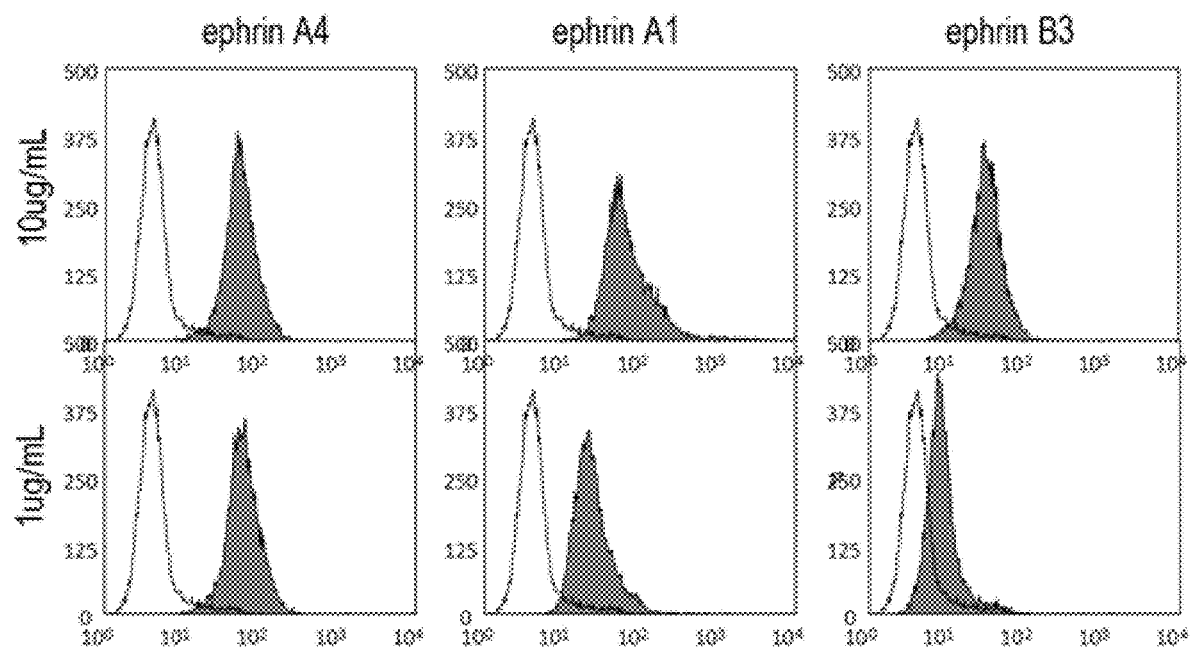
FIG. 7 is a graphical representation showing binding of EphA4-Fc at two different concentrations to ephrin A4 (left panels), ephrin A1 (middle panels) and ephrin B3 (right hand panels) expressing CHO cells.
Figure 8:
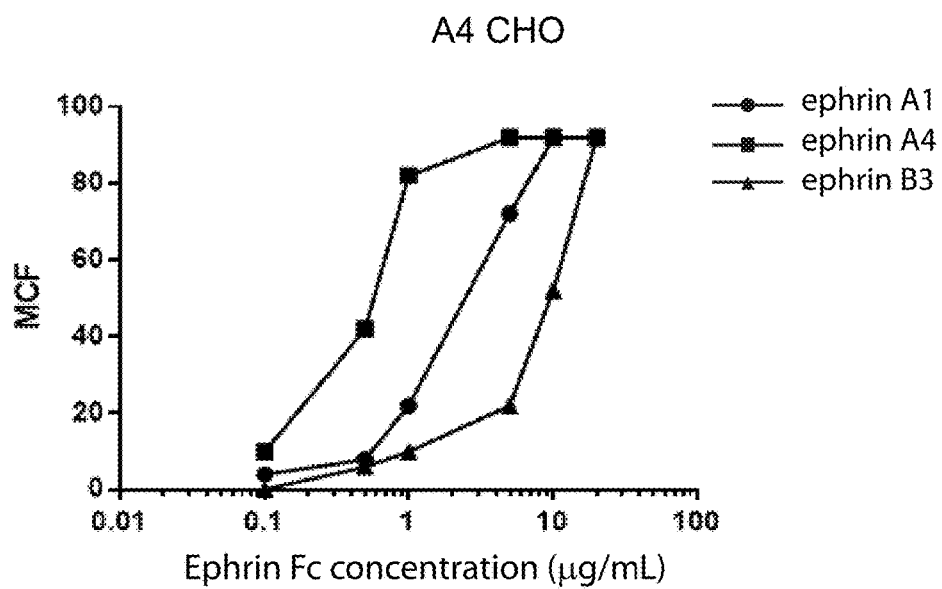
FIG. 8 is a graphical representation of binding of ephrin Fc proteins to CHO cells expressing murine EphA4.

The wild-type protein had a half-life of less than 24 hours and fell below 1 µg/mL before 48 hours. Based on previous experiments using wild-type EphA4-Fc, binding to the key ephrin B3 ligand (FIGS. 7 and 8) at this level is inadequate to block ephrin B3 and indeed insufficient to block lower affinity interactions with ephrin A proteins. In contrast, the mutant protein was still above 10 µg/mL at 6 days indicating this may be effective in competitive blocking over most of this interval. The binding of ephrin A1, ephrin A4-Fc and ephrin B3 Fc to wild-type EphA4 was shown to confirm the affinity of binding and shows an identical pattern to that of soluble EphA4-Fc to immobilized ephrin (FIG. 8).

Figure 9:
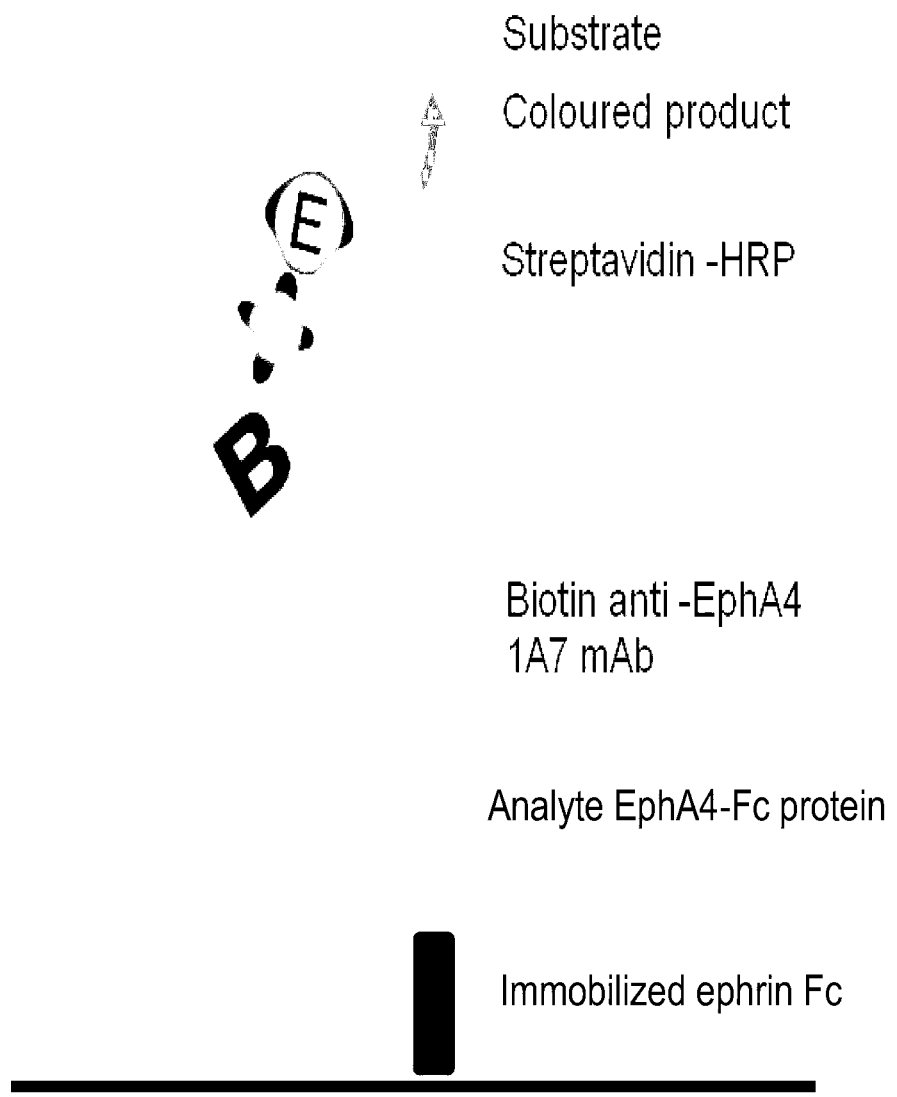
FIG. 9 is a diagrammatic representation of ELISA detection of binding of EphA4 protein to immobilized ephrin.

To analyze the mutant versus wild-type EphA4-Fc binding to ephrin A1, A4 and B3 an ELISA was established in which binding to immobilized ephrins were analyzed (FIG. 9). The results are shown in FIG. 10. It is evident that there is no significant difference in binding, indicating that both proteins have comparable affinities to the three ephrin ligands (a slight apparent increased sensitivity of the mutant protein is likely due to its slightly lower molecular weight).

Example 2

Generation of Modified Eph Molecules

FIGS. 11A through D (SEQ ID NOs:29 through 32) provide amino acid sequence of EphA2, EphA3, EphA4 and EphB4 extracellular domains with the putative N-glycosylation sites marked (see also Table 1). Using the methods described herein, one or more or all the N-glycosylation sites are eliminated then fused or coupled to an immunoglobulin or immunoglobulin fragment (e.g. an Fc portion), a protein or protein fragment (e.g. HSA) or a polyether (e.g. PEG). In an embodiment, the modified Eph molecule is fused to an immunoglobulin (Ig) Fc portion such as IgG1 Fc or IgG4 Fc.

Example 3

Enhanced Half-Life of Non-Glycosylated EphA4-Fc

Sequence Coverage of EphA4-Fc Non-Glycosylated Peptides

Mass spectral analysis of EphA4 Fc digested with trypsin identified 44 proteins when searched against a protein database containing EphA4-Fc and the human proteome. The protein sequence for EphA4-Fc was the top scoring protein with 93% protein coverage. Peptides bearing all four N-linked consensus sites from EphA4-Fc were observed and the spectra were manually investigated to confirm these peptide allocations. One region at the N-terminus of the protein was not sequenced (amino acid residues 1-24) containing the signal peptide. The high level of sequence coverage indicates the correct protein was purified and confirms the expected amino acid sequence. Of the remaining 43 proteins only 19 contained more than two peptides and six had more than 30% sequence coverage. Given the low number of peptide matches and level of sequence coverage it is unlikely these proteins would contribute to observed glycopeptide pool.

N-Linked Glycopeptides Identified from EphA4-Fc

Figure 12:
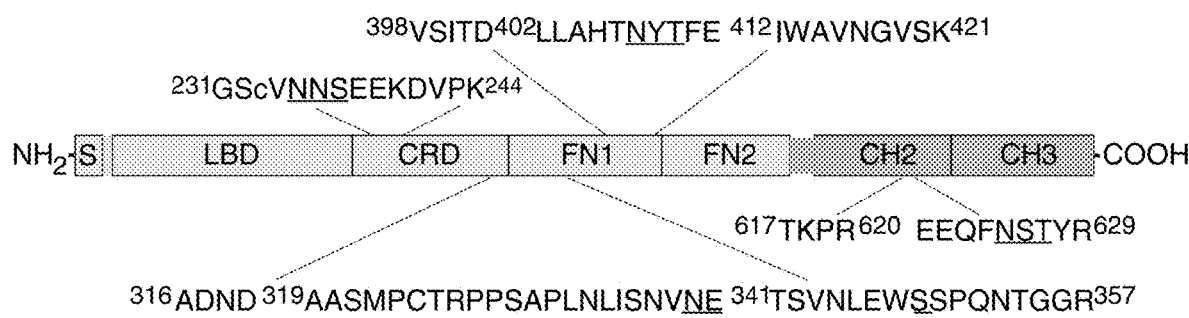
FIG. 12 is a schematic diagram of the EpHA4-Fc protein. The EphA4 region (light grey) and the Fc region (dark grey) are identified (not to scale). The EphA4 signal peptide (S) is located at the N-terminus of the protein and is followed by the ligand-binding domain (LBD), cysteine-rich domain (CRD) and two fibronectin type III repeats (FN1) and (FN2) [Xu et al. (2013) Proc Natl. Acad. Sci. USA 100:14634-14639]. The IgG4 Fc portion of the protein includes the hinge (H) region and the $C_H2$ and $C_H3$ constant immunoglobulin domains. Observed tryptic peptides containing the four N-linked sites N216, N321, N389 and N606 (corresponding to N235, N340, N408 and N625, respectively with the signal sequence [SEQ ID NO: 33]) are displayed with the N-linked consensus sites underlined. The amino- and carboxyl-terminal residues of the tryptic peptides (SEQ ID NOs: 34-37, respectively) have been annotated with the respective amino acid numbers from the EphA4-Fc sequence. Any additional observed proteolytic cleavage by trypsin or Glu-C within the tryptic peptide sequences have also been annotated with the respective amino acid numbers.

The recombinant fusion protein EphA4-Fc contains four N-linked consensus sites (FIG. 12); three are located in the EphA4 portion of the fusion protein, corresponding to sites N235, N340 and N408 in the extracellular domain of full length EphA4 (UniProt ID: P54764-1). The fourth N-linked site of recombinant EphA4-Fc, site N625, resides within the IgG4 Fc domain of the protein and corresponds to N297 in the $C_H2$ domain of each heavy chain of all IgG subclasses (Zauner et al. (2013) *Mol. Cell. Proteomics* 12:856-865). To comprehensively investigate site specific glycan heterogeneity, a combination of enzymes were used to digest EphA4 Fc before analysis by mass spectrometry (MS). Initial digestion was with trypsin, which cleaves peptides bonds C-terminal to lysine (Lys/K) and arginine (Arg/R) except where proline resides on the carboxyl side of the cleavage site. The trypsin digested sample was then subjected to digestion with Glu-C which cleaves peptide bonds C-terminal to glutamic acid (Glu/E) and at a lower rate C-terminal to aspartic acid (Asp/D) [Breddam and Meldal (1992) *European Journal of Biochemistry FEBS* 206:103-107]. Both the trypsin and trypsin/Glu-C digested samples were analyzed in separate chromatographic MS/MS experiments. Mass spectral analysis of the digests of EphA4 Fc enabled identification of 212 intact glycopeptides containing one of the four potential N-linked glycosylation sites. Due to different enzyme digestions and cleavage events the identified glycopeptides contained one of twelve peptide moieties with spanning an N-linked consensus sites.

Glycan Composition Identified at Each N-Linked Site of EphA4-Fc

Figure 13:
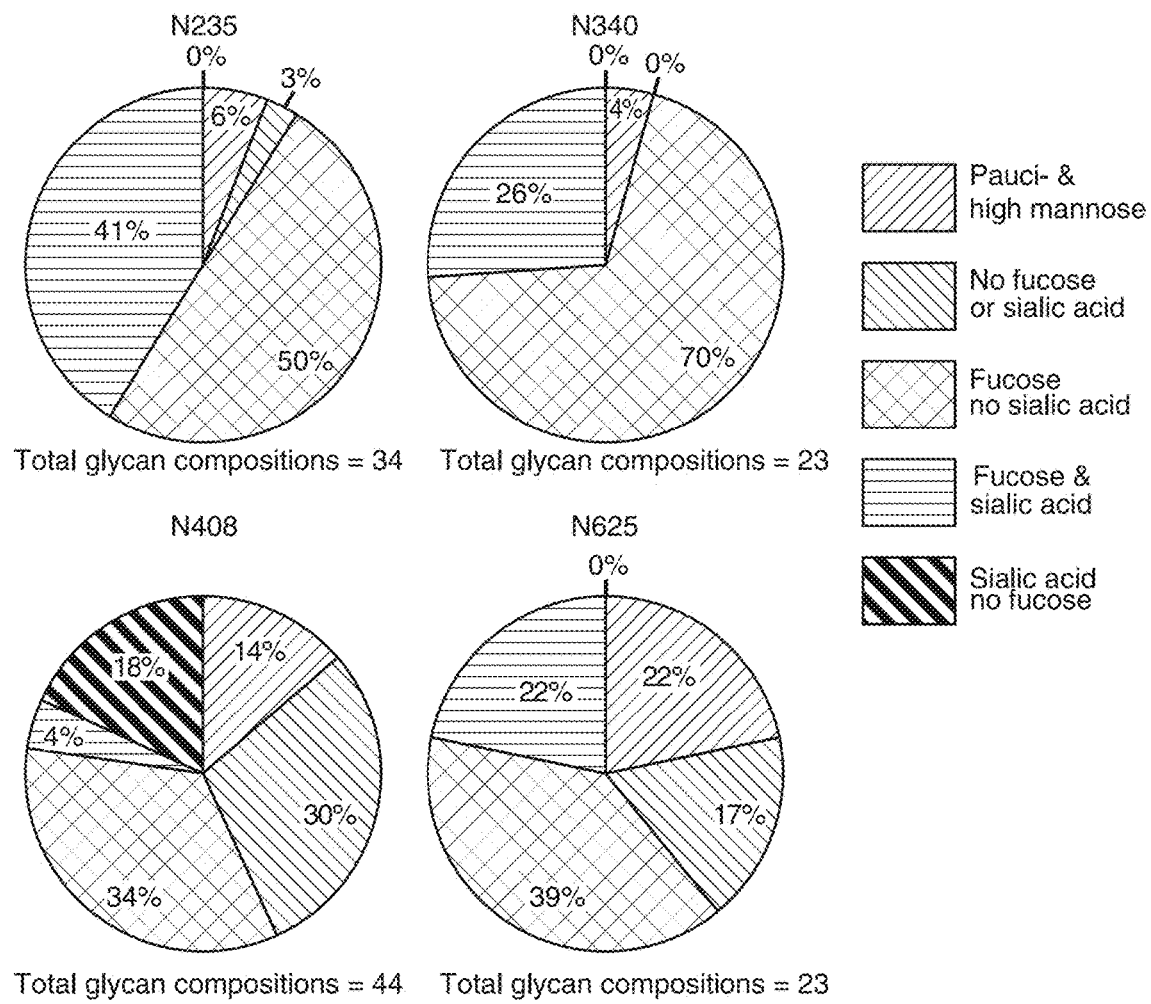
FIG. 13 is a diagrammatic representation of composition of glycans at each N-linked site of EphA4-Fc. Qualitative distribution of the glycan compositions observed from EphA4-Fc at N-linked sites N216, N321, N389 and N606 (corresponding to N235, N340, N408 and N625, respectively with the signal sequence [SEQ ID NO:33]).

A total of 69 glycan compositions were observed across the four N-linked sites. When considering each glycan composition only once at each N-linked site there was a total of 34, 23, 44 and 23 glycans detected at sites N235, N340, N408, and N625 (calculated with the 19 amino acid leader sequence), respectively. It should be noted that particular vertebrate monosaccharides are isomeric (e.g. GalNAc/GlcNAc or Man/Gal/Glc), thus mass spectral analysis of intact glycopeptides cannot distinguish between monosaccharide isomers in the attached glycans. Nomenclature has been implemented in this work to represent this ambiguity, where N-Acetylhexosamine (HexNAc) and hexosamine (Hex) are used to represent GlcNAc/GalNAc and Man/Gal/Glu, respectively. Deoxyhexose (dHex) represents the isomeric monosaccharides fucose (Fuc) and xylose; in this paper dHex is assumed to be Fuc from known rules of mammalian N-linked biosynthesis and observed N-linked glycans produced in HEK cells (Moremen et al. (2012) *Nat. Rev. Mol. Cell Biol* 13:448-462; Andre et al. (2007) *Proteomics* 7:3880-3895). The qualitative difference of glycan compositions at each N-linked site can be seen in FIG. 13. Between the four N-linked sites there was a clear difference in the number of complex and hybrid structures that were fucosylated. At sites N235, N340 and N625 (calculated with the presence of the 19 amino acid leader sequence) fucosylation was observed on 97%, 100% and 78% of hybrid and complex structures, respectively. While at site N408 only 45% of hybrid and complex structures were assigned compositions containing fucose. The proportion of glycans with sialylation (N-Acetylneuraminic acid/NeuAc) was highest at site N235 (41%) followed by sites N340 (26%), N408 (22%) and N625 (22%).

Deletion of Glycosylation Sites by Directed Mutagenesis

Figure 14:
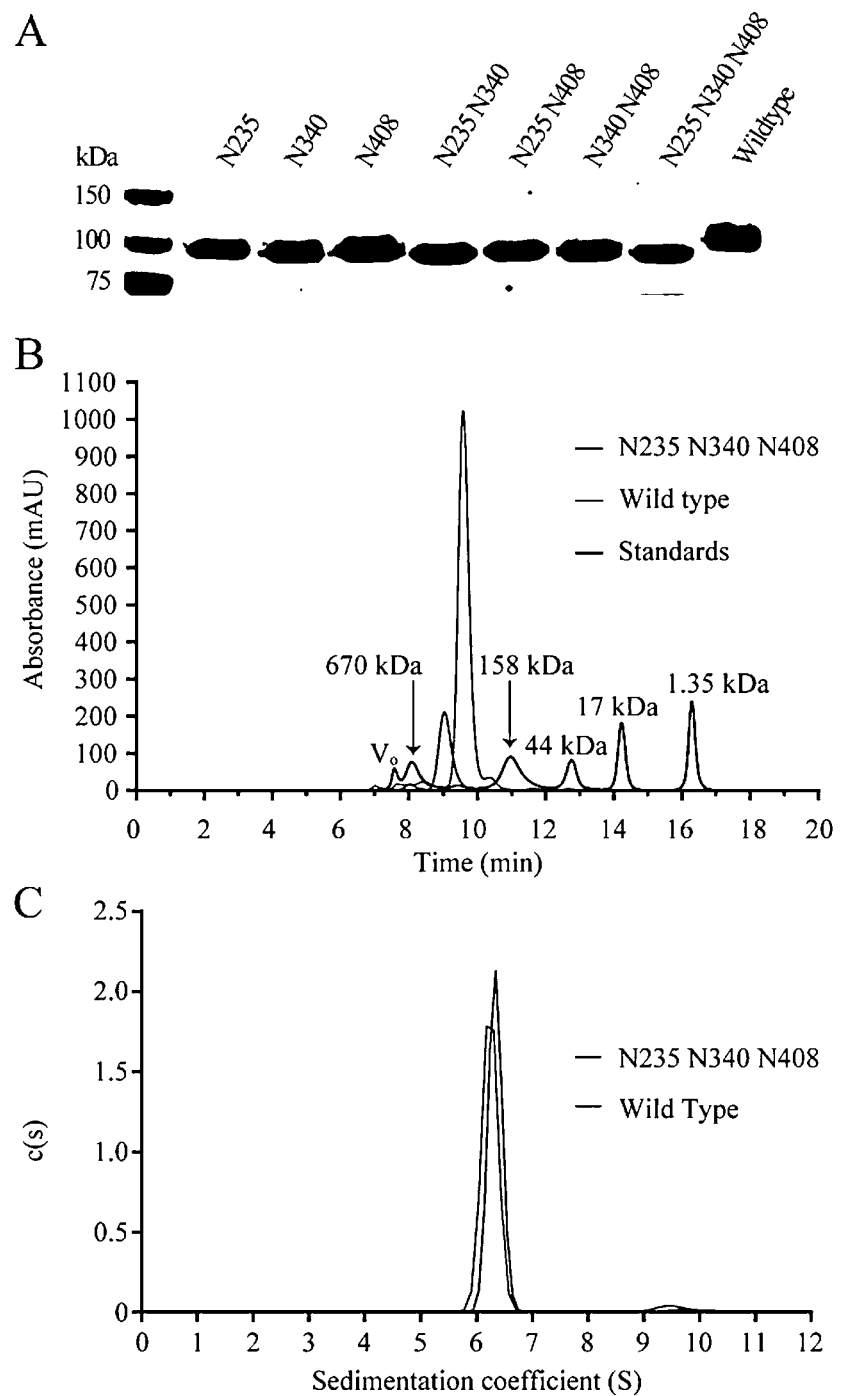
FIG. 14 is a diagrammatic representation of: A) SDS-PAGE analysis of reduced, protein A purified single, double and triple deglycosylated and wild-type human EphA4-Fc proteins. B) SEC and C) SV-AUC sedimentation profiles reveal a single predominant peak for both the triple mutant (red) and wild-type (blue) human EphA4-Fc proteins indicating the absence of significantly different sized protein species. The chromatogram for the molecular weight standards (black) has been included in the SEC profile with the mass of the standards noted above the respective peak (Thyroglobin—670 kDa; bovine γ-globin—158 kDa; ovalbumin—44 kDa; equine myoglobin—17 kDa and vitamin $B_{12}$—1.35 kDa).

To analyze the effect of glycosylation on protein function, the human EphA4-Fc expression vector was systematically mutated such that the codons for the three key asparagine residues in the EphA4 extracellular domain were replaced with codons for glutamine residues similar to Example 2. The resulting single, double and triple mutant vectors were transfected into HEK293 cells and expressed proteins recovered from cell supernatants using protein A affinity chromatography. As shown in FIG. 14A, the mutated proteins showed progressively lower molecular weights consistent with the loss of sugar moieties. Conformational differences and the oligomeric state of the wild-type and mutant EphA4-Fc proteins were assessed by size exclusion chromatography (SEC) [FIG. 14B] and sedimentation velocity analytical ultracentrifugation (SV-AUC) [FIG. 14C]. During SEC there was a slight shift in the elution times with the mutant EphA4-Fc eluting at 9.58 min while the wild-type eluted at 9.03 min. Analysis of SV-AUC data revealed a narrow distribution of apparent sedimentation coefficients with predominant peaks at ~6.3 S for the wild-type and ~6.2 S for the mutant. This confirmed the homogeneity observed in SDS-PAGE and SEC. Molecular weights estimations of 174 kDa and 156 kDa were given for the wild-type and mutant, respectively. These estimations are in agreement with those calculated for a homodimer of EphA4-Fc (~168 kDa), with the lower molecular weight of the mutant consistent with removal of the N-glycans present on the wild-type. The fitted frictional ratios indicated that the proteins have an elongated conformation and a slightly higher ratio was observed for the wild-type protein compared to the mutant (1.76 versus 1.66).

Ligand-Binding Activity of Deglycosylated and Wild-Type EphA4-Fc

Figure 15:
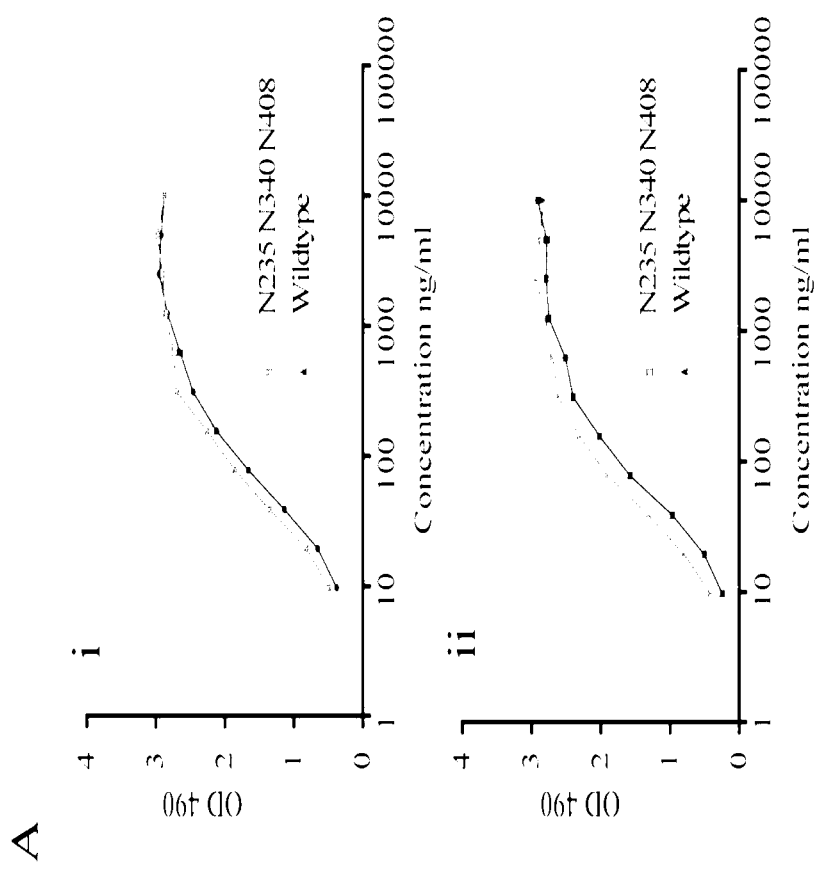
FIGS. 15A through 15C are a graphical representations of ligand-binding of mutagenic deglycosylated and wild-type human EphA4-Fc proteins.

Analysis of the mutant and "wild-type" EphA4 Fc proteins was carried out using three methods: ephrin-binding ELISA (FIG. 15A), Octet biosensor analysis (FIG. 15B) and flow cytometric analysis of binding to ephrin-expressing cell lines FIG. 15C). All of these techniques showed that the mutant proteins retained the ability to bind to ephrin ligands with a comparable affinity to the un-mutated EphA4-Fc protein. The same procedure was carried out using a vector encoding an EphA4-mouse Fc protein and again the mutations were shown not to affect function. Taken together, the data implied that a concentration of >1 µg/mL would saturate all ephrin A ligands and that >10 µg/mL would be sufficient to saturate ephrin B3 sites.

Example 4

Pharmacokinetic Analysis of EphA4-Fc Glycosylation Mutants

To assess if glycosylation was determinative of in vivo clearance, the pharmacokinetic behavior of un-mutated human EphA4-Fc protein and of the single, double and triple mutant proteins was investigated in mice. All of the mutations resulted in some prolongation of in vivo half-life but this was least pronounced in single mutants, more robust with double mutants and most prolonged when all three glycosylation sites were deleted. Comparing the pharmacokinetics of the triple mutant against the wild-type protein directly in rats (performed in triplicate), a more dramatic prolongation of half-life of the mutant protein was observed, whereas the un-mutated protein was cleared very rapidly. It is evident that the triple mutant protein exhibits a simple log-linear clearance in contrast to the un-mutated protein which shows a more complex rapid initial clearance followed by a plateau, consistent with the heterogeneity of glycosylation at the predicted asparagine linkage residues. The "wild-type" and mutated mouse EphA4-Fc protein were also analyzed in mice. As with the human EphA4-Fc, the triple mutant protein showed a greatly extended in vivo half-life.

Example 5

Role of N-Glycosylation in EphA4-Fc

Studies have shown that EphA4-Fc is cleared rapidly, requiring frequent dosing in mouse and rat SCI studies (Goldshmit et al. (2011) supra). To explore the possible involvement of glycosylation in this rapid clearance the glycosylation of EphA4-Fc was analyzed (Examples 2-4). Mass spectral analysis of intact glycopeptides derived from trypsin digested and trypsin/Glu-C digested EphA4-Fc confirmed that the four predicted N-linked sites within the fusion protein were glycosylated. Consistent with prediction, no O-linked glycosylation sites within the EphA4 region of the protein were detected. Furthermore, peptides bearing all four N-linked sites were also observed without glycosylation indicating that within the pool of EphA4-Fc proteins the N-linked sites are utilized but they are not always glycosylated. Qualitatively, the proportion of glycans with sialylation was highest at site N235 (41%) followed by sites N340 (26%), N408 (22%) and N625 (22%). The higher degree of sialylation observed at site N235 may reduce the level of asialoglycoprotein or mannose receptor-mediated clearance, thus accounting for the minimal impact of mutating this site on clearance. These amino acid positions are based on the presence of the 19 amino acid N-terminal leader sequence.

The purity, conformations and oligomeric states of the mutant and wild-type EphA4-Fc proteins were analyzed by SDS-PAGE, SEC and SV-AUC (FIGS. 14A-C, respectively). As judged by sedimentation velocity both the mutant and wild-type EphA4-Fc appear to be stable dimers with molecular weights in reasonably close agreement to those calculated, when taking into account N-glycan differences. Interestingly, the SEC elution times of the mutant and wild-type (9.58 and 9.03 mins, respectively) are significantly higher than the expected elution based on theoretical molecular weight, which should correspond to bovine γ-globin (158 kDa, elution time of 11.0 mins), suggesting both molecules have a non-globular structure. Taken together, the results of SEC and SV-AUC indicate that wild-type EphA4 has a slightly larger hydrodynamic volume or more elongated conformation (consistent with earlier elution in SEC and a higher fitted frictional ratio in SV-AUC).

The wild-type EphA4-Fc exhibited rapid clearance in the first 24-48 hours, accounting for the vast majority of circulating drug, but then plateaued for the remaining time points. This may be due to preferred clearance of EphA4-Fc variants containing asialylated N-glycans, while those structures containing sialylated glycans or no N-glycosylation were retained in vivo. The pharmacokinetic studies show a pronounced effect of glycosylation on the protein half-life in vivo. Whilst the mutation of individual sites showed a variable effect, the protein with a completely deglycosylated EphA4 region showed the greatest prolongation of availability. Importantly a dose of 20 mg/kg was able to sustain a serum concentration which, based on a concentration of 10 μg/mL being able to bind maximally to all ephrin A and ephrin B ligands, would block all ephrin sites for 6-7 days. This is highly significant as it provides the potential to enable dosing with EphA4-Fc at weekly intervals as opposed to the glycosylated protein which would need to be delivered every 1-2 days to be effective as a decoy receptor drug.

The literature is inconsistent with respect to the role glycosylation plays in protein functionality and pharmacokinetics. Interestingly, deglycosylation of Ephrin A1 had a negative impact on its binding affinity with EphA2 while production of non-glycosylated Ephrin A1 resulted in misfolding of the protein (Fegula et al. (2013) supra). This effect has also been observed in other proteins where mutating N-glycosylation sites results in significant losses of protein expression (Takahaski et al. (2008) supra; Mishina et al. (1985) Nature 313:313, 364-369). Hence, it was unclear what the affect would be of modifying glycosylation patterns on proteinaceous Eph signaling antagonists. Contrary to the growing body of studies showing the benefit of maintaining or introducing N-linked sites in protein therapeutics, the present invention is predicated in part on the interesting result where functionality was preserved and pharmacokinetic properties were markedly improved after the elimination of three N-linked sites. Furthermore, the results provide an insight into the role of EphA4 N-linked glycosylation, revealing that N-linked consensus sites are not essential for ligand binding properties.

Example 6

Pre-Clinical EphA4-Fc Motor Neuron Disease (MND) Data Showing Efficacy

EphA4-Fc administration in the MND SOD1$^{G93A}$ mouse model improves behavioral performance. The systemic administration of EphA4-Fc to SOD1$^{G93A}$ mice was investigated. Briefly, SOD1$^{G93A}$ mice were treated with either the murine homolog of the EphA4-Fc fusion or a saline control. Functional tests were performed on a weekly basis with the experiment terminated at week 24. Fore and hind-limb grip strength were assessed, as well as balance and coordination using the RotaRod test. Treated mice had significantly greater hind-limb grip strength at 18, 19, 20 and 21 weeks of age, compared with control groups. Treated mice also had increased behavioral performance in the RotaRod test compared to controls, during weeks 18 to 24, with the increase reaching statistical significance by week 20 (FIGS. 16A and B). These results should be examined in the light of challenges associated with the SOD1$^{G93A}$ model (Vaqueur et al. (2013) Nat Rev Drug Disocv 12:287-305; Kobeleva et al. (2013) Neurodgene Dis. Manag. 3:525-537) in particular the degree of disease severity induced by the SOD1 mutation. Given the substantial loss of induced motor function, there is a statistically significant difference in the treatment group. This experiment has been repeated 4 times with individual cohorts of animals and in all cases significant improvement in behavioral performance has been seen with EphA4-Fc treatment.

Example 7

EphA4 Genetic Ablation MND Model

To assess the full impact of blocking EphA4 signaling on MND the EphA4 gene was deleted in motor neurons of SOD1$^{G93A}$ mice, providing an insight into both the involvement of EphA4 in SOD-1 dependent disease and the relative effectiveness of the EphA4-Fc therapy. This was performed by crossing 3 strains of mice to establish a cell type-specific EphA4 gene-deletion system in SOD1$^{G93A}$ mice, which could assess the effect of specific genetic ablation of EphA4 on MND progression (SOD1$^{G93A}$ EphA4$^{flox/flox}$ and ChAT-Cre$^{KI/KI}$). EphA4$^{flox/flox}$ mice have a conditional allele of EphA4 with a floxed exon 3 (Hermannetal (2010) *Genesis* 48:101-105). When EphA4$^{flox/flox}$ mice are crossed with ChAT-Cre$^{KI/KI}$ mice, Cre-mediated excision of exon3 splicing exon2 to exon4 causes a frameshift in the downstream sequence, producing a null of EphA4 gene in ChAT-expressing cells. This conditional depletion of EphA4 was built on the SOD1$^{G93A}$ mice background. The breeding strategy requires four rounds of breeding and the numbers are based on production of 6 animals per litter, achieving the expected ratio of genotypes.

Figure 17:
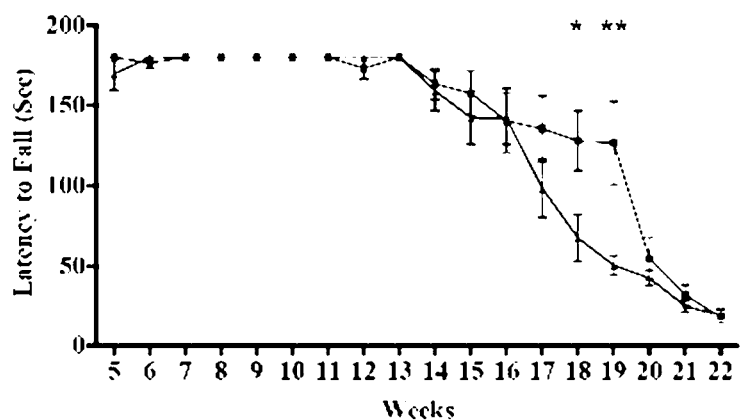
FIG. 17 is a graphical representation showing that a heterozygous conditional knockout EphA4 in SOD1$^{G93A}$ mice exhibited significantly improved behavioral performance in the rota-rod test (* p<0.05, **p<0.01; Abbreviation: EphA4$^{F/W}$; SOD1$^{G93A}$, EphA4$^{flox/WT}$×ChAT-Cre$^{KI/KI}$× SOD1$^{G93A}$; EphA4$^{WT/WT}$; SOD1$^{G93A}$, EphA4$^{flox/flox}$×ChAT-Cre$^{WT/WT}$×SOD1$^{G93A}$).

The body weight and behavioral performance among EphA4$^{flox/flox}$×ChAT-Cre$^{KI/KI}$×SOD1$^{G93A}$ EphA4$^{flox/WT}$×ChAT-Cre$^{KI/KI}$×SOD1$^{G93A}$ mice, and EphA4$^{flox/flox}$×ChAT-Cre$^{WT/WT}$×SOD1$^{G93A}$ mice. Included is a conditional depletion of EphA4 in wild-type (C57BL/6J) mice and wild-type mice into this study as control groups, which were EphA4$^{flox/flox}$×ChAT-Cre$^{KI/KI}$×C57 and EphA4$^{flox/flox}$×ChAT-Cre$^{WT/WT}$×C57 mice. Disease onset and progression are monitored by measuring weight after the age of 5 weeks. Behavioral performance is assessed beginning at 8 weeks, then weekly monitoring using the Rota-Rod and hind-limb grip strength test. The tests are performed blinded to groups. Motor neuron survival is assessed by immunohistochemical staining in lumbar enlargement of spinal cords with an anti-ChAT antibody and ChAT positive cells (motor neurons) counted. The number of motor neurons is directly associated with the behavioral performance. Data obtained indicated a decline of the RotaRod test values starting at week 14, however, unlike the EphA4$^{flox/flox}$×ChAT-Cre$^{WT/WT}$×SOD1$^{G93A}$ mice, the performance of EphA4$^{flox/WT}$×ChAT-Cre$^{KI/KI}$×SOD$^{G93A}$ mice declined much slower, resulting in significant differences at week 18 and 19 (FIG. 17).

Figure 18:
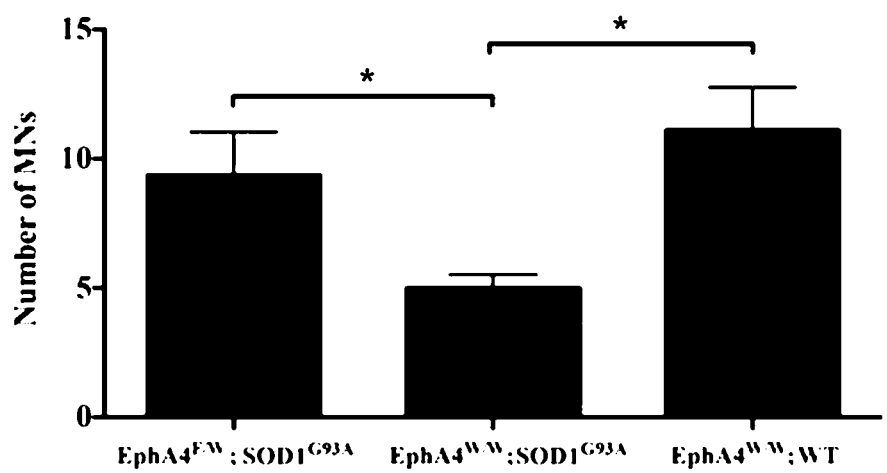
FIG. 18 is a graphical representation showing heterozygous conditional knockout EphA4 in SOD1$^{G93A}$ mice exhibit preservation of lumbar motor neurons at 17 weeks.

When comparing the motor neuron counts in the same experiment, the heterozygote EphA4-depleted SOD1 mice exhibited preservation of lumbar motor neurons at 17 weeks compared to wild-type controls (FIG. 18).

Example 8

Effect of Mutation of Glycan Sites on EphA2-Fc

Methods
Plasmid Preparation of EphA2-Fc

Codon optimized human EphA2-Fc DNA was synsthesized, cloned and sequence verified by (GenScript USA Inc.) with the nucleotides coding for asparainge (ASn; N) at predicted glycosylation sites 407 and 435 encoding glutamine. Plasmid was transformed into NEB 5-alpha competent *E. coli* (New England BioLabs), expanded from a single colony, with DNA purified using QIAGEN plasmid midiprep kit.

Transient Transfections of Plasmid DNA

HEK293T cells (ATCC, CRL-11268) were cultured in RPMI 1640 Media (GIBCO Life Technologies) supplemented with 10% v/v fetal calf serum (GIBCO Life Technologies), in a humidified atmosphere containing 5% v/v CO$_2$. Plasmid DNA was transfected into HEK293T cells using Lipofectamine 2000 (Invitrogen) according to manufacturer's guidelines. Culture supernatant was harvested on day 6 post transfection and purified by Protein A affinity chromatography using Mab Select agarose matrix (GE Healthcare Life Sciences).

Pharmacokinetic of EphA4-Fc on Rats

Rats were randomly divided into two groups, injected with either mutant EphA2-Fc or wild-type EphA2-Fc at a concentration of 1 mg/kg through the tail vein. Then, 300-400 µl of blood samples were collected by cutting the tips of rat tails at different time points after the treatment, namely 2 h, 18 h, 48 h and 6 d. After each blood collection, all samples were incubated in an upright position at room temperature for 1 h to allow clotting, and then centrifuged for 10 min at 11000 rpm. The serum was stored at −80° C. for ELISA assay.

EphA2-Fc ELISA Assay

EIA 96 well plates (Costar, Corning Inc.) were coated with 4B3 mAb (3 µg/ml) in 50 mM carbonate buffer pH9.5 overnight at 4° C. prior to blocking with 5% w/v BSA, 0.05% v/v Tween-20 in PBS (PBST) for one hour at room temperature. After three washes with PBST diluted EphA4-Fc analyte was added and incubated for one hour at room temperature. Following threewashes with PBST biotinylated 1F7 mAb (1 µg/ml) in PBS was added and incubated for one hourat room temperature. After 3 washes with PBST, Ultra Streptavidin-HRP (Thermo Fischer Scientific) diluted 1/500 in PBS was added and incubated one hourat room temperature. Following 3 washes with PBST final detection was via the addition of OPD (SigmaFast [Trademark]) with the end product measured at 492 nm.

Results

The results are shown in FIG. 19. Mutation of the EphA2 glycan sites did not result in a pharmokinetic (PK) improvement for this molecule. These data highlight the non-predictability of glycan site removal on PK.

→ Mutant Rat1
→ Mutant Rat2
→ WT Rat1
→ WT Rat2
→ WT Rat3

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Altschul et al. (1997) *Nucl. Acids. Res.* 25(17):3389-3402
Andre et al. (2007) *Proteomics* 7:3880-3895
Arocho et al. (2011) *Cell. Mol. Neurobiol.* 31:1057-1069
Ausubel et al. (1994-1998) In: *Current Protocols in Molecular Biology*, John Wiley & Sons Inc.
Bern et al. (2002) *Current Protocols in Bioinformatic* John Wiley & Sons, Inc., NJ, USA
Bowden et al. (2009) *Structure* 17:1386-1397
Boyd et al. (1992) *J. Biol. Chem.* 267(5):3262-3267
Boyd et al. (2014) *Nat. Rev. Drug Discovery* 13:39-62
Breddam and Meldal (1992) *European Journal of Biochemistry FEBS* 206:103-107
Cooper et al. (2001) *Proteomics* 1:340-349
Coulthard et al. 2014) *AMJ Path* 18:1493-1503

Dave et al. (2015) *Curr. Protoc. Protein Sci.* 63:16.13.11-16.13.21
Egleton and Davis (1997) *Peptides* 18:1431-1439
Elliot et al. (2003) *Nature Biotechnology* 21(4):414-421
Fabes et al. (2006) *Eur. J. Neurosci.* 23:1721-1730
Ferluga et al. (2013) *J. Biol. Chem.* 288(25):18448-18457
Fix (1996), *Pharm Res* 13:1760-1764
Goetze et al. (2011) *Glycobiology* 21(7):949-959
Goldshmit et al. (2004) *J. Neurosci.* 24:10,064-10,073
Goldshmit et al. (2011) *PLos ONE* 6:e24636
Hermannetal (2010) *Genesis* 48:101-105
Jones et al. (2007) *Glycobioloty* 17(5):529-540
Kent (2002) *Genome Res* 12:656-664
Kobeleva et al. (2013) *Neurodgene Dis. Manag.* 3:525-537
Langer (1990) *Science* 249:1527-1533
Langmead et al. (2009) *Genome Biol* 10:R25
Li and Durbin (2010) *Bioinformatics* 26: 589-595
Mishina et al. (1985) *Nature* 3/3:313, 364-369
Moremen et al. (2012) *Nat. Rev. Mol. Cell Biol* 13:448-462
Patton (1998) *Nat Biotech* 16:141-143
Putney and Burke (1998) *Nat Biotech* 16:153-157
Qin et al. (2010) *J. Biol. Chem.* 285:644-654
Remington's Pharmaceutical Sciences, 18th Edition, Mack Publishing Company, Easton, Pa., 1990
Samanen et al. 1996) *J Pharm Pharmaco* 148:119-135
Sayani and Chien (1996) *Crit Rev Ther Drug Carrier Syst* 13:85-184
Schuck and Rossmanith (2000) *Biopolymers* 54:328-341
Spanevello et al. (2013) *J. Neurotrauma* 30:1023-1034
Takahashi et al. (2008) *Biochimica et Biophysica Acta* 1780:520-524
Stork et al. (2008) *J Biol Chem* 283:7804-7812
Vaqueur et al. (2013) *Nat Rev Drug Disocv* 12:287-305
Xu et al. (2013) *Proc Natl. Acad. Sci. USA* 100:14634-14639
Yamada et al. (2013) *Virology* 94:270-275
Zauner et al. (2013) *Mol. Cell. Proteomics* 12:856-865

---

The invention claimed is:

1. An EphA4-X, comprising a mammalian EphA4 polypeptide and X, wherein:
   the mammalian EphA4 polypeptide lacks one or more N-glycosylation sites relative to a wild-type mammalian EphA4 polypeptide; and
   X is selected from the group consisting of a portion of an immunoglobluin, a protein and a polyether.

2. The EphA4-X of claim 1, wherein X is an Fc portion.

3. The EphA4-X of claim 2, wherein the EphA4-X comprises an amino acid substitution of an asparagine at amino acid residue 216, 321 and/or 389 relative to human EphA4-Fc with the reference amino acid sequence set forth in SEQ ID NO: 1.

4. The EphA4-X of claim 3 wherein the amino acid substitution is from asparagine to glutamine.

5. The EphA4-X of claim 4 comprising an amino acid sequence selected from the group consisting of SEQ ID NO: 2 through 8 or a sequence having at least 95% sequence identity thereto.

6. The EphA4-X of claim 5 comprising the amino acid sequence as set forth in SEQ ID NO: 8.

7. A pharmaceutical composition comprising the EphA4-X of claim 1 and one or more pharmaceutically acceptable carriers, diluents and/or excipients.

8. A method for treating a disease or condition exacerbated by Eph-mediated signaling in a mammalian subject, said method comprising the administration of an effective amount of the EphA4-X of claim 1.

9. The method of claim 8 wherein X is an Fc portion of an immunoglobulin molecule.

10. The method of claim 9 wherein the Fc is IgG4 Fc or IgG1 Fc.

11. The method of claim 9 wherein the EphA4-X comprises an amino acid substitution of an asparagine at amino acid residue 216, 321 and/or 389 relative to human EphA4-Fc with the reference amino acid sequence set forth in SEQ ID NO:1.

12. The method of claim 11 wherein the amino acid substitution is from asparagine to glutamine.

13. The method of claim 12 wherein the EphA4-X comprises an amino acid sequence selected from the group consisting of SEQ ID NO:2 through 8 or a sequence having at least 95% sequence identity thereto.

14. The method of claim 13 wherein the EphA4-X comprises the amino acid sequence as set forth in SEQ ID NO: 8.

15. The method of claim 11 wherein the EphA4-X is administered in an amount to provide about 5-20 μg/mL serum EphA4-Fc for from 3 to 10 days.

16. The method of claim 8 wherein the disease or condition is a disease or condition of the central nervous system (CNS).

17. The method of claim 16 wherein the disease or condition of the CNS is a neurodegenerative condition.

18. The method of claim 17 wherein the neurodegenerative condition is motor neuron disease (MND).

19. The method claim 18 wherein the disease or condition is trauma or injury to the brain or spinal cord or neuronal inflammation.

20. The method of claim 19 wherein the injury to the brain is a stroke or is traumatic brain injury or brain injury following thrombolysis.

21. The method of claim 18 wherein the EphA4-X prevents or reduces gliosis, glial scarring, neuronal inflammation or neurodegeneration.

22. The method of claim 21 wherein the effective amount of the EphA4-X is the amount sufficient to promote axonal regeneration.

23. The method of claim 8 wherein the disease or condition is a disease or condition of the systemic vasculature.

24. The method of claim 23 wherein the disease or condition of the systemic vasculature is ischemic reperfusion injury, organ reperfusion injury or inflammation.

25. The method of claim 24 wherein the ischemic reperfusion injury is intestinal ischemic reperfusion injury, kidney reperfusion or hepatic reperfusion.

26. The method of claim 8 wherein the disease is myocardial infarction, an inflammatory condition or cancer.

27. The method of claim 8 wherein the mammalian subject is a human.

\* \* \* \* \*